United States Patent
Ivanoff et al.

(10) Patent No.: US 11,101,041 B2
(45) Date of Patent: *Aug. 24, 2021

(54) SYSTEMS AND METHODS OF MANAGING PAYMENTS THAT ENABLE LINKING OF BILLING ACCOUNTS OF ONE OR MORE GUARANTORS

(71) Applicant: iVinci Partners, LLC, Boise, ID (US)

(72) Inventors: Kent F. Ivanoff, Boise, ID (US); Vincent Martino, Eagle, ID (US); Nikolaus Trotta, Boise, ID (US); David Arnett, Boise, ID (US)

(73) Assignee: IVINCI PARTNERS, LLC, Boise, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 16/792,399

(22) Filed: Feb. 17, 2020

(65) Prior Publication Data
US 2020/0258630 A1    Aug. 13, 2020

Related U.S. Application Data

(63) Continuation of application No. 14/590,803, filed on Jan. 6, 2015, now Pat. No. 10,566,090.
(Continued)

(51) Int. Cl.
*G06Q 30/04* (2012.01)
*G06Q 20/10* (2012.01)
(Continued)

(52) U.S. Cl.
CPC .............. *G16H 50/20* (2018.01); *G06Q 10/10* (2013.01); *G06Q 20/102* (2013.01); *G06Q 20/14* (2013.01);
(Continued)

(58) Field of Classification Search
CPC combination set(s) only.
See application file for complete search history.

(56) References Cited

U.S. PATENT DOCUMENTS

| 6,456,983 B1 | 9/2002 | Keyes et al. |
| 7,333,937 B2 | 2/2008 | Baldwin, Jr. et al. |

(Continued)

OTHER PUBLICATIONS

"U.S. Appl. No. 14/590,457, Examiner Interview Summary dated Jun. 24, 2015", 3 pgs.
(Continued)

*Primary Examiner* — Peter Ludwig
*Assistant Examiner* — Reva R Moore
(74) *Attorney, Agent, or Firm* — Schwegman Lundberg & Woessner, P.A.

(57) ABSTRACT

Systems and methods of managing payments for services or products are disclosed. Billing system data is extracted or accessed to provide business intelligence and. Visit charges from multiple billing systems can be aggregated to guarantor accounts within or across multiple billing systems and provide a single statement of charges for a given time period. Accounts are accessible online. Accounts can be linked to delegate management authority of a first guarantor's account to a second (manager) guarantor. Visit charges for linked accounts are included in the manager guarantor's statement an online access. Open charges balances can be brokered or transferred to a new asset holder. Pre-determined payment options can be configured by a provider, asset holder, and/or potential asset holder. The pre-determined payment options can include an option for financing a balance. A configurable financing option may enable a guarantor to request terms and receive automatic approval, subject to authorized terms.

24 Claims, 25 Drawing Sheets

Related U.S. Application Data

(60) Provisional application No. 61/924,121, filed on Jan. 6, 2014.

(51) Int. Cl.
  *G06Q 20/14* (2012.01)
  *G16H 50/20* (2018.01)
  *G06Q 10/10* (2012.01)
  *G06Q 30/02* (2012.01)
  *G06Q 40/02* (2012.01)
  *G16H 40/20* (2018.01)

(52) U.S. Cl.
  CPC ......... *G06Q 30/0201* (2013.01); *G06Q 30/04* (2013.01); *G06Q 40/025* (2013.01); *G16H 40/20* (2018.01)

(56) References Cited

U.S. PATENT DOCUMENTS

| | | | |
|---|---|---|---|
| 7,805,359 B2 | 9/2010 | Lites | |
| 7,813,943 B1 | 10/2010 | Lefco et al. | |
| 8,014,756 B1* | 9/2011 | Henderson | G06Q 20/322 |
| | | | 455/411 |
| 8,095,475 B2 | 1/2012 | Hutson et al. | |
| 8,185,408 B2 | 5/2012 | Baldwin, Jr. et al. | |
| 8,583,492 B2 | 11/2013 | Connell | |
| 8,788,420 B1 | 7/2014 | Green | |
| 10,255,996 B2 | 4/2019 | Ivanoff et al. | |
| 10,566,090 B2 | 2/2020 | Ivanoff et al. | |
| 2002/0023045 A1 | 2/2002 | Feilbogen et al. | |
| 2002/0026407 A1 | 2/2002 | Neubert | |
| 2003/0018563 A1 | 1/2003 | Kilgour et al. | |
| 2003/0050796 A1 | 3/2003 | Baldwin, Jr. et al. | |
| 2004/0024704 A1 | 2/2004 | Yim et al. | |
| 2004/0093281 A1 | 5/2004 | Silverstein et al. | |
| 2005/0021462 A1 | 1/2005 | Teague et al. | |
| 2005/0033609 A1 | 2/2005 | Yang | |
| 2005/0065871 A1 | 3/2005 | Gerhart et al. | |
| 2005/0086126 A1* | 4/2005 | Patterson | A63F 13/792 |
| | | | 705/26.8 |
| 2005/0177435 A1 | 8/2005 | Lidow | |
| 2006/0116906 A1 | 6/2006 | Otterbach et al. | |
| 2006/0173778 A1* | 8/2006 | Lipsky | G06Q 10/10 |
| | | | 705/40 |
| 2006/0190376 A1 | 8/2006 | Mollner et al. | |
| 2006/0229976 A1 | 10/2006 | Jung et al. | |
| 2007/0005402 A1* | 1/2007 | Kennedy | G06Q 40/08 |
| | | | 705/4 |
| 2007/0100747 A1 | 5/2007 | Franklin et al. | |
| 2007/0156572 A1 | 7/2007 | Lites | |
| 2007/0162308 A1* | 7/2007 | Peters | G16H 10/60 |
| | | | 705/2 |
| 2007/0185810 A1 | 8/2007 | Kalra et al. | |
| 2008/0091597 A1 | 4/2008 | Roach | |
| 2008/0288283 A1 | 11/2008 | Baldwin, Jr. et al. | |
| 2009/0083171 A1 | 3/2009 | Stipek et al. | |
| 2009/0276244 A1 | 11/2009 | Baldwin, Jr. et al. | |
| 2012/0179605 A1 | 7/2012 | Blain et al. | |
| 2012/0239417 A1 | 9/2012 | Pourfallah et al. | |
| 2012/0265553 A1 | 10/2012 | Baldwin, Jr. et al. | |
| 2012/0271780 A1 | 10/2012 | Perugini et al. | |
| 2013/0103572 A1 | 4/2013 | Rosenberg | |
| 2013/0275144 A1 | 10/2013 | Bain | |
| 2013/0282394 A1 | 10/2013 | Baldwin et al. | |
| 2014/0039905 A1 | 2/2014 | Stamper et al. | |
| 2014/0222716 A1 | 8/2014 | Joplin | |
| 2014/0236614 A1 | 8/2014 | Whittier et al. | |
| 2014/0337954 A1 | 11/2014 | Ahmed et al. | |
| 2015/0193749 A1 | 7/2015 | Ivanoff et al. | |
| 2015/0193750 A1 | 7/2015 | Ivanoff et al. | |
| 2015/0193787 A1 | 7/2015 | Ivanoff et al. | |
| 2015/0193843 A1 | 7/2015 | Ivanoff et al. | |
| 2015/0193872 A1 | 7/2015 | Ivanoff et al. | |
| 2016/0085926 A1 | 3/2016 | Ivanoff et al. | |
| 2016/0103965 A1 | 4/2016 | Ivanoff et al. | |
| 2016/0342758 A1 | 11/2016 | Ivanoff et al. | |

OTHER PUBLICATIONS

"U.S. Appl. No. 14/590,457, Final Office Action dated Aug. 27, 2015", 45 pgs.

"U.S. Appl. No. 14/590,457, Non Final Office Action dated Mar. 17, 2015", 37 pgs.

"U.S. Appl. No. 14/590,457, Response filed Jun. 15, 2015 to Non Final Office Action dated Mar. 17, 2015", 31 pgs.

"U.S. Appl. No. 14/590,783, Examiner Interview Summary dated Apr. 17, 2015", 3 pgs.

"U.S. Appl. No. 14/590,783, Final Office Action dated Sep. 16, 2015", 25 pgs.

"U.S. Appl. No. 14/590,783, Non Final Office Action dated Feb. 26, 2015", 23 pgs.

"U.S. Appl. No. 14/590,783, Response filed May 22, 2015 to Non Final Office Action dated Feb. 26, 2015", 33 pgs.

"U.S. Appl. No. 14/590,795, Non Final Office Action dated Jul. 3, 2017", 26 pgs.

"U.S. Appl. No. 14/590,803, Advisory Action dated Aug. 22, 2019", 3 pgs.

"U.S. Appl. No. 14/590,803, Appeal Brief filed Sep. 3, 2019", 20 pgs.

"U.S. Appl. No. 14/590,803, Examiner Interview Summary dated Oct. 24, 2017", 2 pgs.

"U.S. Appl. No. 14/590,803, Final Office Action dated Jan. 12, 2018", 27 pgs.

"U.S. Appl. No. 14/590,803, Final Office Action dated Apr. 4, 2019", 27 pgs.

"U.S. Appl. No. 14/590,803, Non Final Office Action dated Jun. 14, 2017", 22 pgs.

"U.S. Appl. No. 14/590,803, Non Final Office Action dated Sep. 24, 2018", 35 pgs.

"U.S. Appl. No. 14/590,803, Notice of Allowance dated Nov. 15, 2019", 23 pgs.

"U.S. Appl. No. 14/590,803, Response filed Jan. 18, 2017 to Restriction Requirement dated Oct. 18, 2016", 11 pgs.

"U.S. Appl. No. 14/590,803, Response filed Jan. 24, 2019 to Non Final Office Action dated Sep. 24, 2018", 21 pgs.

"U.S. Appl. No. 14/590,803, Response filed Jul. 12, 2018 to Final Office Action dated Jan. 12, 2018", 20 pgs.

"U.S. Appl. No. 14/590,803, Response filed Oct. 6, 2017 to Non Final Office Action dated Jun. 14, 2017", 19 pgs.

"U.S. Appl. No. 14/590,803, Response filed Jul. 3, 2019 to Final Office Action dated Apr. 4, 2019", 14 pgs.

"U.S. Appl. No. 14/590,803, Restriction Requirement dated Oct. 18, 2016", 8 pgs.

"U.S. Appl. No. 14/590,817, Advisory Action dated Feb. 27, 2018", 2 pgs.

"U.S. Appl. No. 14/590,817, Appeal Brief filed May 15, 2018", 25 pgs.

"U.S. Appl. No. 14/590,817, Examiner Interview Summary dated Oct. 19, 2017", 3 pgs.

"U.S. Appl. No. 14/590,817, Final Office Action dated Jan. 12, 2018", 11 pgs.

"U.S. Appl. No. 14/590,817, Non Final Office Action dated Jun. 2, 2017", 20 pgs.

"U.S. Appl. No. 14/590,817, Non Final Office Action dated Sep. 6, 2018", 12 pgs.

"U.S. Appl. No. 14/590,817, Response filed Feb. 15, 2018 to Final Office Action dated Jan. 12, 2018", 10 pgs.

"U.S. Appl. No. 14/590,817, Response filed Oct. 2, 2017 to Non Final Office Actio dated Jun. 2, 2017", 18 pgs.

"U.S. Appl. No. 14/954,763, Appeal Brief filed Oct. 17, 2016", 50 pgs.

"U.S. Appl. No. 14/954,763, Appeal Decision dated Oct. 30, 2018", 15 pgs.

"U.S. Appl. No. 14/954,763, Examiner's Answer dated Jan. 9, 2017", 30 pgs.

(56) References Cited

OTHER PUBLICATIONS

"U.S. Appl. No. 14/954,763, Final Office Action dated Jul. 28, 2016", 138 pgs.
"U.S. Appl. No. 14/954,763, Non Final Office Action dated Feb. 25, 2016", 46 pgs.
"U.S. Appl. No. 14/954,763, Reply Brief filed Feb. 21, 2017 to Examiner's Answer dated Jan. 9, 2017", 13 pgs.
"U.S. Appl. No. 14/954,763, Response filed May 18, 2016 to Non Final Office Action dated Feb. 25, 2016", 32 pgs.
"U.S. Appl. No. 14/971,618, Appeal Brief filed Jul. 25, 2016", 47 pgs.
"U.S. Appl. No. 14/971,618, Appeal Decision dated Jul. 13, 2018", 22 pgs.
"U.S. Appl. No. 14/971,618, Examiner's Answer dated Nov. 17, 2016", 13 pgs.
"U.S. Appl. No. 14/971,618, Final Office Action dated May 13, 2016", 32 pgs.
"U.S. Appl. No. 14/971,618, Non Final Office Action dated Feb. 4, 2016", 21 pgs.
"U.S. Appl. No. 14/971,618, Response filed Apr. 15, 2016 to Non Final Office Action dated Feb. 4, 2016", 28 pgs.
"U.S. Appl. No. 14/971,618, Reply Brief filed Jan. 16, 2017", 13 pgs.
"U.S. Appl. No. 15/230,863, Non Final Office Action dated Feb. 22, 2021", 44 pgs.
"U.S. Appl. No. 14/954,763, Notice of Allowance dated Feb. 13, 2019", 9 pgs.
"U.S. Appl. No. 14/590,817, Appeal Brief filed Mar. 11, 2019", 24 pgs.
"U.S. Appl. No. 14/590,817, Reply Brief filed Jul. 23, 2019", 6 pgs.
"U.S. Appl. No. 15/230,863, Restriction Requirement dated Jul. 29, 2019", 6 pgs.
"U.S. Appl. No. 15/230,863, Response filed Aug. 26, 2019 to Restriction Requirement dated Jul. 29, 2019", 13 pgs.
"U.S. Appl. No. 15/230,863, Non Final Office Action dated Dec. 2, 2019", 19 pgs.
"U.S. Appl. No. 15/230,863, Response filed Apr. 2, 2020 to Non Final Office Action dated Dec. 2, 2019", 18 pgs.
Smith, "Flagging economy makes collecting hospital bills a challenge", (2012), 3 pgs.
"U.S. Appl. No. 14/590,817, Appeal Decision dated Jun. 22, 2020", 17 pgs.
"U.S. Appl. No. 15/230,863, Final Office Action dated Jun. 22, 2020", 24 pgs.
"U.S. Appl. No. 15 230,863, Examiner Interview Summary dated Oct. 21, 2020", 2 pgs.
"U.S. Appl. No. 15/230,863, Response filed Oct. 22, 2020 to Final Office Action dated Jun. 22, 2020", 16 pgs.

\* cited by examiner

SYSTEMS AND METHODS OF MANAGING PAYMENTS THAT ENABLE LINKING OF BILLING ACCOUNTS OF ONE OR MORE GUARANTORS

RELATED APPLICATIONS

This application claims priority to U.S. patent application Ser. No. 14/590,803, filed Jan. 6, 2015, which claims priority to U.S. Provisional Patent Application No. 61/924,121, titled SYSTEMS AND METHODS OF MANAGING PAYMENTS, filed Jan. 6, 2014, all of which are hereby incorporated herein by reference in their entirety.

TECHNICAL FIELD

The present disclosure is related to computer-implemented systems and methods of managing payments for services or products.

BACKGROUND

Collecting payments for goods and services provided is a critical function of businesses, particularly where it may be necessary or preferable to bill for services or products subsequent to providing them to a beneficiary (e.g., a customer). Convenience in making payments is of importance to many customers, and the payment experience for remitting payments for billed charges can significantly impact an impression of customers for a business. Computing systems have greatly improved capability of businesses to track and manage collection of payments. The Internet provides a convenient medium for customers to make payments. Nevertheless, current billing systems lack functionality to provide features that would enhance effectiveness of payment collections for businesses. Similarly, current billing systems are fragmented and incomplete and lack functionality to provide features that provide a positive customer payment experience, thus producing confusion and frustration for customers and turning a positive experience into an overall negative experience with the business.

SUMMARY

The present disclosure provides embodiments of computer-implemented systems and methods of managing payments for services or products. Embodiments of the disclosed systems and methods may, for example, enable brokering of charges or balances, configuring financing and payment options for settling amounts owed, assessing guarantor propensity to pay, linking of multiple guarantor accounts to a manager guarantor, linking of accounts across multiple billing systems, gathering and deriving business intelligence data, managing and presenting account data, facilitating dispute resolution, and generating longitudinal portrayals of visits, among other things, to, for example, improve a payment experience for a business, a customer, and other parties involved.

DETAILED DESCRIPTION OF PREFERRED EMBODIMENTS

Figure 1:
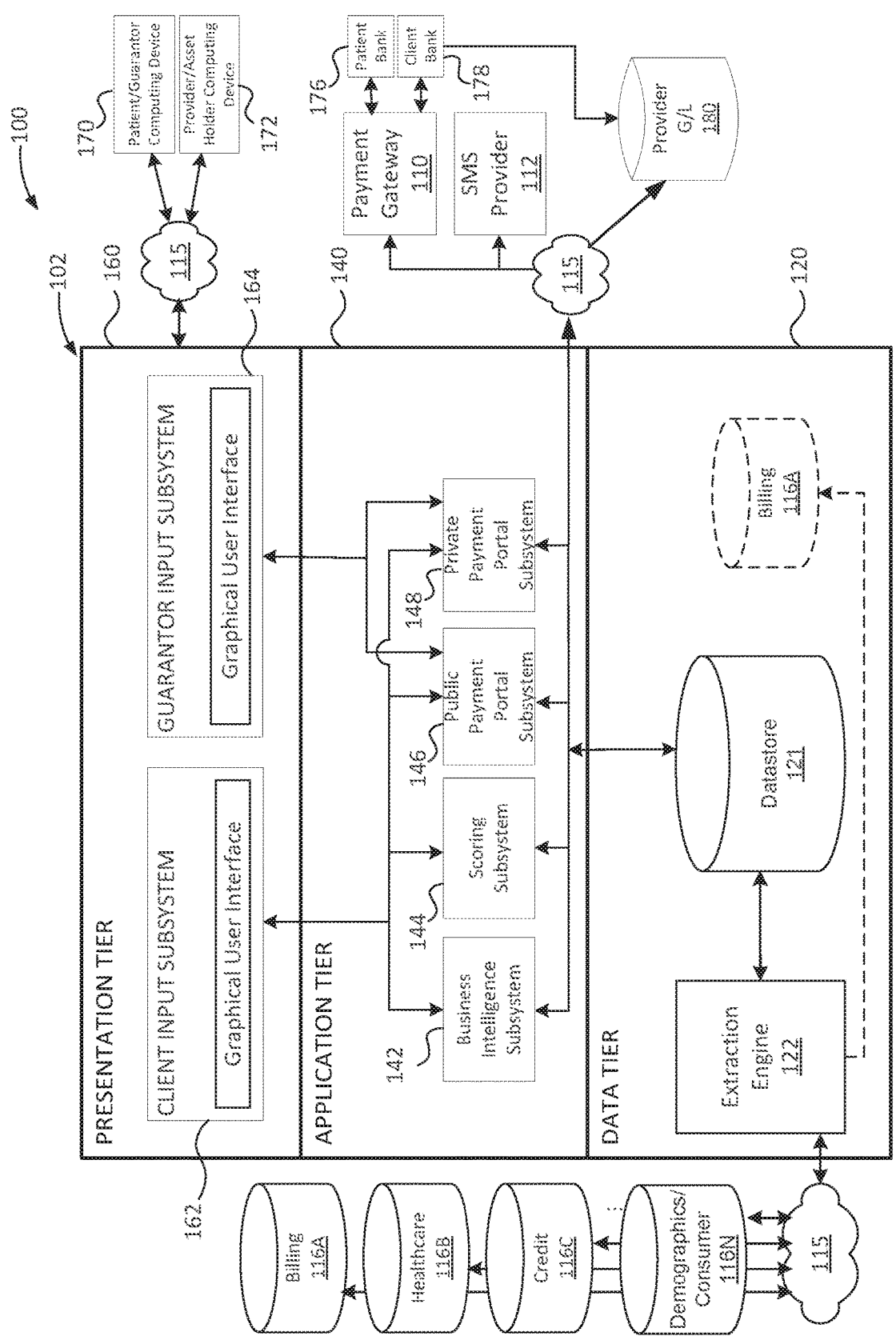
FIG. 1 is a block diagram of a payment management system for managing payments for healthcare services, according to one embodiment.

Collecting payments for goods and services provided is a critical function of businesses, particularly where it may be necessary or preferable to bill for services or products subsequent to providing them to a beneficiary (e.g., a customer). Certain industries face particular challenges in collecting payments. The healthcare industry is an industry in which billing and payment collection is fragmented and tends to produce a negative patient experience.

Current healthcare billing systems (sometimes referred to as Revenue Cycle Management (RCM) systems) are primarily designed to track claims and optimize payments by third-party payers (e.g., insurers). As a result, presently available healthcare billing systems present only vertical (period-based) portrayals of data and information. Specifically, the billing systems can tell a healthcare provider how much cash was collected this month but cannot tell how much of that cash was collected on balances created in any specific month prior as compared to those balances created this month. With only a vertical portrayal, a healthcare provider cannot accurately predict payment rates, understand vendor performance, set intelligent goals, offer intelligent financing, manage repayment risks, etc.

Presently available healthcare billing systems also are not equipped to elegantly manage patient (or guarantor) account balances. Patients/guarantors are generally confused by statements generated by existing billing systems. The patient/guarantor interfaces to billing systems, such as to make online bill payments, are fragmented and incomplete, turning a positive patient care experience into an overall negative experience with the healthcare provider. As an example, presently available healthcare billing systems do not present a guarantor a single electronic statement that includes all charges incurred for multiple disparate visits during a single period. As another example, a guarantor responsible for multiple different patients (e.g., dependents) generally cannot view an electronic aggregation of charges for visits of those different patients, especially over time. A guarantor also cannot link an account, or assume responsibility for an account, of another guarantor (e.g., a spouse) without a tedious paper request and approval process.

There is also a lack of flexible financing options for patients to pay for healthcare services. Similarly, there is a lack of flexible financing options for a variety of beneficiaries to pay for encounters providing goods and/or services, for which the encounter charges are billed to the beneficiary and/or a guarantor of the beneficiary.

There is also a lack of effective systems and methods for assessing the propensity of a guarantor to pay for a particular type of goods or services. For example, the credit scores generated by credit reporting agencies can be poor predictors or indicators of a guarantor's likelihood of paying for healthcare services. Similar shortcomings exist in other industries and markets, including but not limited to dental services, legal services, auto repair services, and other goods and services. Credit reporting agencies are largely dependent on data reported by credit lenders, and are often removed from actual transaction data in specific verticals like healthcare because few providers report payment dynamics to these agencies from actual transaction data. Thus, their credit scores may be limited to data based on transactions involving credit and for goods/services that may have nothing to do with a given market (e.g., healthcare services).

The presently disclosed embodiments provide improved payment management functionality for a service (or product) provider, such as a healthcare provider, and enable an improved billing experience for guarantors of payment for charges billed for a visit.

The term "provider" as used herein refers broadly to an entity providing a product or service. A provider may be a single individual (e.g., a physician) providing a benefit or may be an entire organization (e.g., a healthcare organization with multiple subsidiaries, facilities, locations, departments). In other words, the term "provider" is not limited to a single individual. Rather a provider may include a single individual or entity, a group of individuals or entities, multiple locations, subsidiaries, departments (e.g., laboratory, pathology, anesthesiology, etc.), affiliates, and the like.

The term "guarantor" as used herein refers to a person (or entity) that has assumed primary or at least shared financial responsibility for payment for an amount owed, such as for a product or for services rendered (e.g., healthcare services rendered to a patient), either at a visit or at the time of receipt of such product or service. A guarantor makes or gives a promise, assurance, or pledge relating to financial payment performance on a financial liability, either on behalf of himself/herself or on behalf of another. The guarantor, in some instances, may also be the beneficiary of the product or service (e.g., a patient in the case of healthcare services). Another example of a guarantor may be a parent or legal guardian of a minor. Although in some instances laws or regulations may dictate qualifications for a guarantor (e.g., age requirements, mental capacity), the term herein is not bound to these restrictions.

The term "visit" as used herein refers to an encounter or an instance of receipt of services (or a product). For example, some embodiments of the disclosure are described with reference to healthcare services rendered to a patient, and a visit can be considered a physical visit to a healthcare provider and receipt of healthcare services rendered during that physical visit. However, the disclosed embodiments are not limited to healthcare. Other examples of visits relate to dental services, vision services, mental health services, legal services, automobile services (e.g., mechanic, routine maintenance), and other repair services. An example of a product-related visit may include a purchase of furniture or appliances. As can be appreciated, a visit or encounter may not necessarily involve physical movement of the beneficiary to another location, and can include services or products that come to the beneficiary or that are otherwise performed for or directed to the benefit of the beneficiary.

The term "self-pay" as used herein refers to any obligation owed by the beneficiary (and/or a guarantor) to a provider. In the context of healthcare, self-pay can include co-pays, balances after insurance adjudication, deductible amounts, etc. The term "self-pay" is not intended to reflect whether or not a beneficiary/guarantor is insured. Rather, "self-pay" is intended to encompass any obligation properly owed by the beneficiary/guarantor in the normal course of business. In other words, a provider may consider self-pay receivables as those balances due from patients/guarantors for hospital and physician services as a result of having no insurance or having a balance due even after insurance pays, due to coinsurance, deductibles, or noncovered services.

The presently disclosed embodiments access data (e.g., extract, obtain, collect, receive, or otherwise access data), transform the data, and load the data to generate longitudinal portrayals of the data. A longitudinal portrayal may be cohort-based, where a cohort is a group of guarantor accounts (within a billing system), balances, and/or visits that share a common origination characteristic (typically a specific time period when a corresponding initial debt was incurred) and for which all transactions affecting the balances (e.g., payments, added charges, adjustments, interest, fees) are tracked longitudinally over time. In other words, a longitudinal portrayal includes all transactions affecting the balances of a grouping of accounts as tracked over a period of time. The grouping of accounts may include accounts (e.g. one or more accounts) from independent billing systems and/or balance sheet entities.

The presently disclosed embodiments may collect historical visit data and/or patient information from or within a billing system (or plurality of billing systems) and create a standardized extract file layout for each respective billing system of record for subsequently structuring necessary information to create relevant products to drive self-pay financial performance and patient experience. The presently disclosed embodiments may also collect data from other systems, such as from a credit data source, a demographics data source, and systems affiliated with the provider and/or billing system (e.g., installment loan platforms), to supplement the visit data and/or patient information. Each transaction identified in the collected historical data is date/time stamped so that a longitudinal portrayal can be created of a given visit from the time the initial visit charge is incurred until the visit charge is ultimately resolved. The collected data may be transformed and organized using a data table structure that enables longitudinal views of, for example, guarantor type, service location, service type, guarantor financial class, account status, source of payments, insurance information, balance, patient and guarantor relationships, and cash and non-cash transactions. As a result, a longitudinal view of cash and non-cash transaction dynamics (and other financial performance dynamics) of self-pay balances can be provided.

The disclosed embodiments may use the collected data to provide business intelligence functionality and/or information. An interactive interface can be provided by which a provider can achieve a comprehensive view on the performance characteristics of the provider's self-pay business currently as well as in a given time period or over varying time spans. The business intelligence functionality of the disclosed embodiments can provide a consolidated view of multiple locations, affiliates, provider entities (e.g., subsidiaries, departments, and other organizational groupings), and the like of a given provider (e.g., multiple hospitals and clinics, laboratories, pathology, anesthesiology). The business intelligence can also enable a provider to reliably compare performance and/or effectiveness of third-party vendors (e.g., accounts receivable servicing vendors, debt collection vendors, and the like) on an equal or analogous basis to tightly manage vendor performance. The business intelligence can also enable intelligent forecasts of payor and guarantor cash flows for reserve setting purposes, and enable setting and tracking of goals against such forecasts. Standard reports can be dynamically filtered by hundreds of variables. An ad hoc reporting tool can generate custom reports designed by the user.

The presently disclosed embodiments can also use extracted data to provide propensity-to-pay (PTP) scores. A PTP scoring assessment uses a provider's historical transaction data to help assess likelihood of future guarantor payments based on the specific historical payment behaviors of the guarantor being scored. Presently available scoring solutions rely heavily and often exclusively on credit data provided by credit reporting agencies or demographics data provided by third parties, and neither of these data elements is highly predictive of a given guarantor's PTP in a specific market, such as the healthcare market. Using the provider's historical transaction data greatly improves the predictive capability of the resulting PTP scores. The scoring can consider present visit data and/or past transaction data of the guarantor to the provider. The resulting scoring creates a proprietary, highly predictive score without creating either a "soft" or "hard" hit to the guarantor's file at any one of the three major credit reporting agencies (TransUnion, Equifax or Experian).

The PTP scoring can be "always-on," such that PTP scores automatically update, such as at various stages of account aging, when cash and non-cash transactions occur, and/or in response to triggers. A guarantor with an account balance may be initially assessed for PTP using provider and third-party data, and any subsequent provider-based credit or debit activity on the specific account can result in an updated score (e.g., automatically updating the score). Always-on scoring can enable a provider to create a tailored guarantor billing experience by grouping guarantors into meaningful customer segments that warrant specific action and treatment. Always-on scoring can also enable better account management strategies while accounts are in accounts receivable and can enable better account management strategies for accounts moving to bad debt, inclusive of those accounts recommended for a presumptive charity write-off.

The scoring can also occur "on-demand," or triggered by an event in which a balance is owed (e.g., post adjudication of actual visit charges) or is expected to be owed (e.g., pre-treatment or at the time of treatment). If the balance is expected to be owed, the triggering event may be a provider's estimate of a balance to be owed. If the balance is actually owed, the event may be a provider's actual charge(s) for the balance owed. Once the on-demand scoring occurs, the always-on functionality may enable an on-going perspective of the guarantor in question. If the guarantor is new to the provider, the PTP logic may use the provider's historical payment data for other guarantors, and/or third-party data. On-demand scoring enables appropriate front-end payment collection strategies for patient access areas (scheduling, registration, pre-authorization). An interface may be provided that can guide or direct use of the PTP scoring, for example by personnel of the provider. The interface may enable receiving an estimate of future visit charges. The interface may present one or more PTP scores based on a current open charges balance, an estimate of future charges, or a total balance owed by a guarantor.

The scoring functionality can also include a presumptive charity rank ordering based on PTP assessment for those guarantors that meet charity policy requirements (e.g., requirements specified by the provider or other asset holder) based on third-party demographics data and third-party scores/attributes. By comparison, rank ordering presumptive charity-eligible patients using presently available credit scores, such as are produced purely from credit reporting data or demographics data (and thus not very predictive in any certain industries, such as healthcare), introduces waste and inefficiency.

The disclosed embodiments may use the extracted data and employ rigorous matching logic to automatically populate an account of a registered guarantor with information (and particularly billing information) for visits of the guarantor and/or associated beneficiaries. The guarantor accounts and balances can continue to reside on the originating billing system, and this billing system may remain the system of record for transactions posted to these accounts. The disclosed embodiments can present, for a given billing period, a single digital statement for charges for visits during a given billing period (e.g., 30-day period) and for which the guarantor has accepted financial responsibility. The single statement may combine visit data of multiple beneficiaries from a plurality of billing systems of one or more healthcare service providers.

The disclosed embodiments may also enable a guarantor to, for example, "consolidate a household" with another registered guarantor. This means that a selected guarantor can be designated as a "managing guarantor" of an aggregated group of guarantors (e.g., within a household or a nuclear family) and can interactively manage and/or pay on any guarantor account within that aggregation of managed guarantor accounts (e.g., set up a payment plan or financing plan, pay a specific balance, etc.). The linking is compliant with the Health Insurance Portability and Accountability Act (HIPAA) and allows consolidation of billing management for any number of consenting adults or dependent minors to one singular portrayal of a patient's financial obligations potentially spanning multiple billing systems within a given provider, or for multiple providers, and managed by one authorized accounts manager (or manager guarantor). Account linking is generally very difficult operationally, highly risky from a HIPAA compliance standpoint, and sometimes impossible (across multiple disparate billing systems) in a paper environment. The disclosed embodiments facilitate electronic communications (e.g., requests and acceptances) that enable linking accounts in minutes as compared to weeks or months in a paper world. Thus, the single digital statement of a manager guarantor provides a vehicle to efficiently manage financial records of all healthcare-related transactions for one or more providers and for all members of, for example, a household. Nevertheless, the managed guarantor remains the responsible financial party for his/her visits and the managed guarantor can continue to access account information and make payments on any of his/her specific accounts. The disclosed embodiments may facilitate both guarantors agreeing to the consolidation, and either guarantor can unilaterally terminate the consolidation at any time.

The digital statement provides a singular portrayal of new charges as well as prior charges and transaction history for all linked individuals (patients/guarantors). The digital statement is interactive and dynamic, allowing the guarantor (or manager guarantor) to view as much or as little detail as desired. The digital statement provides the manager guarantor complete transparency on an aggregated statement of charges, with filtering/searching capability to view specific patient accounts within the household for given periods of time and to drill down on any encounter/visit for detailed articulation of charges, including physician, service location, provider revenue code, Current Procedural Terminology (CPT) code, and corresponding descriptions. The filtered searches can be downloaded for import to another application or conversion to another format.

In some disclosed embodiments, a guarantor (including a manager guarantor) may be enabled to select and configure a single monthly due date on which payments will be due to the provider. The digital statement provides a clear, concise portrayal of a guarantor's financial obligations in one statement each month presented with ample time (e.g., 21 days) before a chosen payment date. The digital statement can show pending insurance claims still in the adjudication process. The digital statement may also provide a mechanism for a guarantor to dispute or challenge a questionable set of charges for a given visit/encounter. Thus, the disclosed embodiments can provide an avenue to efficiently flag and resolve disputed charges or raise other issues with the provider and similarly provide a workflow for the provider to address charges disputed or other issues raised by a guarantor.

The disclosed embodiments provide the same functionality for any guarantor of an account even if the guarantor has delegated account management rights to another guarantor (e.g., a manager guarantor). The disclosed embodiments offer encounter-level payment, adjustment, and interest tracking.

Upon receiving the digital statement, a guarantor can choose how to make a payment. While a payment can be made at any time, general choices (e.g., payment options) may be presented upon receipt of the digital statement, such as the following:

Pay in full for new visits to potentially earn a prompt-pay discount, based on choices and/or configured preferences of the healthcare provider and possibly subject to what is allowed by the guarantor's insurance plan.

Customize a new financing plan to pay a new balance comprising charges for visits from a current statement period.

Accept (e.g., by taking no action or affirmatively accepting) preset financing terms for a multi-month financing plan at a pre-established interest rate (e.g., a low or 0.0% interest rate) as configured by the provider or other asset holder.

At the time of filing of this application, the law distinguishes a payment plan, which is presently defined by law to have a duration of four months or less (and subject to certain additional regulatory requirements), from a financing plan, which is presently defined by law to last longer than four months. As used herein, the term "financing plan" includes any payment plan spanning multiple periods (e.g., months), whether or not distinguished according to definition under the law. A financing plan includes open-ended (e.g., revolving) credit as well as closed-ended (e.g., a loan) credit.

The payment options enabled by the disclosed embodiments provide a vehicle through which a guarantor (or manager guarantor) can obtain reliable open-ended credit for current and future financial obligations to a provider. Aggregated current and historical charges are presented to the guarantor (or manager guarantor) for balance management and self-servicing. This information may be presented to a guarantor irrespective of whether management rights have been delegated to a manager guarantor. A guarantor can authorize automated, recurring payments on accounts or make a one-time payment on an account or group of accounts. The same functionality may be available to any guarantor, irrespective of management delegation. A set of charges for a given billing/statement period (e.g., a set of current open charges) that are not paid in full may be placed on a preset financing plan or configured for a custom financing, such that a payment amount will be automatically debited from the guarantor's (or manager guarantor's) selected financial transaction account and automatically credited to specific accounts on the provider's billing system(s).

The amount for current open charges (e.g., an open charges balance) for each statement period's visits can be financed according to a new financing plan with unique terms, which may be preset financing terms or financing terms selected or configured by the guarantor (subject to constraints/authorization of the provider). A guarantor may have multiple financing plans active simultaneously. The disclosed embodiments enable one monthly payment for all open financing plans on a guarantor-configured payment date. The financing option allows a guarantor to create self-configured financing plans, for example, by choosing a monthly payment amount and subsequently accepting the associated terms the provider has authorized for the resulting amortization schedule (e.g., minimum payment amount, maximum amortization period, interest rates, etc.). Self-configured financing plans may be configured by the guarantor choosing any one or more of an interest rate, a payment amount, a period for repayment, and/or other terms that can be compared to provider-authorized terms and/or associated with provider-authorized terms that can be accepted by the guarantor.

The payment options enabled by the disclosed embodiments also provide a vehicle through which a guarantor can pay off an entire set of new monthly charges and potentially receive a prompt payment discount or other discount offered by the provider. The disclosed embodiments enable providers to effectively offer and administer prompt payment discounts as well as other types of discounts.

The disclosed embodiments enable automatic transactions (or transfers of funds) on a configured payment date and using a configured payment method. Payment preferences can be configured by each guarantor, including but not limited to the payment date, a preferred mode of payment (e.g., checking account, savings account, credit card, debit card, Health Savings Account), and/or a preferred payment option (e.g., pay in full, preset financing terms, custom financing terms). A guarantor can link one or more financial transaction vehicles of choice to automatically settle payments on new obligations and historical financings with a balance still due.

The features of the disclosed embodiments provide control and choice for how a guarantor (or manager guarantor) manages healthcare financial obligations.

The disclosed embodiments may enable provider-level, guarantor-level, and/or visit-level decisioning and/or underwriting such that any visit or set of visits for any patient and/or for any guarantor can be channeled customized financing terms. The decisioning may include decisioning rules that define criteria to group guarantors. The criteria, as mentioned, may be at a provider-level, a guarantor-level, and/or a visit-level (e.g., provider, guarantor income estimate, balance amount, insurance carrier, type of treatment, etc.). Providers can also enable automated discounts for uninsured patients pursuant to the provider's policies.

The disclosed embodiments may enable brokering of charges and/or balances. A balance for a batch of open charges, or an open charges balance can be automatically evaluated based on one or more pre-defined evaluation criteria to determine whether the open charges balance should be transferred to a new system of record associated with a new entity. If the one or more pre-defined evaluation criteria are met, the disclosed embodiments may automatically effectuate electronic transactions to transfer the open charges balance to an entity associated with the new system of record. More particularly, the disclosed embodiments may automatically effectuate electronic transactions to transfer title of an accounts receivable asset that constitutes some or all rights to collect payment for the open charges balance. The disclosed embodiments may track transactions relating to the open charges balance, including payments to pay the current batch of open charges, and this tracking may be separate from the first billing system.

The disclosed embodiments may also enable providers or other asset holders to offer guarantors interest-bearing financing plans. The disclosed embodiments can track and manage interest. The financing plans can enable a provider to secure incremental payments from guarantors and lower the provider's cost of servicing accounts. The financing plans can ease a payment burden on a guarantor by spreading payments over a period of time (e.g., monthly payments for several months).

The disclosed embodiments can generate automated posting files for the provider billing system(s) such that proper accounts are credited with payment and/or assessed interest. Adjustments can be automatically applied at the visit level to ensure any overpayments on interest are applied to principal or credited back to the guarantor's appropriate financial account. For example, the disclosed embodiments may receive first visit data tracked in a first billing system, including a charge for a first visit, and second visit data being tracked in a second billing system, including a charge for a second visit. The second billing system is independent from the first billing system. The disclosed embodiments may communicate a transaction request to a payment gateway to request the payment gateway process an electronic financial transaction to obtain payment funds in a payment amount from a payor financial institution associated with a payment vehicle, to transfer a first portion of the payment funds to a payee financial institution associated with the first patient billing system, and to transfer a second portion of the payment funds to a payee financial institution associated with the second patient billing system. The disclosed embodiments may also communicate electronic posting files to notify the first billing system of transfer of the first portion of the payment funds toward payment of the charge for the first visit and to notify the second billing system of transfer of the second portion of the payment funds toward payment of the charge for the second visit. In this manner, guarantor accounts can be linked across billing systems.

FIG. 1 is a block diagram of a system 100 for managing payments for healthcare services, according to one embodiment. The system 100 of FIG. 1 includes a payment management system 102 configured to interface with a billing data source 116A, a healthcare data source 116B, a credit data source 116C, a demographics/consumer data source 116N, a payment gateway 110, and/or a short message service (SMS) provider 112. The payment management system 102 may interface the data sources 116A-N over a network 115 and/or may access one or more of the data sources 116A-N locally on computing devices of the payment management system 102 or storage directly accessible by the payment management system 102. For example, the billing data source 116A is shown in FIG. 1 as accessible over a network 115 (e.g., in a case of a separate, distinct billing system of a provider) and as optionally accessible within the data tier of the payment management system 102 (e.g., in a case of an integrated payment management system 102 and provider billing system). The system 100 may interface with and assist one or more client healthcare providers (e.g., a provider of healthcare services that is a client of the payment management system, sometime referred to as a client provider or more simply as a provider). The system 100 facilitates management by a client healthcare provider of payments by patients (or guarantors of patients) for healthcare services rendered to a patient by the client healthcare provider. The billing data source 116A and/or healthcare data source 116B may be a billing system (or a plurality of billing systems of one or more client healthcare providers). The healthcare data source 116B may be a health information system (or a plurality of health information systems of one or more client healthcare providers).

The system 100 utilizes collected data, such as data received (e.g., obtained, extracted, or otherwise accessed) from the billing data source 116A, the healthcare data source 116B, the credit data source 116C, and/or the demographics/consumer data source 116N, to provide payment management functions for the client healthcare provider and associated guarantors. The functions provided by the system 100 include, but are not limited to: providing business intelligence information to the client healthcare provider, assessing PTP scoring information, brokering charges and/or balances to transfer a corresponding accounts receivable asset to a new asset holder, enabling offers of configurable financing and payment terms to beneficiaries and/or guarantors, linking accounts of guarantors across billing systems, and linking accounts of guarantors to an account of a manager guarantor.

The business intelligence provided by the system 100 may include information to enable a provider to reliably compare performance and/or effectiveness of third-party vendors (e.g., A/R servicing vendors, debt collection vendors, and the like) on an equal or sufficiently analogous basis to tightly manage vendor performance. The business intelligence can also enable intelligent forecasts of payor and guarantor cash flows for reserve setting purposes, and enable setting and tracking of goals against such forecasts. Standard reports can be dynamically filtered by hundreds of variables, including but not limited to facility vs. professional billing, location, balance range, patient/guarantor financial class, timer period, etc. An ad hoc reporting tool can generate custom reports designed by the user. The generated reports can be pushed via the provider's email system. Generated reports can also be pulled, for example, through electronic, system-generated subscription functionality. A client provider viewing a report may be able to drill down on any reported element to the individual guarantor accounts that comprise the reported element and subsequently display additional account-level information on that universe of accounts (e.g., double-click on a section of a bar graph and see a detailed listing of all individual accounts that comprise that data set).

The PTP scoring provided by the system 100 may include using a client provider's historical transaction data to help assess the likelihood of future guarantor payments based on the specific historical payment behaviors of the guarantor being scored or a like guarantor (e.g., having similar payment characteristics and/or attributes). The PTP scoring can be "always-on," such that scores automatically update, such as at various stages and/or in response to triggers, as described previously. The PTP scoring can also occur "on-demand," or triggered by an event in which a new balance is owed or is expected to be owed, as described previously.

The system 100 also utilizes extracted data to provide payment and/or communication functionality to patients (or other beneficiaries) and/or guarantors of patients. For example, the system 100 provides the ability for a patient/guarantor to view account information and provide payment information for healthcare services, and the system 100 interfaces with the payment gateway 110 for processing the payment. The payment gateway 110 may effectuate or otherwise facilitate electronic payment transactions between a patient (or guarantor) financial institution 176 and a provider (or asset holder) financial institution 178. The system 100 can present, for a given billing period, a single statement for visits during the given billing period for which the guarantor has accepted financial responsibility. The single statement may combine visit data from a plurality of billing systems of one or more client healthcare service providers. As another example, the system 100 also interfaces with the SMS provider 112 to facilitate communication with the patient and/or the patient's guarantor.

The system may also interface with the provider's general ledger (G/L) 180 to provide communications to reconcile what is posted to the provider's G/L to individual accounts within the billing system. For guarantor payments that only involve principle, that reconciliation may be generally straightforward because the posting files to the billing system, which go through that system to the provider's G/L, tie exactly to the files that go from the payment gateway 110 to the provider G/L in terms of money transferred. The complexity increases when a portion of the payment is allocated to interest charges, because the billing system may not have any ability to deal with the concept of interest. As such, an 'interest payment' file can be posted to the provider's G/L to tie the cash the provider received from the payment gateway 110 (in terms of money transferred to provider's bank 178) to what the provider is showing in its billing system. Otherwise, it would appear that the billing system amount (which is principle only in the case of a billing system that cannot account for interest) is short (and it is by the amount of interest). If a billing system can handle interest, posting files may only be posted to the billing system (and not to the provider's G/L) because existing reconciliation processes between the provider's billing system and the provider's G/L are available for both principle and interest. The payment gateway 110 may still post a posting file to the provider's G/L and that amount can be reconciled solely to the billing system records.

The system 100 can automate brokering of charges and/or balances. A batch of open charges of a guarantor (and any linked or managed guarantors) in a given period can be aggregated from the data extracted from one or more billing systems to determine an open charges balance. The open charges balance can be automatically evaluated by the system 100, based on one or more pre-defined evaluation criteria, to determine whether the open charges balance should be transferred to a new system of record associated with a new entity. If the one or more pre-defined evaluation criteria are met, the system 100 may automatically effectuate electronic transactions to transfer the open charges balance to an entity associated with the new system of record. The system 100 may be the new system of record.

The system 100 can enable configurable financing and payment terms by allowing a provider to configure pre-set financing terms or authorized financing terms that can be offered to guarantors for an open charges balance. The authorized financing terms may allow guarantor configuration of a financing plan, while the pre-set financing terms may not allow guarantor configurability. Further, the system 100 can evaluate the open charges balance to determine an appropriate set of terms (e.g., pre-set financing terms and/or authorized financing terms) to offer for the open charges balance.

The system 100 can link guarantor accounts to a guarantor who has accepted management responsibility. The system 100 can facilitate electronic communications to obtain any required consent to manage and/or authorization to delegate management authority. Upon appropriate approvals, the account data of a managed guarantor can be aggregated with account data of the manager guarantor.

The system 100 can also link guarantor accounts across billing systems. First visit data originated in a first billing system and second visit data originated in a second billing system can be aggregated for a guarantor to allow presentation of the guarantor's visit data from both billing systems in a singular interactive electronic statement. The system 100 also facilitates payments for the aggregated open charges balance, initiating the appropriate financial transactions between payor and payee financial institutions and communicating posting files to the billing systems to notify of the portion paid toward specific charges originated in each billing system.

The payment management system 102 may implement or otherwise provide one or more of the foregoing functionality. The payment management system 102 of FIG. 1 is structured to include a data tier 120, an application tier 140, and a presentation tier 160. The data tier 120 can extract, collect, transform, store, and otherwise manipulate data for use by the application tier 140 and/or for presentation by the presentation tier 160. The application tier 140 may utilize data of the data tier 120 to provide payment management functions. The presentation tier 160 may present to users of the system, including client healthcare providers and/or patients/guarantors of the client healthcare providers, information and/or an interface to the payment management functions enabled by the application tier 140.

The data tier 120 may include an extraction engine 122 and one or more databases in a datastore 121. The extraction engine 122 may be configured to extract data from the billing data source 116A, the healthcare data source 116B, the credit data source 116C, and/or the demographics/consumer data source 116N for use by the system 100. The extraction engine 122 may be configured to simply aggregate or otherwise collect data tracked in a first billing system of which the payment management system 102 is a component or of which is integrated into the payment management system 102. In other words, extraction by the extraction engine may simply be collection or other access of local and directly accessible data, and is not limited to retrieving or extracting data from external or remote data sources. The extraction engine 122 may translate, convert, transform, or otherwise structure the extracted and/or collected data and may load the transformed data to the datastore 121 and/or to data structures of databases in the datastore 121. The extraction engine 122 is discussed in greater detail below with reference to FIG. 2.

The application tier 140 may include a business intelligence subsystem 142, a scoring subsystem 144, a public payment portal subsystem 146, and a private payment portal subsystem 148. These subsystems leverage data extracted and/or stored by the data tier 120 to provide payment management features and functionalities.

The business intelligence subsystem 142 provides business intelligence information and functionality to a client healthcare provider. The business intelligence subsystem 142 may be configured to generate reporting information pertaining to any aspect of the payment management system 102. The business intelligence subsystem 142 may be further configured to generate forecasts of accounts receivable activity based on PTP metrics corresponding to outstanding balances.

The scoring subsystem 144 provides PTP and presumptive charity information and functionality to a client healthcare provider. The scoring subsystem 144 may be configured to assign PTP scores and/or segmentation or grouping identifiers derived from those PTP scores to accounts managed by the payment management system 102. The PTP scores may incorporate information regarding the transaction history of the account guarantor with the healthcare system. PTP scores may also incorporate information related to the condition of the patient, credit reporting information, demographics, and/or the like. The scoring subsystem 144 may be further configured to identify accounts that are candidates for presumptive charity based on, inter alia, PTP scoring and/or other information indicating that the guarantor is unlikely to have the ability to pay (e.g., balance history, credit reporting information, demographics, and/or the like).

The public payment portal subsystem 146 allows unregistered guarantors to pay charges for healthcare services. The guarantor may be notified of the charges, for example, by a bill or statement mailed in paper format. The public payment portal subsystem 146 enables a client provider to offer a uniform, single online (or electronic) payment interface, regardless of the client provider billing system in which the charges for the healthcare services may be originated, tracked, stored, and otherwise managed. In other words, a client healthcare provider that utilizes a plurality of billing systems (e.g., due to acquisition of business units, clinics, hospitals, and the like) can manage payments to any of these plurality of billing systems through the disclosed embodiments. The public payment portal subsystem 146 allows guarantors who may not be registered for the private payment portal subsystem 148 to make payments through the disclosed embodiments.

The private payment portal subsystem 148 enables a registered guarantor to log in and be presented with protected health information (PHI) that facilitates payment and account management. Through the private payment portal subsystem 148, the registered guarantor can view visit information to better understand charges for a visit. The registered guarantor can view an electronic billing statement reflecting charges for visits incurred during the statement period. The electronic billing statement may reflect an aggregation of charges originated at a plurality of different billing systems. The registered guarantor can also request to have an account managed by another registered guarantor or alternatively request to manage the account of another registered guarantor. The electronic billing statement of a manager guarantor may reflect charges of managed guarantors. In some embodiments, a client provider may coordinate linking of accounts, such as by sending a request to a guarantor to take a manager guarantor role and requesting another guarantor be managed by the manager guarantor.

The presentation tier 160 may include a client input subsystem 162 and a guarantor input subsystem 164. The client input subsystem 162 may present or otherwise provide a graphical user interface for a client healthcare provider to interface with the system 100. In some embodiments, the graphical user interface may be provided through or otherwise integrated with an interface of a billing system.

Figure 3:
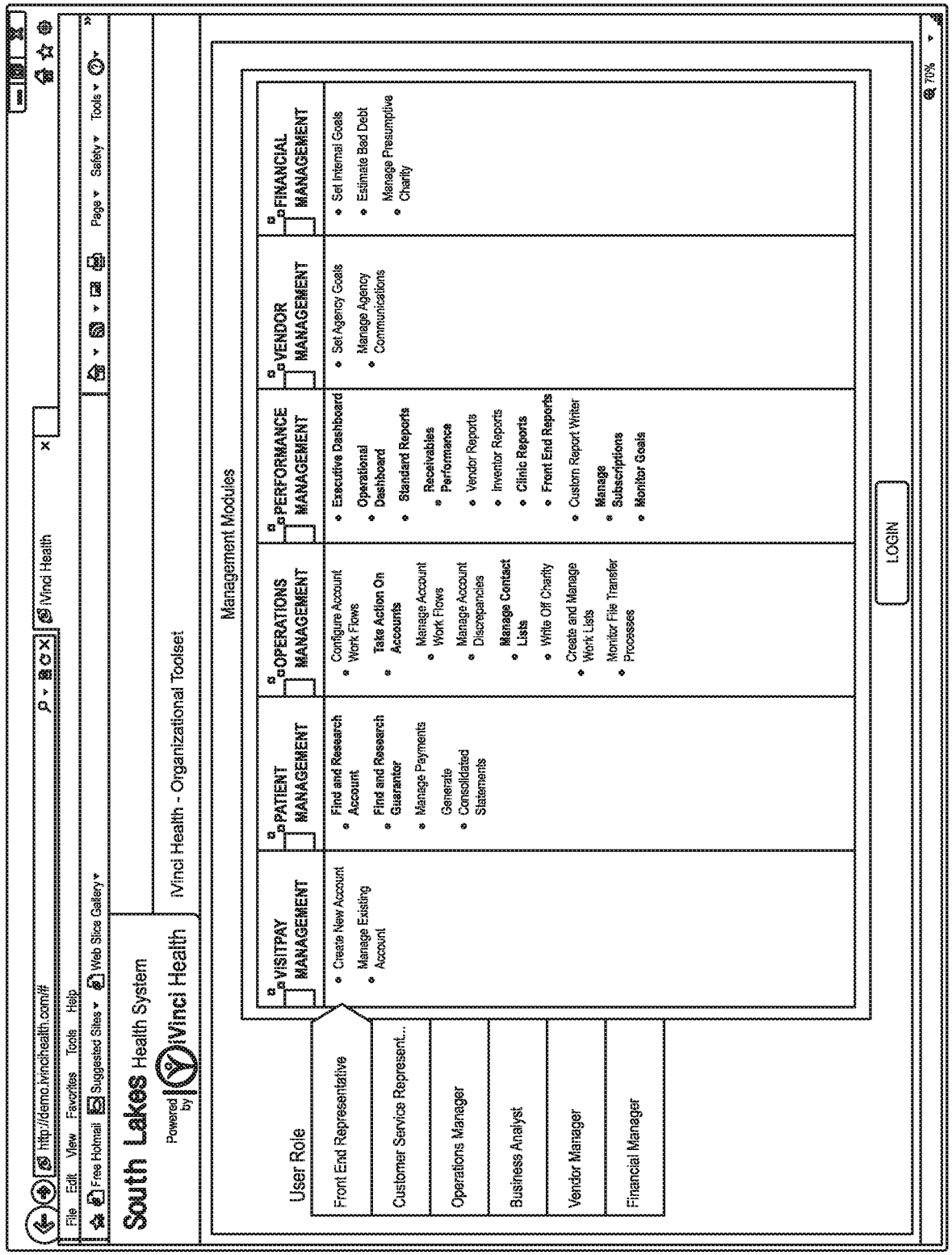
FIG. 3 illustrates a graphical user interface of a client input subsystem of a payment management system, according to one embodiment.

The client input subsystem 162 may more particularly interface with the business intelligence subsystem 142 and/or the scoring subsystem 144 to enable a client healthcare provider to view and otherwise access and/or manipulate business intelligence information provided by the business intelligence system 142 and/or to access scoring functionality provided by the scoring subsystem 144. An example of a graphical user interface of a client input subsystem 162 is shown in FIG. 3 and discussed below with reference to the same.

Figure 9:
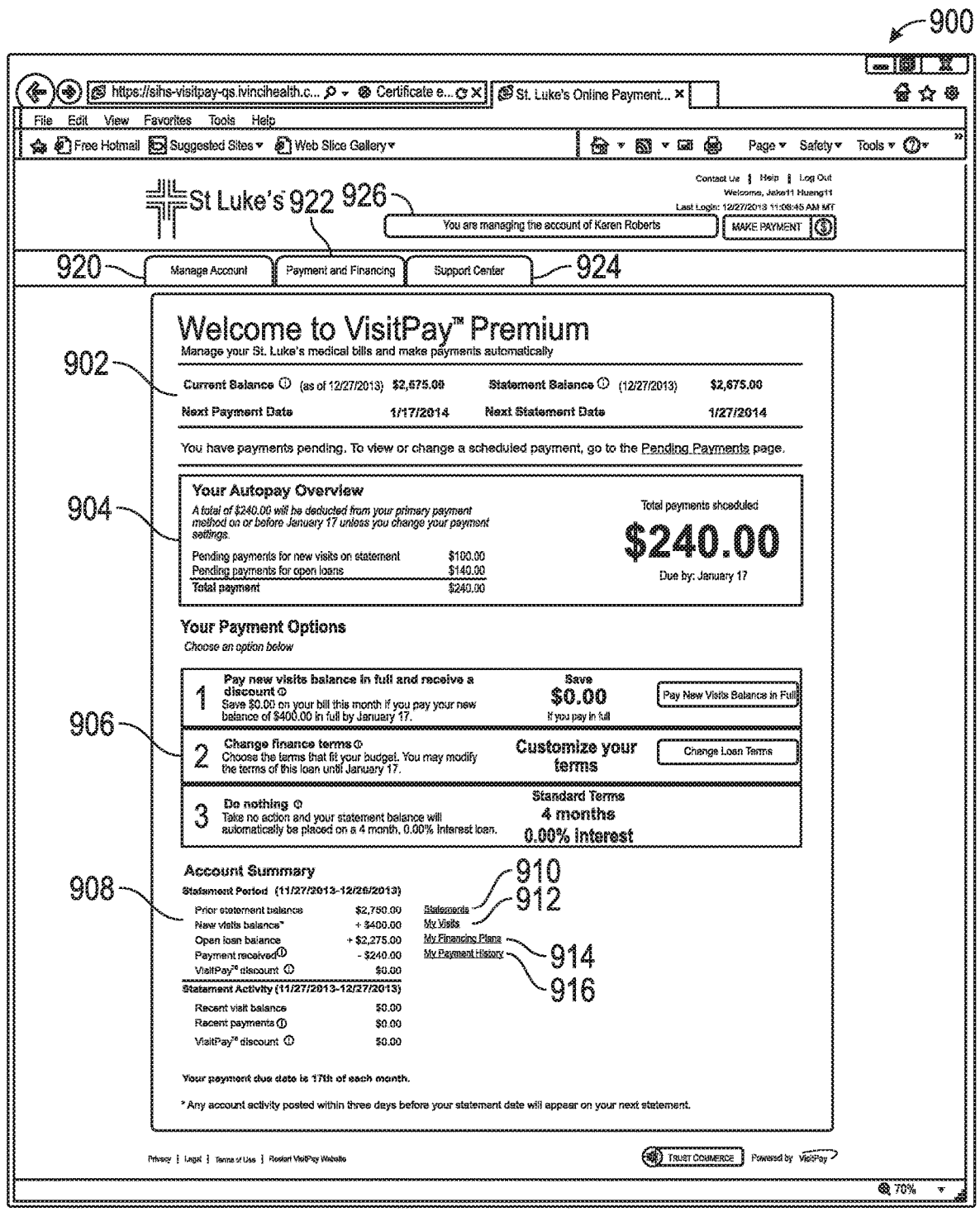
FIG. 9 illustrates a graphical user interface of a patient input subsystem of a payment management system, according to one embodiment.

The guarantor input subsystem 164 may present or otherwise provide a graphical user interface for a guarantor to interface with the system 100. The guarantor input subsystem 164 may more particularly interface with the public payment portal subsystem 146 and/or the private payment portal subsystem 148 to enable a patient or guarantor to view statements, make payments, link to accounts of other guarantors, and the like. An example of a graphical user interface of a guarantor input subsystem 164 is shown in FIG. 9 and discussed below with reference to the same.

The graphical user interface(s) of the client input subsystem 162 and the guarantor input subsystem 164 may be provided to a patient/guarantor computing device 170, a provider/asset holder computing device 172, and/or other client computing device, such as via a network 115 (e.g., over the Internet). Described differently, the system 100 may implement a software as a service (SaaS) delivery model in which the payment management functionality provided by the system 100 and associated data are accessed over the Internet. However, as can be appreciated, the system 100 may be implemented using other appropriate architectures and configurations. For example, the disclosed embodiments may be deployed directly on or using computing devices of a client provider, for example, inside the client provider's firewall. As another example, the disclosed embodiments may be deployed within and/or on a client provider's billing system.

Extraction Engine

The extraction engine 122 may be configured to access information pertaining to particular guarantors, patients, organizations, and/or the like. As disclosed in further detail herein, the information gathered by the extraction engine 122 may be used by the payment management system 102 to provide improved payment management functionality. The extraction engine 122 may be configured to acquire data from one or more data sources 116A-N. The extraction engine 122 may be configured to access the data sources 116A-N by use of the network 115. The network 115 may comprise any suitable communication infrastructure, including, but not limited to, a Transmission Control Protocol/Internet Protocol (TCP/IP) network, a Local Area Network (LAN), a Wide Area Network (WAN), a Virtual Private Network (VPN), a Storage Area Network (SAN), and/or the like.

In other embodiments, the extraction engine 122 may access the one or more data sources 116A-N directly, such as in local storage. Stated differently, the extraction engine 122 may extract data merely by accessing local data sources or otherwise directly accessible data sources. Extraction is not limited to extracting or otherwise obtaining data from external or remote data sources.

The billing data sources 116A may include one or more hospital billing systems, clinic billing systems, practitioner billing systems (e.g., physician billing systems), and/or the like. The healthcare data sources 116B may include, but are not limited to: electronic health record systems, Personal Health Record (PHR) systems, Personal Health Information Technology (PHIT) systems, Electronic Health Record (EHR) systems, Health Information Exchange (HIE) systems, and/or the like. The credit data sources 116C may include credit reporting agencies, such as Equifax, Experian, TransUnion, and/or the like. The demographics/consumer data sources 116N may include demographic and/or consumer profiling data sources configured to provide information including, but not limited to: census information (e.g., date of birth, head of household, marital status, ethnicity, age, education level, and the like), household information (e.g., phone number, number of dependents, length of residence, residence status, residence size, residence value, and the like) economic information (e.g., income level, purchasing power, and the like), mortgage information (e.g., mortgage amount, rate, term, and the like), neighborhood information, socio-economic indicators, and so on.

The extraction engine 122 may be configured to access the data sources 116A-N in accordance with applicable regulations, which may include, but are not limited to, regulations of the HIPAA, Payment Card Industry Data Security Standard (PCI DSS), Sarbanes-Oxley Act (SOX), Fair Credit Reporting Act (FCRA), Fair and Accurate Credit Transactions Act (FACTA), self-imposed regulations (e.g., a privacy policy or contract), jurisdictional regulations (e.g., data access regulations of particular states, countries, and/or regions), and/or the like. The extraction engine 122 may be further configured to access data of the data sources 116A-N according to particular data sharing protocols and/or standards. In some embodiments, the extraction engine 122 is configured to transform, convert, and/or translate information acquired from the data sources 116A-N for use by the payment management system 102.

As depicted in FIG. 1, the data tier 120 may comprise the datastore 121 configured to manage information used by the modules, subsystems, services, and/or components of the payment management system 102. The datastore 121 may comprise any suitable data storage and/or management system including, but not limited to, a database management system (DMBS), a Structured Query Language (SQL) database, an eXtensible Markup Language (XML) database, an object database, a key-value storage system, a file system, a directory (e.g., an X509 directory), and/or the like. The datastore 121 may comprise a schema that defines a data format, structure, and/or arrangement. The extraction engine 122 may be configured to transform data acquired and/or derived from the data sources 116A-N in conformance with the database schema, and to transfer such data into the datastore 121.

Figure 2:
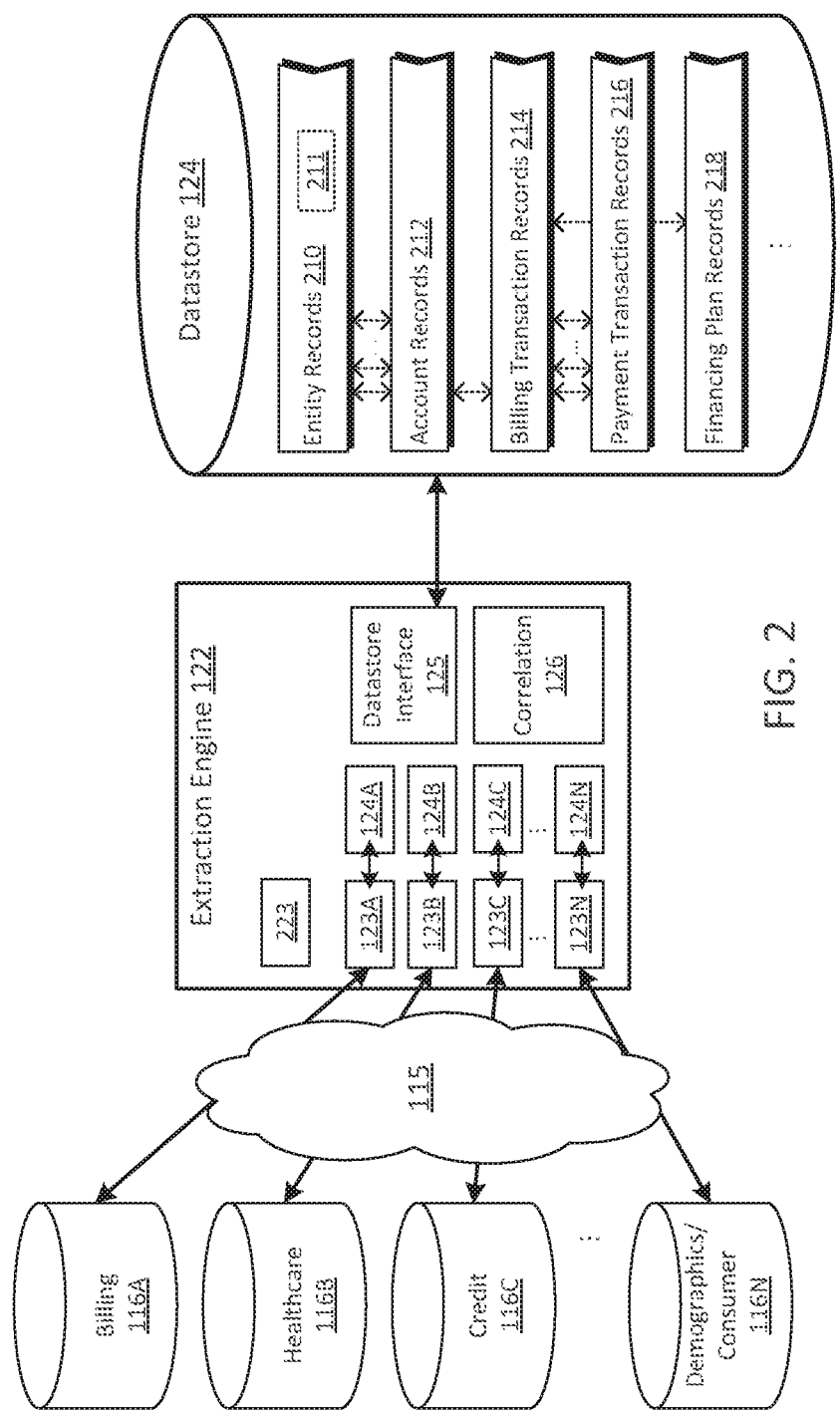
FIG. 2 is a block diagram of an extraction engine of a payment management system, according to one embodiment.

FIG. 2 is a block diagram of one embodiment of an extraction engine 122. In the FIG. 2 embodiment, the extraction engine 122 comprises data source adapters 123A-N, which may be configured to interface with respective data sources 116A-N. The data source adapter 123A, for example, may be configured to access one or more billing data sources 116A through, for example, a Simple Object Access Protocol (SOAP) interface of the billing data sources 116A, the data source adapter 123B may be configured to access one or more healthcare data sources 116B using Secure File Transfer Protocol (SFTP), and so on. The data source adapters 123A-N may be further configured to issue queries to the data sources 116A-N. The queries issued by the data source adapters 123A-N may be configured to acquire particular types of information pertaining to particular entities, such as particular guarantors (e.g., individuals), organizations, accounts, residences, and/or the like. The data source adapters 123A-N may be further configured to push data to the data sources 116A-N (e.g., update the contents of the data sources 116A-N with additional credit reporting information, demographic information, and/or the like). Although FIG. 2 depicts a plurality of data source adapters 123A-N, the disclosure is not limited in this regard and could be adapted to use a single data source adapter 123A-N to interface with a plurality of different data sources 116A-N.

The data source adapters 123A-N may be configured to secure data transferred to/from the data sources 116A-N by, for example, authenticating the data sources 116A-N, providing authentication credential(s) to the data sources 116A-N, encrypting data transmitted to/from the data sources 116A-N, signing data transmitted to/from the data sources 116A-N, and/or the like. In some embodiments, the data source adapters 123A-N are configured to communicate with the data sources 116A-N by use of respective, mutually authenticated secure sockets layer (SSL) connections.

The extraction engine 122 may comprise a data access policy module 223 configured to manage data access operations of the data source adapters 123A-N. The data access policy module 223 may be configured to: a) ensure compliance with data access restrictions applicable to the data sources 116A-N; b) manage authentication credentials of the data sources 116A-N (e.g., credentials used to authenticate the data sources 116A-N to the extraction engine 122, such as public key certificates, cryptographic signatures, Kerberos tickets, and/or the like); c) manage authentication credential(s) of the data source adapters 123A-N (e.g., credentials used to authenticate the data source adapters 123A-N to the data sources 116A-N, such as private keys, and/or the like); d) maintain auditing information pertaining to operations of the data source adapters 123A-N; and e) perform other similar functions. The auditing information may be stored in the datastore 121 and/or another storage system. Although FIG. 2 depicts a single data access policy module 223, the disclosure is not limited in this regard and could be adapted to include a plurality of policy modules 223 (e.g., a separate data access policy module 223 for each data source adapter 123A-N).

The datastore 121 may comprise a directory of entity records 210, which may comprise information pertaining to particular patients and/or guarantors of the healthcare system. In some embodiments, the entity records 210 include, inter alia, data access rules 211. The data access rules 211 may specify, inter alia, the types of information the payment management system 102 is authorized to access for particular entities. For example, a data access rule 211 for an entity may indicate whether the payment management system 102 is allowed to access healthcare information pertaining to the entity from a healthcare data source 116B. The data access policy module 223 may be configured to manage the data access rules 211 in the datastore 121; the data access policy module 223 may be configured to set and/or update data access rules 211 pertaining to particular entities in response to inputs received through one or more of: a) the client input subsystem 162, b) the guarantor input subsystem 164, and/or c) other configuration interface(s). The data access rules 211 may further include preferences regarding privacy, data sharing, and/or the like. The data access rules 211 may be configured to ensure compliance with the data access regulations, disclosed above. Accordingly, the data access policy module 223 may be configured to secure the data access rules 211, such that the data access rules 211 are only modified and/or updated in response to authorized requests. The data access policy module 223 may, for example, be configured to authenticate requests to modify the data access rules 211 to ensure that the modifications are authorized by the corresponding entity and/or entity guardian.

The data source adapters 123A-N may be configured to request or otherwise access data from the data sources 116A-N in accordance with the data access rules 211. The data source adapters 123A-N may, for example, only access healthcare information pertaining to entities that have authorized such access. The data access rules 211 may be further configured to limit access to particular types of information. A data access rule 211 may, for example, exclude certain types and/or classes of healthcare information from being accessed by the payment management system 102.

As disclosed above, the data source adapters 123A-N may be configured to request data from respective data sources 116A-N by, inter alia, issuing requests for data pertaining to particular entities. The requests may be configured to comply with the data access rules 211, disclosed above. In one embodiment, a data source adapter 123B may be configured to access specific healthcare information pertaining to a particular entity from a healthcare data source 116B. Similarly, a data source adapter 123C may be configured to acquire credit information pertaining to a particular entity from a credit data source 116C, and/or a data source adapter 123N may be configured to acquire specific demographic information pertaining to the particular entity from a demographics/consumer data source 116N. Alternatively, or in addition, one or more of the data source adapters 123A-N may be configured to access data in one or more bulk transfer operations. In one embodiment, the data source adapter 123A may be configured to perform bulk transfer operations to acquire all of the billing records for a particular period (e.g., a day) from a billing data source 116A. In another embodiment, the one or more data source adapters 123A-N may be configured to access data of respective data sources 116A-N, and in real time. As an example, the data source adapter 123A may access the billing records of a billing data source 116A (e.g., a billing system and/or records local to, or integrated with, the payment management system 100 of FIG. 1).

The data source adapters 123A-N may be configured to acquire data according to data sharing protocol(s), format(s), or arrangement(s) supported by the respective data sources 116A-N, which may differ from the data protocol(s), format(s), and/or arrangement(s) of the datastore 121. The extraction engine 122 may, therefore, comprise data transformation modules 124A-N configured to transform, convert, and/or translate data acquired from the data sources 116A-N for use by the payment management system 102. The transformation modules 124A-N may be configured to parse data structures acquired from the respective data sources 116A-N and to transform the constituent data into a format that is compatible with the schema of the datastore 121. Although FIG. 2 depicts separate transformation modules 124A-N corresponding to particular data sources 116A-N (and/or data source adapters 123A-N), the disclosure is not limited in this regard and could be adapted to include a single transformation module configured to transform, convert, and/or translate data of a plurality of different data sources 116A-N.

As disclosed above, the extraction engine 122 may be configured to acquire or otherwise access data pertaining to healthcare transactions from one or more billing data sources 116A (by use of data source adapters 123A), and to transform the billing information into a normalized data format compatible with the datastore 121. The extraction engine 122 may further include a datastore interface module 125 configured to store corresponding records in the datastore 121. The extraction engine 122 may be configured to store billing transaction records 214, which may be configured to track bills issued to a particular patient and/or guarantor. A billing transaction record 214 may include, but is not limited to, a transaction identifier (e.g., invoice and/or bill identifier), a time stamp (the date and/or time corresponding to the billing transaction), the payee (e.g., hospital, clinic, service provider, etc.), service(s) provided, service type, service provider(s), service location, patient, patient type, bill type, and/or the like. The extraction engine 122 may be configured to associate billing transaction records 214 with particular patient(s) and/or guarantor(s). In some embodiments, the extraction engine 122 is configured to maintain such associations by use of links and/or references to account records 212 and entity records 210.

The bill type may indicate whether the corresponding billing transaction pertains to an amount that is non-adjudicated, adjudicated, self-pay, split balance, payment plan, financing plan, and/or the like. A non-adjudicated billing transaction record 214 refers to a billing transaction that may be covered by insurance, but that insurance adjudication has not yet taken place. A non-adjudicated billing transaction record 214 may be generated at the time the patient is discharged, at the time of the visit, and/or the like. An adjudicated billing transaction record 214 refers to a billing transaction that has been adjudicated by the insurer. Accordingly, an adjudicated billing transaction record 214 may include a self-pay amount to be paid by the patient and/or guarantor associated with the billing transaction record 214. A self-pay billing transaction record 214 refers to a portion of a billing transaction that is directed to a patient obligation (e.g. a charge not covered by insurance and/or the self-pay portion of an adjudicated billing transaction). Therefore, like the adjudicated billing transaction record 214 above, a self-pay billing transaction record 214 indicates a balance that is payable by the patient and/or guarantor associated with the billing transaction record 214. A split balance billing transaction record 214 refers to a billing transaction record 214 corresponding to a portion of a balance payable by a particular patient and/or guarantor. A financing plan billing transaction record 214 refers to a billing transaction associated with a financing plan (e.g., financing plan record 218), as disclosed in further detail herein. Although particular bill types are described herein, the disclosure is not limited in this regard and could be adapted to include any suitable bill type corresponding to any suitable billing condition, balance type, or the like.

The extraction engine 122 may be configured to acquire information pertaining to particular patients and/or guarantors (entities) of the payment management system 102. Such information may include, but is not limited to, entity identifying information (e.g., name, birthdate, address, contact information, social security number (SSN), and/or the like), insurance information (health insurance provider, limits, deductibles, co-payments, and/or the like), demographic information (neighborhood, socio-economic characteristics, and/or the like), credit information, healthcare-related information, scoring metrics, data access rules 211, and/or the like. The contents of the entity records 210 may be aggregated from the data sources 116A-N. An entity record 210 may include identifying information acquired from a billing data source 116A, credit information from a credit data source 116C, demographics and consumer information from a demographics/consumer data source 116N, and/or the like. In some embodiments, entity records 210 may further include healthcare information related to the patient (e.g., patient type) determined from information in a healthcare billing transaction and/or healthcare data source 116B.

The extraction engine 122 may be further configured to include information pertaining to patient-guarantor relationships. An entity record 210 may, for example, identify one or more guarantors. As disclosed above, a guarantor refers to an entity that is at least partially responsible for healthcare costs of a particular patient. The entity record 210 of such a patient may identify the guarantor(s) that have assumed responsibility for healthcare costs of the particular patient. Similarly, the entity record 210 of a guarantor may identify the patient(s) for whom the particular entity has assumed responsibility. In one example, the entity records 210 of a family may be correlated or otherwise associated, such that entity record(s) 210 of the parent(s) and/or guardian(s) of the family reference entity record(s) 210 of the dependent(s) of the family (and vice versa). Although examples of familiar patient-guarantor relationships are described herein, the disclosure is not limited in this regard; patient-guarantor relationships can be formed between any consenting adults. Moreover, in some embodiments, a guarantor is not responsible for financial obligations; instead, the guarantor may be granted management rights to coordinate payment for an account.

The patient-guarantor relationships may be determined by use of a correlation engine 126. The correlation engine 126 may be configured to determine patient-guarantor relationships by use of information acquired from one or more of the data sources 116A-N, including, but not limited to, billing transaction information (e.g., a guarantor may be specified by the billing data source 116A), healthcare information (e.g., parent-child relationships) acquired from a healthcare data source 116B, demographic information, and/or the like. Alternatively, or in addition, the correlation engine 126 may be configured to establish patient-guarantor relationships in response to inputs provided through one or more of the client input subsystem 162 and/or guarantor input subsystem 164, as disclosed in further detail herein.

The patient-guarantor relationships managed by the correlation engine 126 may be used to generate respective account records 212. The account records 212 may identify a patient and guarantor(s) (e.g., may be linked to a patient entity record 210 and guarantor entity record(s) 210). As disclosed above, in some instances, the patient and guarantor may be one and the same (e.g., the patient may be solely responsible for payment and, as such, may act as his or her own guarantor). Alternatively, a guarantor may be responsible for billing transactions corresponding to one or more other entities (e.g., a parent may act as the guarantor for billing transactions corresponding to his or her dependents). Accordingly, and as illustrated in FIG. 2, an account record 212 may reference (and/or be linked to) a plurality of entity records 210.

The extraction engine 122 may be configured to link account records 212 to billing transaction records 214 by use of the correlation engine 126. The correlation engine 126 may be configured to associate a billing transaction record 214 with an account record 212 by a) accessing information in the billing transaction record 214 that identifies a patient and/or guarantor (e.g., patient and/or guarantor name, all or portion of an SSN, and/or the like); b) identifying entity record(s) 210 corresponding to the patient and/or guarantor in the datastore 121 using the identifying information and/or the patient-guarantor relationships of the entity records 210; and c) linking the billing transaction record 214 with an existing account record 212 corresponding to the accessed entity record(s) 210, or generating a new account record 212 for the billing transaction record 214.

The extraction engine 122 may be further configured to acquire information pertaining to payment transactions from the billing data sources 116A (by use of the data source adapters 123A). In response, the extraction engine 122 may be configured to store a payment transaction record 216 in the datastore 121 (by use of a transaction module 124A and/or datastore interface 125). The payment transaction record 216 may include, but is not limited to, a transaction identifier (e.g., invoice and/or bill identifier), a payment date, a payment source (e.g., cash, check, credit card, etc.), a payment type (e.g., full payment, co-payment, etc.), payee-identifying information, an indication of where the transaction took place (e.g., hospital, clinic, on-line, etc.), and/or the like. The correlation engine 126 may be configured to link the payment transaction record 216 to a billing transaction record 214 based on, inter alia, the transaction identifier, patient- and/or guarantor-identifying information of the payment transaction record 216, and/or the like. The balance of a billing transaction record 214 may be paid over a number of different payment transactions; therefore, and as illustrated in FIG. 2, a billing transaction record 214 may reference (and/or be linked to) a plurality of payment transaction records 216.

The transaction information acquired by the extraction engine 122 may comprise a normalized, longitudinal data set, which may be leveraged by other subsystems of the payment management system 102. Referring to FIG. 1, in some embodiments, the business intelligence subsystem 142 in the application tier 140 of the payment management system 102 is configured to generate information and/or metrics pertaining to billing and/or payment transactions processed by the payment management system 102. As disclosed in further detail herein, the business intelligence subsystem 142 may be configured to generate interactive reports pertaining to any suitable aspect and/or metric pertaining to the payment management system 102, including, but not limited to, performance of billing systems (e.g., time to pay, payment rate); payment metrics filtered by balance range, demographics, time period, insurance coverage, and/or the like; user-designed reports; and so on. The interactive reports generated by the business intelligence subsystem 142 may further comprise scoring information generated by the scoring subsystem 144.

Client Input Subsystem

FIG. 3 illustrates a graphical user interface 300 of a client input subsystem of a payment management system, according to one embodiment. The user interface 300 provides an interactive interface by which a client provider can achieve a comprehensive view on the performance characteristics of the client provider's self-pay business currently, as well as in a given time period or over varying time spans. The business intelligence functionality of the disclosed embodiments can provide a consolidated view of multiple locations of a given client provider (e.g., multiple hospitals and clinics). The business intelligence functionality can also enable a client provider to reliably compare performance and/or effectiveness of third-party vendors (e.g., accounts receivable servicing vendors, debt collection vendors, and the like) on an equal or analogous basis to tightly manage vendor performance. The business intelligence functionality can also enable intelligent forecasts of payor and guarantor cash flows for reserve setting purposes and enable setting and tracking of goals against such forecasts. Standard reports can be dynamically filtered by hundreds of variables. An ad hoc reporting tool can generate custom reports designed by the user.

The graphical user interface 300 enables a client provider user to interface with the client input subsystem 162 to access the functionality of the business intelligence subsystem 142 and the scoring subsystem 144 of FIG. 1. The graphical user interface 300 may also enable the client provider to interface with the client input subsystem 162 to access the functionality of the public payment portal subsystem 146 and/or the private payment portal subsystem 148 of FIG. 1. The graphical user interface 300 may enable configuring settings, for example, in a client-configured database in the datastore 121 of FIG. 1.

Business Intelligence

Figure 4:
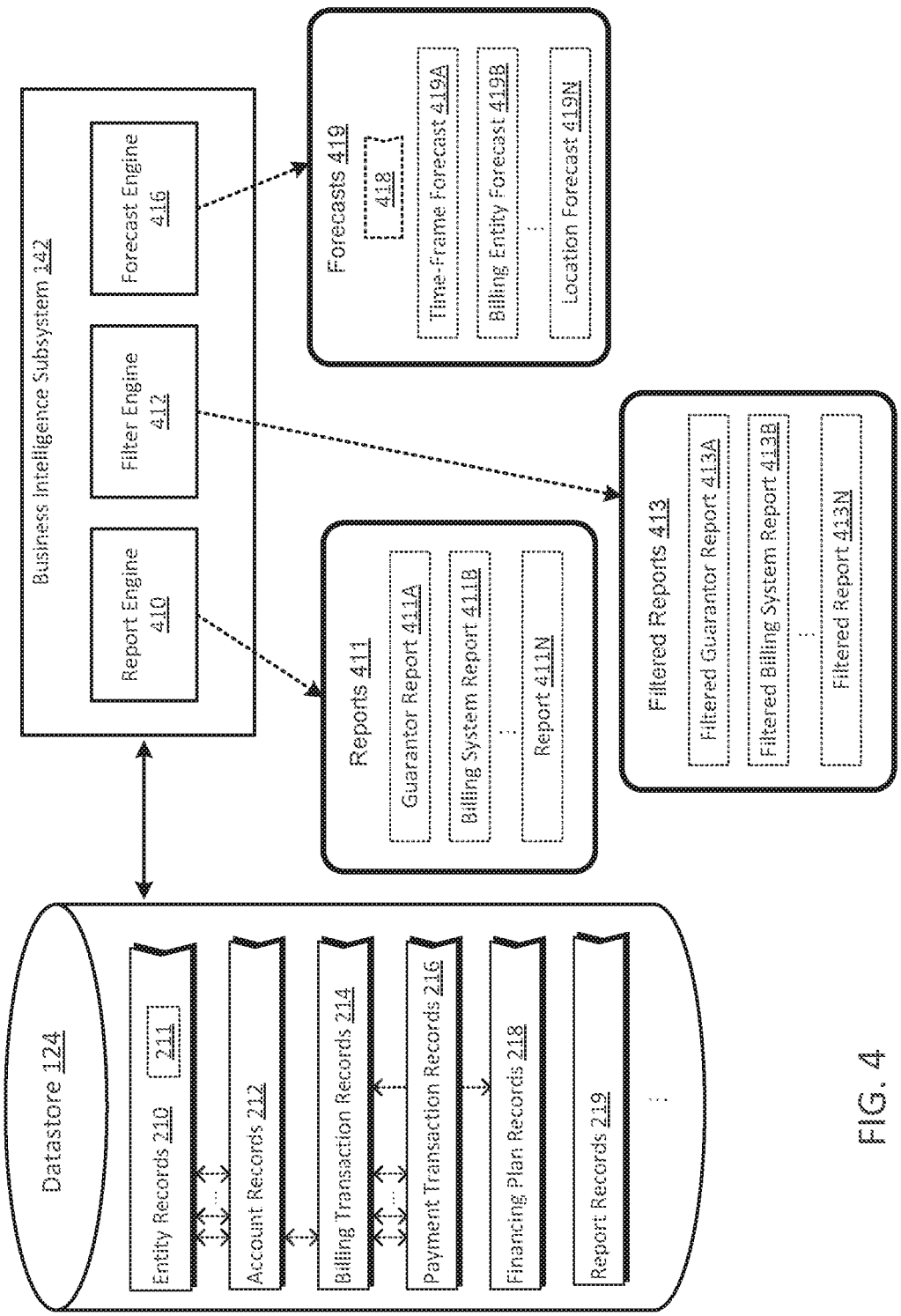
FIG. 4 is a block diagram of a business intelligence subsystem of a payment management system, according to one embodiment.

FIG. 4 illustrates one embodiment of a business intelligence subsystem 142. The business intelligence subsystem 142 may comprise a report engine 410, a filter engine 412, and a forecast engine 416. The report engine 410 may be configured to generate reports 411 based on, inter alia, the contents of the datastore 121. As disclosed above, the billing transaction records 214 and corresponding payment transaction records 216, account records 212, and/or entity records 210 may comprise a longitudinal portrayal of the transactions processed (e.g., originated) by billing systems coupled to the payment management system 102 (e.g., billing systems coupled to the billing data sources 116A of FIG. 1). The report engine 410 may be configured to aggregate data pertaining to billing transaction records 214 maintained in the data store 124 to generate reports 411. The reports 411 may comprise aggregate data pertaining to a particular guarantor, billing system, hospital, clinic, service provider, and/or the like. A report 411A pertaining to a particular guarantor may comprise a history of billing transactions in which a particular individual was a guarantor. The history may correspond to a particular time frame, visit type, and/or other criterion. The report 411A may include information aggregated from a plurality of billing transaction records 214 and corresponding payment transaction records 216 (if payments have been made) that conform to the selection criterion. The report 411A may further include payment metrics, such as time to pay, payment method, insurance coverage, and/or the like. The report 411A may, therefore, comprise a longitudinal, cohort-based portrayal of transactions pertaining to the guarantor. As used herein, a cohort may be a group of guarantor accounts and corresponding billing transaction records 214 and/or payment transaction records 216 that share a common origination characteristic (typically a specific time period when an initial debt was incurred) and for which payment and debt resolution dynamics are tracked longitudinally over time. The report 411A may include other information regarding the guarantor, such as credit history information, demographic information, and/or the like, which may be maintained in an entity record 210 corresponding to the guarantor, as disclosed above.

The report engine 410 may be further configured to generate a report 411B retaining to a particular billing system (e.g., hospital, clinic, service provider, professional, and/or the like). The report 411B may include a history of billing transaction records 214 and/or payment transaction records 216 (if any) that satisfy a particular selection criterion (e.g., that pertain to services provided by a particular service provider and/or managed by a particular billing system). The report engine 410 may be configured to generate other reports 411N corresponding to any suitable aspect of the payment management system 102.

The filter engine 412 may be configured to dynamically filter the reports 411A-N to generate corresponding filtered reports 413A-N. The filter engine 412 may be configured to filter report data based on one or more filter criteria. Exemplary filter criteria may include, but are not limited to, clinic versus hospital billing (e.g., compare payment metrics of payment transactions of a particular clinic to payment transactions of a particular hospital), billing location, balance, patient and/or guarantor financial class (and/or other demographic characteristics), time frame, and/or the like. The business intelligence subsystem 142 may be configured to make the reports 411 and/or filtered reports 413 available to the presentation tier 160 for display to a user. The business intelligence subsystem 142 may be further configured to create reports 411 and/or filtered reports 413 in response to inputs provided via the client input subsystem 162 and/or guarantor input subsystem 164. Alternatively, or in addition, the business intelligence subsystem 142 may be configured to actively generate and/or update report data for use by the payment management system 102. The business intelligence subsystem 142 may be configured to generate one or more reports 411 and/or filtered reports 413 in response to the extraction engine 122 injecting data of one or more data sources 116A-N into the datastore 121. The reports 411 and/or filtered reports 413 may be maintained in respective report records 219 in the datastore 121.

In some embodiments, the business intelligence subsystem 142 may further comprise a forecast engine 416, which may be configured to generate cash flow forecasts for both expected payer and patient cash payments on balances residing on and off a provider's balance sheet (e.g., accounts receivable, financing plans held off balance sheet, bad debt, etc.) based on, inter alia, PTP scoring data and historical payment characteristics corresponding to the account records 212 and/or billing transaction records 214.

The reports 411, filtered reports 413, and/or forecasts 419 generated by the business intelligence subsystem 142 may incorporate one or more PTP scores and/or segmentation classifications. As disclosed above, a PTP score refers to a PTP metric, which may be derived, in part, from data acquired from the data sources 116A-N and, in particular, to billing and/or payment transaction records 214, 216. The application tier 140 may comprise a scoring subsystem 144 configured to generate PTP scores. In some embodiments, the scoring subsystem 144 is configured to generate different types of PTP scores based on a "stage" of an account (e.g., account's status within the client provider's billing system, such as pre-A/R, A/R, bad debt, etc.).

Scoring

Figure 5A:
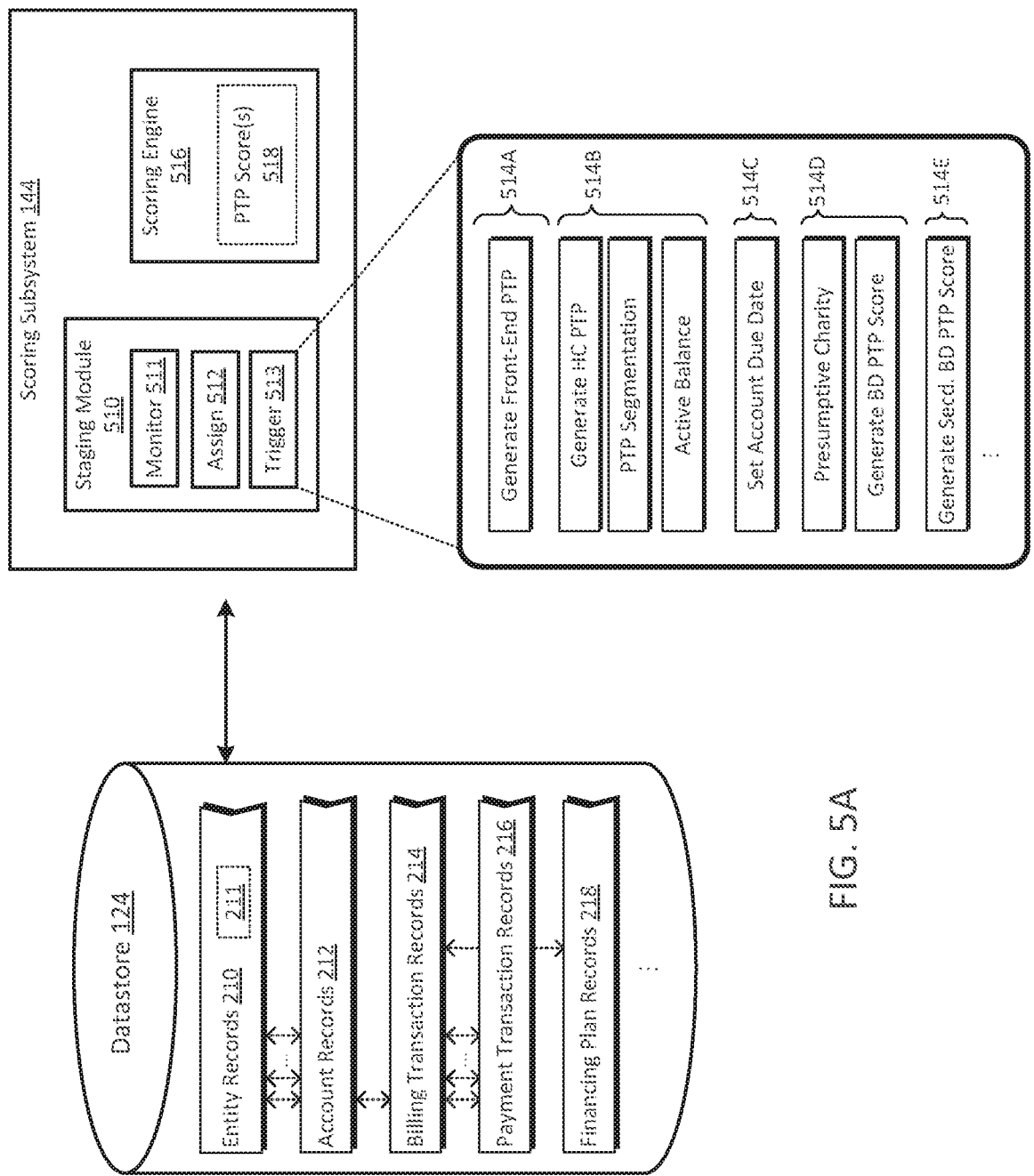
FIG. 5A is a block diagram of a scoring subsystem of a payment management system, according to one embodiment.

FIG. 5A depicts one embodiment of a scoring subsystem 144. The scoring subsystem 144 may comprise a staging module 510 configured to determine a stage of an account record 212 (and/or guarantor(s) associated with the account record 212) and a scoring engine 516 to generate PTP scores and/or segmentation identifiers (e.g., to identify a segmentation classification) pertaining to the account record 212 and/or corresponding guarantor(s) based on, inter alia, the determined stage. As used herein, an account stage refers to a payment status of an account record 212. Account stages may include, but are not limited to, an account creation stage (stage 0), a self-pay stage (stage 1), a financing plan stage (stage 2), a bad debt stage (stage 3), a secondary bad debt (stage 4), and so on. The staging module 510 may be configured to assign stages to account records 212 in response to particular conditions and/or criteria. The staging module 510 may be further configured to implement predetermined trigger actions in response to assigning an account record 212 to particular stages.

The staging module 510 may be configured to determine the current stage of an account record 212 based on data acquired from the billing data sources 116A (e.g., billing transaction records 214 and/or payment transaction records 216). In some embodiments, the staging module 510 comprises a monitor 511 configured to detect staging events regarding accounts managed by the payment management system 102. In some embodiments, the monitor 511 comprises stored procedural code configured for execution by the datastore 121 in response to particular conditions (e.g., a stored procedure, database trigger, or the like). As disclosed above, the conditions pertaining to account staging may include, but are not limited to, creation of and/or modifications to account records 212, billing transaction records 214, payment transaction records 216, financing plan records 218, and/or the like. Alternatively, or in addition, the monitor 511 may be configured to query the datastore 121 to identify events relevant to account staging and/or may be triggered by the extraction engine 122 in response to, inter alia, the extraction engine 122 injecting data into the datastore 121.

In some embodiments, the staging module 510 includes an assignment engine 512 configured to determine a current state of an account record 212 in response to detecting relevant staging events in the datastore 121 (by use of the monitor 511). The assignment engine 512 may designate an account record 212 as a stage 0 account in response to one or more of the following: a) creation of the account record 212 in the datastore 121, b) associating the account record 212 with a non-adjudicated billing transaction record 214 (based on the bill type of the account record 212), c) associating the account record 212 with a patient and/or guarantor (e.g., an entity record 210), and/or d) other similar actions. The assignment engine 512 may designate an account record 212 as a stage 1 account (self-pay account) in response to associating the account record 212 with an adjudicated, self-pay, and/or split-balance billing transaction record 214. The assignment engine 512 may designate an account record 212 as a stage 2 account (financing plan) in response to creating a financing plan record 218 corresponding to the account record 212 (e.g., in response to setting up a financing plan for one or more billing transaction records 214 associated with the account record 212). The assignment engine 512 may designate an account record 212 as a stage 3 account (bad debt) in response to determining that the billing system has marked an account as bad debt and/or determining that a billing transaction record 214 associated with the account record 212 has not been paid within a predetermined accounts receivable (AR) cycle of the corresponding billing system (e.g., has remained unpaid for 120 days or longer). The assignment engine 512 may designate an account record 212 as a stage 4 account (secondary bad debt) in response to determining that the billing system has marked an account as secondary bad debt and/or determining that a billing transaction record 214 associated with the account record 212 has not been recovered in a first bad-debt recovery cycle. The assignment engine 512 may be further configured to update the account record 212 in the datastore 121 to indicate the stage assigned to the account record 212 (e.g., the account record 212 may include a stage field configured to indicate the stage assigned thereto). Although particular stages and/or stage assignment criteria are described herein, the disclosure is not limited in this regard and may be adapted to assign account records 212 to any suitable stage corresponding to any suitable payment management status and/or action(s).

The staging module 510 may further comprise a trigger engine 513 configured to implement one or more triggered actions 514A-E in response to one or more of the following: a) assigning a stage to an account record 212, b) updating data pertaining to an account record 212 in the datastore 121, c) a request for updated stage assignment information, and/or d) other similar actions.

The triggered actions 514A corresponding to stage 0 (account creation) may include generating a front-end PTP score for the account record 212.

The triggered actions 514B corresponding to stage 1 (self-pay) may include generating a healthcare PTP score corresponding to the account record 212, sending PTP segmentation identifiers and/or information to the corresponding billing system(s), and/or creating a record of a self-pay balance for use by the payment management system 102.

The triggered actions 514C corresponding to stage 2 (financing plan) may include a) creating a financing plan record 218 corresponding to the account record 212 (if not yet created) and b) setting a due date for the financing plan record 218. The due date may be used to determine whether the account should be placed into stage 3 (bad debt) due to failure to make timely payments.

The triggered actions 514D corresponding to stage 3 (bad debt) may include a) determining whether the account record 212 is a candidate for presumptive charity and/or b) generating a bad debt PTP score for the account record 212.

The triggered actions 514E for stage 4 (secondary bad debt) may comprise generating a secondary bad debt PTP score for the account record 212.

Determining whether an account record 212 is suitable for presumptive charity may include calculating a charity score for the account record 212 using, inter alia, PTP score(s) calculated for the account record 212 and/or other data, such as a current health condition of the patient and/or guarantor(s), amount owed, income level, credit reporting information, and the like. For example, guarantors can be assessed for financial assistance eligibility by comparing a household income estimate and a size of household estimate to a percentage of the Federal Poverty Level to determine a charity write-off (e.g., for a given household size, some percentage of the Federal Poverty Level qualifies the guarantor for xx % charity write-off). Typically, an abundance of guarantors become "eligible" according to this approach using strictly "estimates" of income and household size. These eligible guarantors can be ranked according to PTP score(s) for each account record 212 to determine how the charity write-offs are actually dispersed. A PTP threshold can be adjusted up or down to either channel more or less money to charity depending on a charity write-off budget.

A charity score may be calculated by receiving third-party data such as from a credit data source 116C and/or demographic/consumer data source 116N (FIG. 1) to generate an ability-to-pay estimate or otherwise determine an ability-to-pay of a guarantor. The ability-to-pay estimate may be compared to the provider's financial assistance eligibility criteria to determine whether the guarantor qualifies for financial assistance under the provider's charity or hardship programs. If charity eligible, a prioritization decision may determine which guarantor accounts to recommend for presumptive charity based on a rank ordering by the PTP score.

A charity score may also be calculated using solely data from the billing data source 116A and/or the healthcare data source 116B. In other words, a charity score may be calculated without relying upon credit reporting data (e.g., traditional credit bureau data) and/or demographics/consumer data. The scoring engine 516 may be configured to calculate a charity score for an account and determine whether the account is a candidate for presumptive charity by comparing the charity score to a threshold. The staging module 510 may be configured to identify account records 212 that are candidates for presumptive charity to an administrator of the payment management system 102, who may selectively write off the candidate accounts.

The scoring engine 516 of the scoring subsystem 144 may be configured to generate PTP scores 518 for account records 212. The scoring engine 516 may be configured to generate PTP scores 518 in response to a) updates to the datastore 121 (e.g., in response to receiving relevant data from the data sources 116A-N) and/or b) the triggered actions 514A-E of the trigger engine 513 (e.g., active, always-on scoring). Alternatively, or in addition, the scoring engine 516 may be configured to generate other PTP metrics, such as guarantor segment (or group) identifier, in response to requests received through, inter alia, interface(s) of the presentation tier 160 (e.g., on-demand scoring). The other PTP metrics may indicate a propensity to pay an amount owed. For example, a guarantor segment (or group) identifier may indicate a segment, group, classification, category, or the like, in which the guarantor belongs. A propensity-to-pay may be associated with the metric (e.g., a guarantor grouping) and thereby may indicate collection strategies for the guarantor and/or may be used to determine financing terms, similar to how a PTP score can be used. The scoring engine 516 may be further configured to generate different types of PTP scores 518 in accordance with a stage of the account records 212 and/or in response to requests for particular PTP score types (e.g., front-end PTP score, healthcare (HC) PTP score, bad debt (BD) PTP score, secondary BD PTP score, and so on).

Figure 5B:
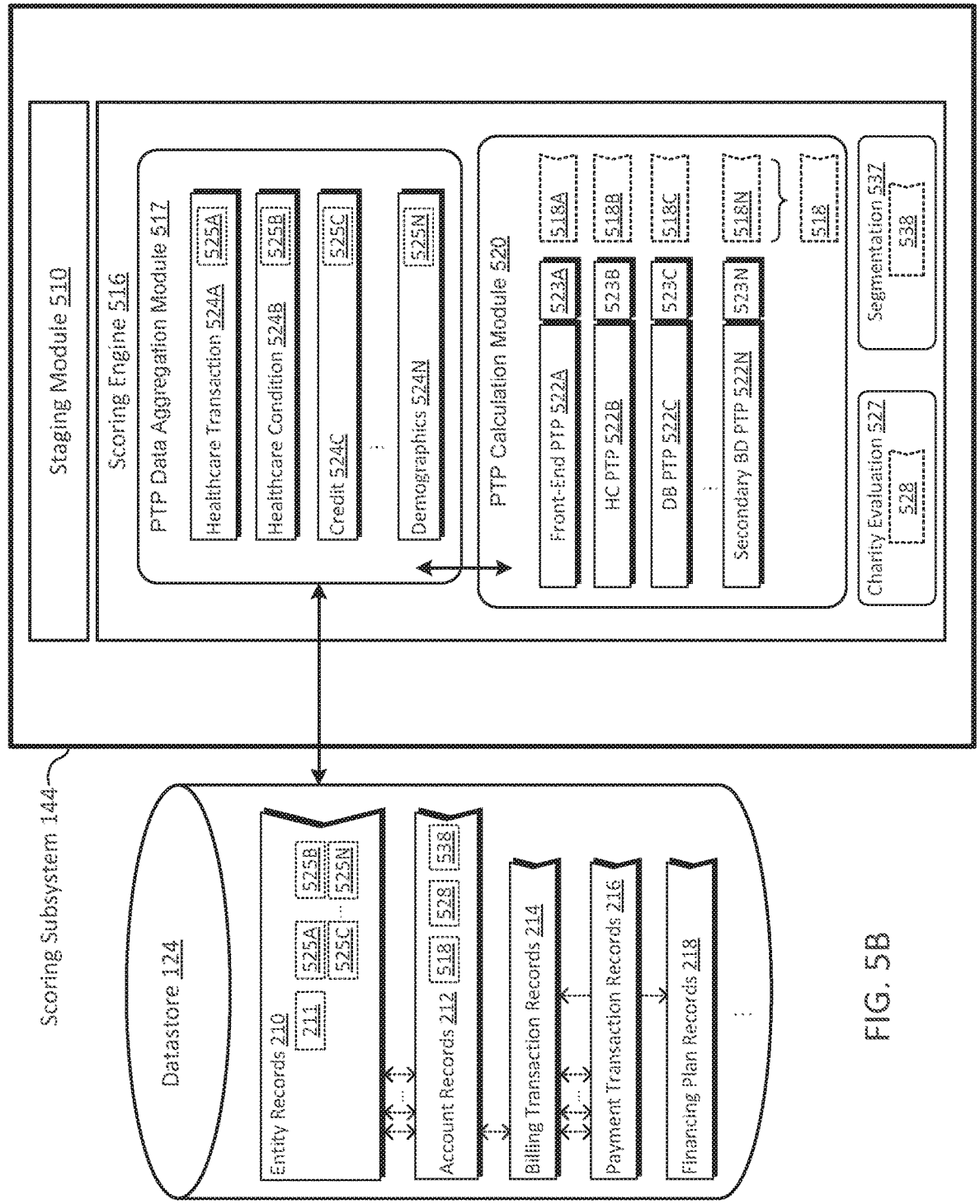
FIG. 5B is a block diagram of a scoring subsystem of a payment management system, according to another embodiment.

FIG. 5B is a block diagram of another embodiment of a scoring subsystem 144, comprising a scoring engine 516. The scoring engine 516 may include a PTP calculation module 520 configured to calculate PTP scores 518 (scores 518A-N) for account records 212 by use of data pertaining to the patient and/or guarantor(s) corresponding to the account records 212. The scoring engine 516 may include a PTP data aggregation module 517 configured to access and/or derive the PTP data 525A-N for use by the PTP calculation module 520 to generate the PTP score(s) 518. The PTP data aggregation module 517 may be configured to access PTP data 525A-N extracted from the data sources 116A-N by the extraction engine 122, as disclosed above. Accordingly, the PTP data aggregation module 517 may be configured to aggregate PTP data 525A-N from the contents of the datastore 121 (e.g., from records 210, 212, 214, 216, and/or 218). Alternatively, or in addition, the PTP data aggregation module 517 may be configured to request data from the data stores 116A-N (using the data source adapters 123A-N of the extraction engine 122) to access data as needed and/or in real time.

The PTP data aggregation module 517 may include one or more PTP data aggregation engines 524A-N configured to aggregate particular types of PTP data 525A-N. The PTP data aggregation module 517 may include, but is not limited to, a healthcare transaction data aggregation engine 524A, a healthcare condition data aggregation engine 524B, a credit data aggregation engine 524C, a demographics data aggregation engine 524N, and so on. The healthcare transaction data aggregation engine 524A may be configured to derive historical healthcare transaction data 525A from a history of billing transaction records 214, payment transaction records 216, and/or financing plan records 218 associated with the account record 212. The healthcare transaction data 525A may include and/or be derived from billing transaction records, payment transaction records, and/or financing plan records associated with account records of one or more guarantors. The historical healthcare transaction data 525A may include PTP characteristics of guarantors, which may include, but are not limited to, time to payment for healthcare transactions, late payments, payment amounts, insurance coverage, copayments, flexible spending account activity (e.g., estimated remaining balance), healthcare spending account activity, financing plan history (e.g., whether the patient and/or guarantor(s) have used a financing plan to pay for services and/or whether the payments were made in a timely manner), and so on.

The healthcare condition data aggregation engine 524B may be configured to acquire information pertaining to a healthcare condition and/or status of the patient and/or guarantor(s) associated with the account record 212. The healthcare condition data 525B may include, but is not limited to, diagnoses, disease conditions, chronic health condition(s), degenerative conditions, and/or the like. In some embodiments, the healthcare condition aggregation engine 524B is configured to derive healthcare condition data 525B from billing transaction information acquired from the billing data sources 116A (e.g., treatment codes, diagnostic codes, and/or the like). Alternatively, or in addition, healthcare condition data 525B may be acquired from a healthcare data source 116B (e.g., directly from healthcare records of the patient and/or guarantor(s)).

The credit data aggregation engine 524C may be configured to aggregate credit reporting data 525C pertaining to the patient and/or guarantor(s) of the account record 212. The credit reporting data 525C may be acquired and/or derived from one or more credit data sources 116C, as disclosed above.

The demographics data aggregation engine 524N may be configured to aggregate demographics data 525N pertaining to the patient and/or guarantor(s) of the account record 212. The demographics data 525N may be acquired and/or derived from one or more demographics/consumer data sources 116N, as disclosed above.

As illustrated in FIG. 5B, in some embodiments, the PTP data aggregation module 517 may be further configured to store PTP data 525A-N pertaining to the account records 212 (and/or individual patients and/or guarantors) in the datastore 121. The data aggregation engines 524A-N of the PTP data aggregation module 517 may update and/or modify the stored data 525A-N rather than rebuilding the aggregated PTP data 525A-N each time PTP scores 518 are generated.

The PTP calculation module 520 may be configured to determine which PTP score(s) 518A-N are to be calculated, and to request corresponding PTP data 525A-N from the PTP data aggregation module 517. The PTP calculation module 520 may select a type of PTP score(s) 518A-N to calculate based on, inter alia, the stage assigned to the account record 212, data availability, a request for a particular type of PTP score 518A-N, and/or the like.

As illustrated in FIG. 5B, the PTP calculation module 520 may comprise one more calculation engines 522A-N, each of which may be configured to calculate a respective type of PTP score 518A-N for guarantor(s). The PTP scores 518A-N may correspond to particular account stages, as disclosed above. The PTP calculation module 520 may include, but is not limited to: a front-end PTP engine 522A configured to calculate front-end PTP scores 518A, an HC PTP engine 522B configured to calculate HC PTP scores 518B, a BD PTP engine 522C configured to calculate BD PTP scores 518C, a second BD PTP engine 522N configured to calculate secondary BD PTP scores 518N, and so on. PTP scores 518A-N may be calculated for particular patients and/or guarantor(s). The PTP associated with an account record 212 may, therefore, correspond to PTP scoring information of the patient and/or guarantor(s) corresponding to the account record 212.

The front-end PTP engine 522A may be configured to calculate a front-end PTP score 518A for a guarantor based on, inter alia, a) credit reporting data 525C and/or b) demographics data 525N. The front-end PTP score 518A may correspond to the PTP of a patient and/or guarantor(s) independent of healthcare transaction history and/or characteristics. The front-end PTP score can be used to guide front-end staff of an appropriate collection tactic at the scheduling/registration of a patient before any services have been provided. For example, the front-end PTP score may guide how much a patient/guarantor may be required to pay in advance or "arrange in advance" of receiving a treatment. The front-end PTP score may be generated for an estimate of charges for healthcare services to be performed. The front-end PTP score may be based on and/or integrate preferences of the provider in terms of matching front-end tactics according to such variables as type of treatment (emergent vs. scheduled and medically necessary vs. scheduled and elective), past payment behavior, prior discounts, balance range, etc. Recommended collection tactics may include an amount of cash payment to require prior to providing treatment, authorization for financing options, and the like. The front-end PTP score may allow creation of a financing plan and payment authorization structure at time of service that would not be ratified until after an insurance claim is adjudicated and a patient balance is known. For example, if the estimate is $2,000, in order to proceed the patient may be required to establish an account in the payment management system 102 and agree to a 10-month loan at $200 per month. As another example, for maternity care, a patient may be required to funding a deposit balance (e.g., $300 per month for nine months) to fund the arrival of the baby and associated medical bills. The deposit account balance may be tracked by an account in the payment management system 102.

The HC PTP engine 522B may incorporate the data of the front-end PTP score 518A (credit reporting data 525C and/or demographics data 525N) as well as historical healthcare transaction data 525A and/or healthcare condition data 525B. The HC PTP score 518B may, therefore, indicate a PTP based on historical healthcare payment activity of the patient and/or guarantor(s) and/or conditions affecting the patient and/or guarantor(s).

The BD PTP engine 522C may be configured to calculate a BD PTP score 518C incorporating data 525A-N, and may include activity that has occurred during the AR cycle (e.g., partial payments, additional debt accrued, updated historical healthcare transaction data 525A, updated healthcare condition data 525B, updated credit reporting data 525C, updated demographics data 525N, and so on).

The secondary BD PTP engine 522N may calculate a secondary BD PTP score 518N based on further updates during bad debt recovery.

The PTP calculation engines 522A-N may incorporate similar sets of data (data 525A-N) to generate the PTP scores 518A-N. The PTP calculation engine 522A-N may differ with respect to the weighting and/or combination of algorithms used to calculate the PTP scores 518A-N. In some embodiments, the PTP calculation engines 522A-N are configured to calculate PTP scores 518A-N by use of respective regression analysis models 523A-N. The regression analysis models 523A-N may comprise PTP statistical modeling data pertaining to sets of account records 212 (e.g., accounts in particular stages 0-4). The regression analysis models 523A-N may, therefore, correspond to different variable and/or data weighting values for the PTP data 525A-N based on, inter alia, statistical estimation and/or modeling processes within the respective account record sets. Accordingly, the PTP scores 518 generated by the PTP engines 522A-N may differ significantly despite incorporating similar sets of PTP data 525A-N.

The PTP scores 518A-N may be provided to a client provider billing system and/or presented to a provider via an interface, such as the graphical user interface of the client input subsystem 162 of FIG. 1. Personnel or staff of a client provider may be enabled to trigger or otherwise request generation of the PTP scores 518A-N for use in registering patients and in other interactions with patients and/or guarantors to improve collection of payment for services rendered by the provider. In other embodiments, other PTP metrics may be generated and provided to a client provider billing system. For example the scoring subsystem may generate a guarantor segment (or group) identifier that may indicate a segment, group, classification, category, or the like, in which the guarantor belongs. A propensity-to-pay may be associated with the metric (e.g., a guarantor grouping) and thereby may indicate collection or other servicing strategies for the guarantor and/or may be used to determine financing terms, similar to how a PTP score can be used.

Described differently, servicing strategies and or financing terms may be associated with a guarantor grouping such that the associated strategies and financing terms may be known to apply to guarantors that are within the guarantor grouping. The provider can use a segmentation (or group) identifier to either establish rules and policies within the billing system for dictating the nature of allowed payment alternatives and financing plans or terms, and also indicate suggested servicing strategies. Similarly, the payment management system 102 can use a segmentation (or group) identifier to establish similar rules and policies, dictate payment alternatives and financing plans or terms, and determine suggested servicing strategies.

In some embodiments, the scoring subsystem 144 may further include a charity evaluation module 527. The charity evaluation module 527 may be configured to identify account records 212 that are candidates for presumptive charity (write-off). The charity evaluation module 527 may be configured to identify presumptive charity candidates in response to account records 212 that satisfy charity conditions. In some embodiments, the charity evaluation module 527 is configured to calculate a charity score 528 for an account record 212, which may be based on, inter alia, one or more PTP scores 518 corresponding to the account record 212 (e.g., BD PTP score 518C) and an ability-to-pay metric that includes, but is not limited to, the amount owed as indicated by the historical healthcare transaction data 525A, the condition of the patient and/or guarantor(s) as indicated by the healthcare condition data 525B, debt level as indicated by the credit reporting data 525C, income level as indicated by the demographics data 525N, and so on. The charity evaluation module 527 may be configured to compare the charity score 528 to a predetermined threshold to determine whether the corresponding account is suitable for presumptive charity. As illustrated in FIG. 5B, the charity score 528 and/or a corresponding indication of whether the account record 212 is a presumptive charity candidate may be maintained in the datastore 121.

In some embodiments, the charity evaluation module 527 is configured to determine charity eligibility based on demographic characteristics of the patient and/or guarantor (e.g., income estimate, size of household, and/or the like). The demographic characteristics may be compared against poverty guidelines (e.g., Federal Poverty Level) and/or hospital policy to identify accounts that fall within the client providers' policies for charity relief (e.g., 0%, 50%, 80% or 100% of poverty-level cases). PTP scores 518A-N associated with the guarantor(s) may be used to rank the identified accounts to determine an actual distribution of charity. Charity distributions may, therefore, be made to guarantors that are both a) eligible for charity according to the demographic characteristics disclosed above, and b) are least likely to be able to pay according to the corresponding PTP scores 518. The charity evaluation module 527 may be further configured to hold out samples of charity eligible accounts that do not receive charity in order to, inter alia, calculate an optimal point in a charity allocation curve where the foregone collection opportunity on charity accounts is optimized for the community benefit of classifying an impaired asset as presumptive charity rather than bad debt. A charity guideline may be adjusted using the PTP scores 518 in accordance with a specific charity target or budget (while optimizing AR and charity account selection). As previously noted, the PTP scores 518 may be determined based solely on historical transaction data tracked in a billing system (e.g., billing transaction records 214, payment transaction records 216, and financing plan records 218), and without third-party data (e.g., credit reporting data 525C).

The scoring subsystem 144 may further comprise a segmentation engine 537 configured to determine a segment classification 538 for the account record 212. The segment classification 538 may be used by other tiers, modules, components, and/or engines of the payment management system 102 to manage the account record 212. The segmentation module 537 may be configured to assign segment classifications based on, inter alia, the stage assigned to the account records 212 and/or the PTP score(s) 518 of the account records 212. The segment classifications may include, but are not limited to, high risk, moderate risk, low risk, delayed payment, on-time payment, and/or the like. The segment classifications may be used to determine contact and/or billing procedures for account records 212, such as contact frequency, contact type, financing plan characteristics (e.g., whether the account record 212 is eligible for a financing plan and/or the terms of the financing plan), interest rates for financing plans, and/or the like. The segmentation classifications 538 may be based on a statistical distribution of the PTP scores 518, regression analysis, and/or the like. The segmentation classification 538 of the account record 214 may be maintained in the datastore 121, as illustrated in FIG. 5B. The segmentation classification 538 may be communicated to the client provider billing system(s) from which the healthcare transaction data 524A originated. The segmentation classification 538 may also be communicated to personnel of the client provider, such as via a graphical user interface. The segmentation classification 538 may be communicated in addition to, or in lieu of, the PTP score(s) 518.

Referring back to FIG. 4, the forecast engine 416 of the business intelligence subsystem 142 may be configured to generate forecasts 419 based on, inter alia, the PTP scoring data 518 generated by the scoring subsystem 144. The forecasts 419 may correspond to forecasted AR activity pertaining to the account records 212 (e.g., forecast incoming payment transaction records 216). Accordingly, the forecast engine 416 may generate the forecasts 419 based on the probability that particular account records 212 will be paid and/or when payments for the particular account records 212 will be received. Accordingly, the forecast engine 416 may be configured to calculate both a) probability of payment, and b) timing for the payment. As disclosed above, the PTP score(s) 518 assigned to the account records 212 may correspond to payment probability. The PTP score(s) 518 may further include information pertaining to an estimated time to pay (e.g., the PTP metrics of the PTP scores 518 may correspond to both PTP and payment delay). Alternatively, or in addition, the forecast engine 416 may calculate payment timing estimates 418 for account records 212 independently based on, inter alia, the PTP score(s) 518, historical healthcare transaction data 525A, healthcare condition data 525B, credit reporting data 525C, and/or demographics data 525N, disclosed above. The time-to-pay estimates may be based on a regression analysis modeling using, inter alia, the PTP score(s) 518 and/or segment classification(s) 538 calculated by the scoring subsystem 144.

Determining an accounts receivable forecast 419 may comprise scaling the payments owed under a set of account records 212 by respective PTP score(s) 518 of the account(s) and/or estimating a payment time of the accounts based on the time-to-pay estimates, disclosed above. The PTP score(s) 518 used to generate the forecasts 419 may be selected in accordance with the stage assigned to the respective account records 212 by the staging module 510.

The forecast engine 416 may be configured to generate forecasts 419 pertaining to particular aspects of the payment management system 102 including, but not limited to, forecasts 419A for particular time frames, forecasts 419B for particular billing entities (e.g., particular hospitals, clinics, service providers, and/or the like), forecasts 419N for particular billing locations, and/or the like. Generating a timeframe forecast 419A may comprise estimating accounts receivable activity on all outstanding account records 212 based on corresponding PTP score(s) 518 and/or time-to-pay estimates, as disclosed above. Generating a billing entity forecast 419B may comprise a) identifying a set of billing transaction records 214 corresponding to a particular billing entity, and b) calculating an accounts receivable forecast 419 based on PTP and/or time-to-pay metrics of the corresponding account records 212, as disclosed above. Generating a location forecast 419N may comprise a) identifying a set of billing transaction records 214 corresponding to a particular location, and b) calculating an accounts receivable forecast 419B based on PTP and/or time-to-pay metrics of the corresponding account records 212, as disclosed above. Although exemplary forecasts 419 are described herein, the disclosure is not limited in this regard and could be adapted to generate forecasts pertaining to billing transaction records 214 and/or account records 212 selected and/or filtered based on any suitable criterion (e.g., demographics, insurance type, socio-economic level, segment classification 538, and so on).

Figure 6A:
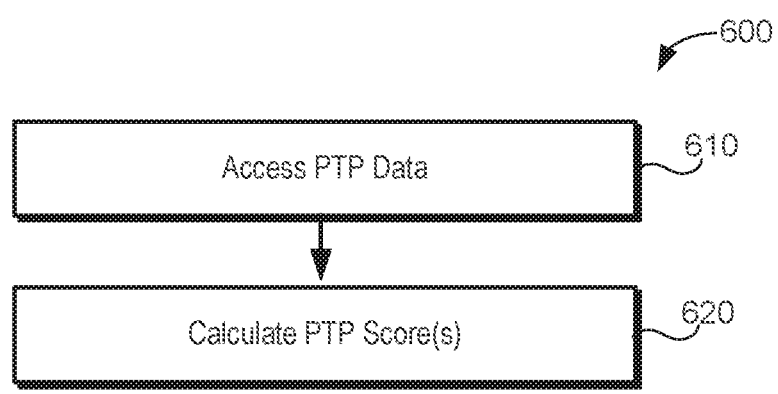
FIG. 6A is a flow diagram of a method of generating propensity-to-pay scoring data, according to one embodiment.

FIG. 6A is a flow diagram of one embodiment of a method 600 for generating PTP scoring data. Step 610 may comprise accessing and/or aggregating data from one or more data sources 116A-N. The PTP data may include, but is not limited to: historical healthcare transaction data 525A, healthcare condition data 525B, credit reporting data 525C, demographics data 525N, and/or the like.

Step 620 may comprise calculating a PTP score 518 for an account record 212 by use of the PTP data 525A-N of step 610. Step 620 may comprise extracting PTP characteristics from the PTP data 525A-N, weighting the extracted characteristics, and/or combining the weighted characteristics to calculate one or more PTP score(s) 518, as disclosed above. The PTP characteristics may include time to payment for healthcare transactions, late payments, payment amounts, insurance coverage, copayments, flexible spending account activity (e.g., estimated remaining balance), healthcare spending account activity, financing plan history (e.g., whether the patient and/or guarantor(s) have used a financing plan to pay for services and/or whether the payments were made in a timely manner), a total amount presently owed to a provider (or one or more client providers), prior bad debt charge-offs, prior hardship program assistance (charity), time periods between transactions, and dispute history.

In some embodiments, step 620 further comprises determining a stage associated with the account record 212. As disclosed above, stage assignments may be based on account and/or billing transaction events, such as account creation, billing adjudication, self-pay, split balance, bad debt, secondary bad debt, and/or the like. Step 620 may comprise calculating a particular PTP score 518A-N based on the assigned stage. Accordingly, step 620 may comprise calculating one or more of a front-end PTP score 518A, an HC PTP score 518B, a bad debt PTP score 518C, a secondary bad debt PTP score 518N, and/or the like.

In certain embodiments, one or more of the PTP score(s) 518 calculated at step 620 incorporate historical healthcare transaction data 525A pertaining to the patient and/or guarantor(s). The one or more PTP score(s) 518 may, therefore, incorporate characteristics and/or metrics that are specific to healthcare transactions of the patient and/or guarantor(s). Such characteristics may include, but are not limited to, historical payment amounts, historical time to payment, bad debt (if any), secondary bad debt (if any), payment types, payment relationships (e.g., guarantor on other healthcare transactions), and/or the like.

In certain embodiments, one or more of the PTP score(s) 518 calculated at step 620 incorporate information pertaining to a health condition of the patient and/or guarantor(s). As disclosed above, information pertaining to health condition(s) of the patient may be derived from billing transaction information provided by the billing data source(s) 116A. The health condition(s) may be determined based on condition and/or diagnosis coding information in the billing information. The health condition(s) of the guarantor (if different from the patient) may be determined based on separate billing transaction information obtained from one or more other healthcare billing data sources 116A (e.g., other patient visits, diagnosis, and/or the like). Alternatively, or in addition, information pertaining to the health condition of the patient and/or guarantor(s) may be obtained from a separate healthcare data source 116B. The health condition of the patient and/or guarantor(s) may be used to determine payment probability and/or timing (patients with serious conditions may not be in a position to pay in a timely manner).

Step 620 may further comprise calculating a charity score 528 for the account record 212, which, as disclosed above, may be used to identify accounts that are candidates for write-off (presumptive charity). Step 620 may further comprise assigning a segment classification 538 to the account record 212, as disclosed above.

Figure 6B:
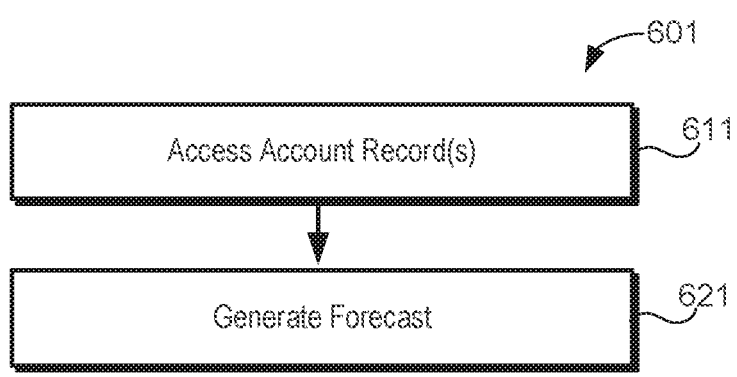
FIG. 6B is a flow diagram of a method for accounts receivable forecasting, according to one embodiment.

FIG. 6B is a flow diagram of one embodiment of a method 601 for accounts receivable forecasting. Step 611 may comprise accessing a set of account records 212. The account records accessed at step 611 may be selected according to a selection criterion, such as time frame, billing entity, billing location, service provider, location, patient type, and/or the like. Accordingly, step 611 may comprise filtering the account records 212 to identify account records 212 that conform to one or more of the criteria.

Step 621 may comprise generating a forecast corresponding to accounts receivable activity pertaining to the set of account records 212 accessed at step 611. Step 611 may comprise determining a likelihood of payment transactions on the set of accounts during a particular time period (and/or whether any payment will be received). The forecast of step 621 may incorporate a) PTP score(s) 518 of the account records 212 and/or b) time-to-pay estimates of the account records 212. The time-to-pay estimates may be derived from PTP score(s) 518 of the account records 212 and/or PTP data 525A-N, as disclosed above.

Public Payment Portal Subsystem

Figure 7:
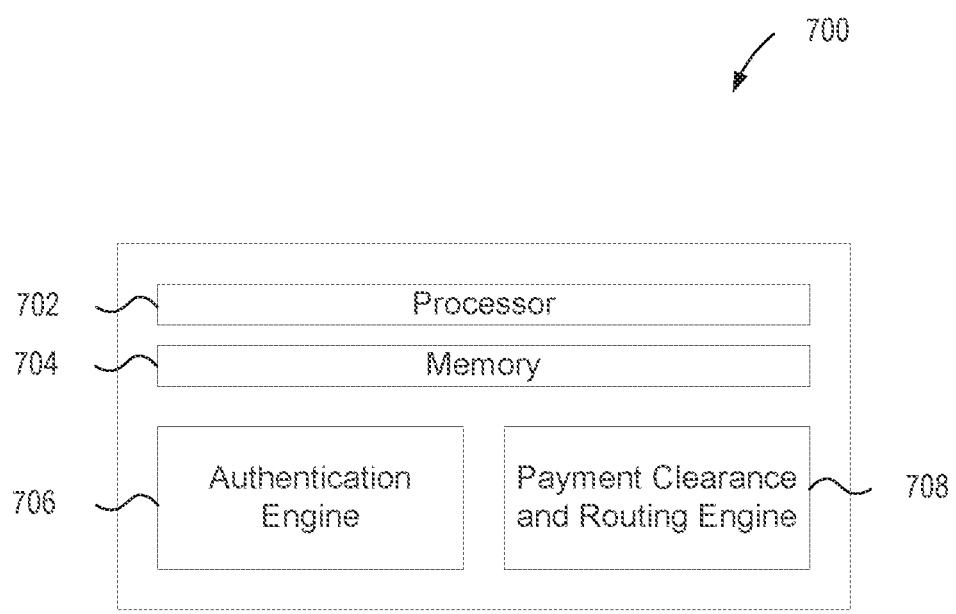
FIG. 7 is a block diagram of a public payment portal subsystem of a payment management system, according to one embodiment.

FIG. 7 is a block diagram of a public payment portal subsystem 700 of a system for managing payments for healthcare services, according to one embodiment. The public payment portal subsystem 700 includes a processor 702 (or more than one processor 702), a memory 704, an authentication engine 706, and a payment clearance and routing engine 708. The public payment portal subsystem 700 can facilitate payments from a guarantor with obligations on any one of multiple billing systems that a client provider may use. As noted, a client provider may employ multiple different billing systems for different aspects of its business. The public payment portal subsystem 700 enables a single guarantor interface for any of the different billing systems. The public payment portal subsystem 700, in combination with a guarantor input subsystem, can provide a uniform interface at which guarantors can interface with multiple billing systems of a client provider. The public payment portal subsystem 700 further posts transactions automatically to the respective billing system without a need for manual intervention. If a received payment cannot be matched to a guarantor account, an exception file may be created and introduced to a work queue, such as a mismatched records work queue, for the client provider to manually search accounts and match payments accordingly.

The authentication engine 706 may interface with the datastore 121 of FIG. 1 to obtain guarantor data and visit data and/or visit charge data. The visit charge data may be extracted or otherwise received from a client provider billing system. A unique identifier may be included with the data that can be used by the guarantor to authenticate access into the public payment portal subsystem 700. The authentication engine 706 may use the unique identifier to coordinate which visit charges are to be paid by a guarantor.

The payment clearance and routing engine 708 may coordinate transaction authorization and payment processing. The payment clearance and routing engine 708 may interface with a payment gateway that facilitates and/or coordinates payment from the guarantor's financial institution and the client provider's financial institution. The payment clearance and routing engine 708 may also coordinate communication to the billing system when a payment transaction is completed or otherwise effectuated.

Figure 8:
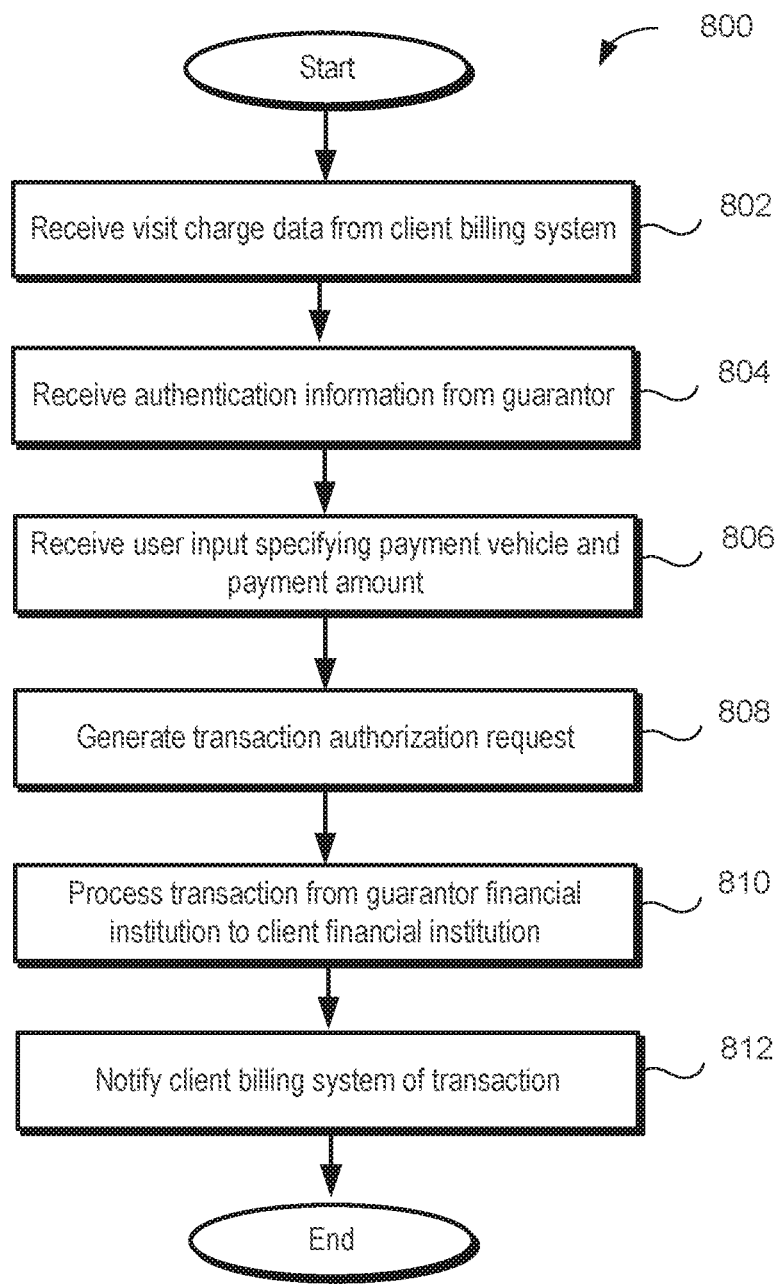
FIG. 8 is a flow diagram of a method of processing payments, according to one embodiment.

FIG. 8 is a flow diagram of a method 800 of processing payments, according to one embodiment. Visit charge data is received 802 from a billing system. The visit charge data may be extracted by an extraction engine or may be pushed from the billing system. The visit charge data that is received 802 may include a charge amount, a patient name, a guarantor name, and a unique identifier that may correspond to the charge for the visit. The unique identifier may be a statement identifier. The guarantor that wishes to make a payment via the public payment portal subsystem may provide authentication information. The authentication information is received 804 to coordinate which charges are being paid. The authentication information may include the unique identifier. The authentication information may also include other information such as the patient name, guarantor name, and/or an identifier of such individual or entity (e.g., an SSN or portion thereof).

Once authentication information is received 804 that corresponds to the received 802 visit charge data, the user may be able to specify a payment vehicle and amount. User input is received 806 specifying the payment vehicle (e.g., the guarantor's credit card, debit card, bank account, Health Savings Account, or the like) and specifying a payment amount. A financial transaction authorization request is generated 808. The transaction is processed 810 between the guarantor financial institution and the client provider financial institution. The processing 810 may be facilitated and/or performed by a payment gateway. Authorization for the transaction may be granted and thus received in response to the transaction authorization request. Alternatively, confirmation of the transaction may be received. Once the transaction has been completed or otherwise effectuated, the billing system may be notified 812 of the transaction. The notification may occur by generation of a transaction posting file that may be transmitted to the billing system.

The payment posting files may include, but are not limited to, the following: an identifier (e.g., a billing system assigned identifier at a charge level, at the visit charge level, or at the guarantor level), a transaction amount (e.g., a positive or negative amount that may include multiple fields for principle, interest, commission, etc.), a transaction code to define the type of transaction (e.g., patient payment, prompt-pay discount adjustment, interest charged, interest paid, etc.), a reference number (e.g., a field which can be loaded along with the payment and extracted again to load back to the payment management system for use in identifying which payments have or have not yet been posted back into a billing system), a transaction date, and a text note (e.g., text to be shown in the user interface of the billing system).

The public payment portal subsystem may enable receiving and/or configuring instructions to make recurring payments (e.g., configure financing plans) to pay for visit charges. For example, the patient/guarantor could decide to make four payments (e.g., $250 each on a $1,000 obligation) and schedule each of those payments to occur on a periodic basis (e.g., monthly) over four months. An anonymous unique transaction authorization identifier (e.g., a token received from a third-party gateway) may be received and stored. The anonymous unique transaction authorization identifier or a similar token could then be presented again to the gateway in the ensuing months to effectuate the recurring transactions.

Guarantor Input Subsystem

FIG. 9 illustrates a user interface 900, according to one embodiment, of a guarantor input subsystem. The guarantor input subsystem may be the guarantor input subsystem 164 of the payment management system 102 of the system 100 of FIG. 1. The guarantor input subsystem 164 enables interfacing with the public payment portal subsystem 146 and/or the private payment portal subsystem 148 of FIG. 1.

The user interface 900 of FIG. 9 illustrates private user access in which the guarantor input subsystem interfaces with the private payment portal subsystem to enable access and/or presentation of PHI. Private user access interfacing with the private payment portal subsystem may require user login and password information. Upon login, the user interface 900 may display to provide a viewing guarantor with an overview of the guarantor's account and/or any accounts managed by the guarantor. As briefly mentioned above, and explained more fully below with reference to FIGS. 17 and 18, the private payment portal subsystem may generate and provide to a guarantor an electronic statement for a given period (e.g., a one-month statement period), configure statement preferences (e.g., statement date and/or due date), configure automatic transactions (e.g., payment date, payment method), pay new charges for visits that occurred during the statement period, finance and/or configure a new financing plan for new visits from the current statement period, consolidate billing by agreeing to manage the account of another guarantor (e.g., consolidate household billing by managing a spouse's account), add visits the guarantor believes should be reflected in the guarantor's account but were previously unmatched due to a variety of issues (e.g., data input error, incomplete data, typographical error), and view past transaction data. The user interface 900 may provide an interactive overview of an electronic statement that may include an account overview area 902, an autopay overview area 904, a payment options area 906, and an account summary area 908.

The account overview area 902 displays a brief overview of a current balance on the account (including all managed accounts), a statement balance (including all managed accounts), a next payment date, and a next statement date.

The autopay overview area 904 displays information relating to payments (or amounts of money) that are pending to be automatically deducted from a preconfigured payment vehicle (e.g., the guarantor's credit card, debit card, bank account, or Health Savings Account) or according to a preconfigured payment methodology for existing financing plans as well as preset payment arrangements for current statement charges.

The payment options area 906 displays options for paying for health services rendered during new visits (or visits pertaining to a current statement period). The payment options may include paying the current visits balance in full to potentially receive a discount. The discount may be configured by the client healthcare provider that provided the healthcare services to the patient. The payment options may also include an option to finance payment for healthcare services rendered during new visits for the current statement period. The user interface 900 may enable the guarantor to configure financing terms that may better fit a budget of the guarantor or otherwise be more workable for the guarantor to successfully pay in full, or over time, for the charges for the healthcare services rendered for the visits. The user interface 900 may also indicate preset financing terms which may be accepted by the guarantor. The user interface 900 may be configured to indicate automatic acceptance of the preset financing terms if another payment option is not selected. The preset financing terms may be preconfigured, for example, by the client healthcare provider. The illustrated user interface 900 of FIG. 9 indicates that the preset (or standard) financing terms are four months at 0.00% interest.

The account summary area 908 displays information summarizing a current status of the account, including a summary of the current statement period and a summary of recent activity.

A "Statements" link 910 is provided on the user interface 900 to enable the logged in guarantor to access an electronic statement of the guarantor's account. A "My Visits" link 912 is provided on the user interface 900 to enable the guarantor to access and view information about visits included or otherwise associated with the account of the guarantor or with an account managed by the guarantor. A "My Financing" link 914 is provided on the user interface 900 to enable the guarantor to access information pertaining to financing plans that the guarantor has taken out to finance payment for healthcare services. A "My Payment History" link 916 is provided on the user interface 900 to enable the guarantor to access information pertaining to payments the guarantor has made in direct payment for healthcare services rendered or in payment toward financing plan balances for financing plans taken out to finance payment for healthcare services.

The user interface 900 also includes a manage account tab 920, a payments and financing tab 922, and a support tab 924. The manage account tab 920 enables a guarantor to access account management tools and/or functionality, such as viewing and/or modifying personal information, accessing account statements, accessing information about visits, and managing a household (e.g., linked accounts). The payments and financing tab 922 enables a guarantor to access information relating to payments of the guarantor and financing plans the guarantor may have taken out to finance payment for healthcare services. The information may include a listing of financing plans, a listing of payment methods, pending payments (e.g., automatic transactions that are scheduled), and a payment history. Functionality may also be provided on the payments and financing tab 922 to review (e.g., forensically "trace") where a given payment was applied (e.g., to which billing system accounts, visits, and visit charges). The support tab 924 enables a guarantor to access support information.

As noted above, the user interface 900 of FIG. 9 provides private user access in which the guarantor input subsystem interfaces with the private payment portal subsystem to enable access and/or presentation of PHI.

The user interface 900 of FIG. 9 may also provide a linking indication 926 to indicate accounts that may be linked to the guarantor's account, and more specifically to indicate accounts the guarantor may be managing.

Private Payment Portal Subsystem

Figure 10:
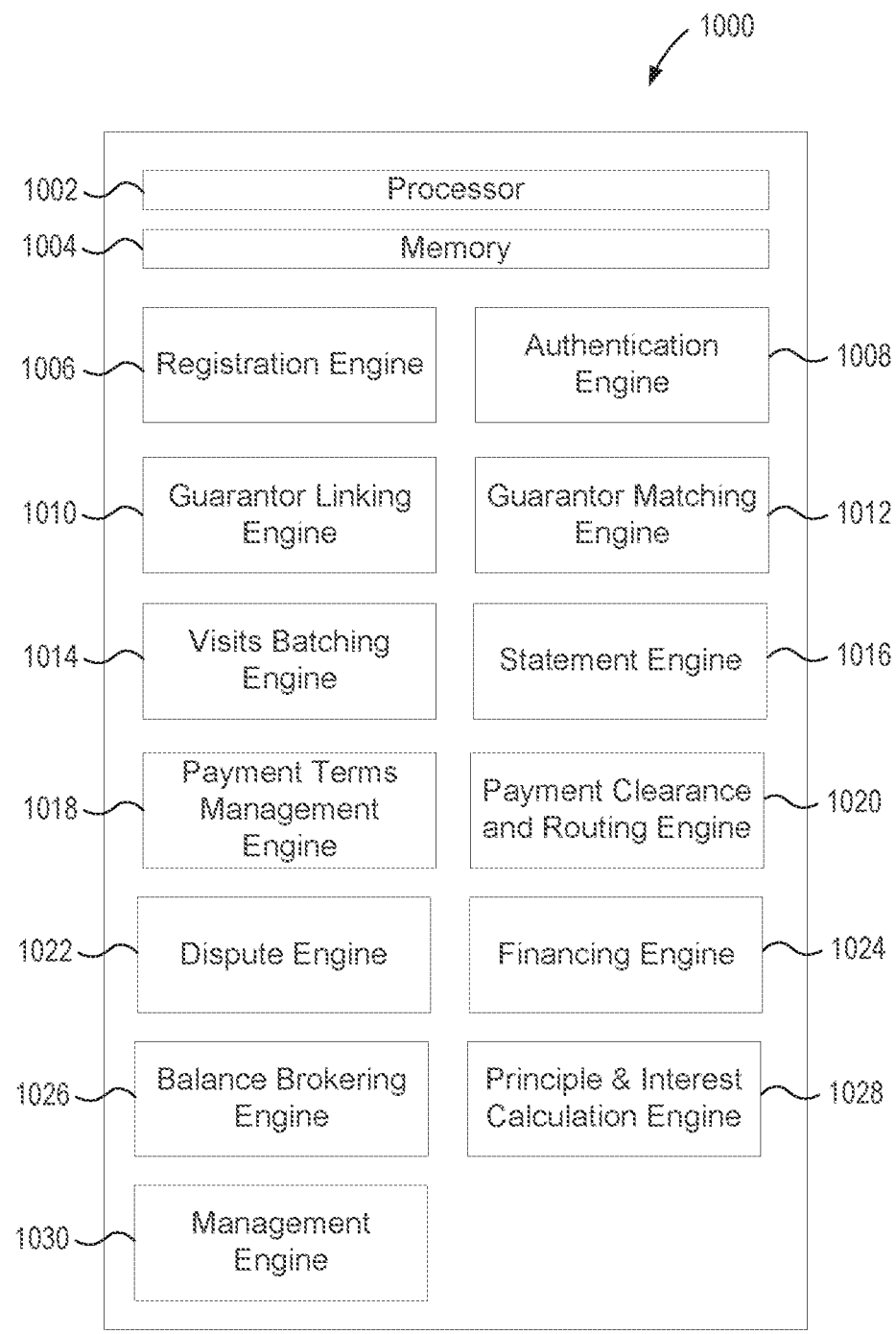
FIG. 10 is a block diagram of a private payment portal subsystem of a payment management system, according to one embodiment.

FIG. 10 is a block diagram of a private payment portal subsystem 1000 of a payment management system, according to one embodiment. The private payment portal subsystem 1000 includes a processor 1002 (or one or more processors), a memory 1004, a registration engine 1006, an authentication engine 1008, a guarantor linking engine 1010, a guarantor matching engine 1012, a visits batching engine 1014, a statement engine 1016, a payment terms management engine 1018, a payment clearance and routing engine 1020, a dispute engine 1022, a financing engine 1024, a balance brokering engine 1026, a principle and interest calculation engine 1028, and a management engine 1030.

The registration engine 1006 provides functionality to enable a guarantor to register for access to the private payment portal subsystem 1000. The registration engine 1006 receives information for guarantors and pre-approval or acceptance of registration from a client provider. The information for guarantors may be received and stored in a patient/guarantor database in the datastore 121 of FIG. 1. The pre-approval and/or information for the guarantors may be obtained from a database in the datastore 121.

The authentication engine 1008 may receive user login and password information and authenticate a guarantor, to confirm the guarantor is registered, before allowing access to the private payment portal subsystem 1000 and PHI accessible therethrough. The authentication may access registered guarantor information extracted from, for example, a billing system and stored in a database in the datastore 214. The authentication engine 1008 may also perform more rigorous authentication, for example, at registration or at login. For example, the authentication engine 1008 may cross check guarantor information with third-party data sources to perform identity verification (e.g., looking for one or more matches to a name, address, SSN, email, etc.) or alternatively offering multifactor authentication.

The guarantor linking engine 1010 may provide functionality for linking accounts. For example, a first guarantor may request a second guarantor to manage the first guarantor's account (e.g., a request to be managed), or the first guarantor may request to manage the second guarantor's account (e.g., a request to manage). The guarantor linking engine 1010 enables a first guarantor to request or assign (and a second guarantor to accept) managerial responsibilities for the first guarantor's account. The second guarantor, upon accepting managerial responsibilities, accepts financial responsibility for the account and/or obligations of the first guarantor (or managed guarantor). The guarantor linking engine 1010 may also enable either party to sever a linkage at any time, such that the formerly managed guarantor (e.g., the first guarantor) again assumes responsibility for all past and current obligations. The guarantor linking engine 1010 implements and facilitates ensuring any necessary permissions and releases are properly executed, managed, and/or stored.

The guarantor matching engine 1012 may identify orphan, unmatched, or otherwise unassociated accounts (e.g., including charges, payments, and other obligations and/or transactions) within and across one or more billing systems for a guarantor. Described differently, the guarantor matching engine 1012 can identify unmatched accounts in a billing system that should be associated with a guarantor account record in the payment management system, can determine the guarantor account those unmatched billing system accounts should be associated with, and can associate those unmatched billing system accounts to the appropriate guarantor account record in the payment management system. The guarantor matching engine 1012 may utilize a matching algorithm that may use or otherwise consider, for example, one or more of: a name of the patient or guarantor on the unmatched transaction, at least a portion of an ID number (e.g., an SSN, driver's license), a date of birth, and an address. Once the match or association is made, the formerly unmatched accounts may be tracked in this associated format even if the originating billing systems do not realize these accounts should be tied to the same guarantor and are not properly associated in the billing system itself. The guarantor matching engine 1012 may allow a guarantor to match an account in a billing system that the guarantor may be aware of, such as by receiving a paper billing statement from a billing system of the client healthcare provider. The visit and/or corresponding visit charges may belong to the current guarantor (or a currently managed guarantor), but may reside in a different billing system of the client provider from other visits and corresponding visit charges that are properly reflected on the electronic statement. The account of the guarantor within the different billing system may be unmatched to the account of the guarantor associated with the electronic statement. The account matching functionality that is provided by the guarantor matching engine 1012 enables the guarantor to locate the missing visit data and match the associated billing system account with the guarantor's account corresponding on the payment management system. Once an unmatched account in a billing system is associated with a guarantor account in the payment management system (either through matching logic or if the user manually links an otherwise orphan account), that association persists even though the billing system itself may not recognize the relationship. In other words, the billing system may not be updated based on the matching process. The billing system tracking remains independent of the payment management system tracking.

The visits batching engine 1014 may associate all visits for a given guarantor (or group of linked guarantors) during a specific period of time (e.g., monthly) and present this aggregated pool of obligations as a batch of open charges and/or an open charges balance for payment or for financing. The visits batching engine may compile visit data and/or visit charge information for the statement engine 1016.

The statement engine 1016 may gather visit data and/or visit charge data to generate and provide electronic statements. The statement engine 1016 may also enable a guarantor to view a listing of the visits associated with his account, sort them, filter them, understand how payments were applied to principal or interest, etc. The statement engine 1016 may also enable a user to drill down on a visit to view more detailed information. The statement engine 1016 may also present functionality (e.g., a link or button) to enable a guarantor to access the dispute engine 1022 to dispute a visit charge on the electronic statement.

The payment terms management engine 1018 may compare authorized payment terms with the specific characteristics of a given guarantor (including outputs of the scoring subsystem) to determine what payment offers should be made available to the given guarantor. The payment offers may include prompt payment discounts, financial hardship discounts, other discounts, and the like. The authorized payment terms may be preconfigured by a provider or other asset holder with legal ability to collect a payment. The provider or asset holder may configure different authorized terms for different groups, segments, or classifications of guarantors. A guarantor may be grouped by provider-level, guarantor-level, and/or visit-level decisioning and/or underwriting such that any visit or set of visits for any patient and/or for any guarantor can be channeled a customized payment offer. The decisioning may include decisioning rules that define criteria to group guarantors. The criteria, as mentioned, may be at a provider-level, a guarantor-level, and/or a visit-level (e.g., provider, guarantor income estimate, balance amount, insurance carrier, type of treatment, etc.). Providers can also enable automated discounts for uninsured patients pursuant to the provider's policies.

The payment clearance and routing engine 1020 may facilitate payment transactions. For example, the payment clearance and routing engine 1020 may generate transaction authorization requests for interfacing with a payment gateway. The payment clearance and routing engine 1020 may also generate transaction posting files to communicate to a billing system a completed or otherwise effectuated payment transaction. The payment clearance and routing engine 1020 may first clear a financial transaction between a guarantor's bank and a provider's (or asset holder's) bank, facilitated by a third-party payment gateway, and then disaggregate that singular monthly payment to multiple visits (accounts) of the one or more originating billing systems. The payment clearance and routing engine 1020 creates posting files that allocate an appropriate payment amount to the appropriate visits (accounts) within each of the relevant billing systems (with further allocation to principle and interest amounts in the relevant system of record). The payment amount could be a combination of the amount due on the current month's batch of visits plus any monthly payments due on prior batches that have been financed.

The payment posting files may include, but are not limited to, the following: an identifier (e.g., a billing system assigned identifier at a charge level, at the visit charge level, or at the guarantor level), a transaction amount (e.g., a positive or negative amount that may include multiple fields for principle, interest, commission, etc.), a transaction code to define the type of transaction (e.g., patient payment, prompt-pay discount adjustment, interest charged, interest paid, etc.), a reference number (e.g., a field which can be loaded along with the payment and extracted again to load back to the payment management system for use in identifying which payments have or have not yet been posted back into a billing system), a transaction date, and a text note (e.g., text to be shown in the user interface of the billing system).

The dispute engine 1022 may enable dispute functionality for allowing a guarantor to dispute a visit charge on a statement or otherwise facilitate communication between a guarantor and a provider to address issues. A dispute may include a claim that insurance coverage was available or misapplied, a dispute of a charge, a request for charity or other financial assistance, or any other issue, concern, or situation in which a guarantor desires a client provider to reconsider a visit charge and/or to contact the guarantor regarding a visit charge. The dispute engine 1022 may enable secure two-way electronic communication between the guarantor and the client provider. The dispute engine 1022 may change a status of visit charges to "suspended" and/or remove the charge from the account balance until the dispute is resolved. The dispute engine 1022 may also implement or interface with one or more work queues, such as a dispute queue, to queue disputes or other issues for resolution by the client provider.

The financing engine 1024 may provide functionality for configuring financing plans to pay account balances. The financing engine may use a PTP score, or other output of the scoring subsystem 144 of FIG. 1, with decisioning rules (e.g., underwriting limit selections) configured by a provider or asset holder to establish financing offers that are made available to a guarantor desiring to finance a batch of visit charges. The amount for current open charges (e.g., an open charges balance) of a current batch of visit charges (e.g., for each statement period's visits) can be financed according to a new financing plan with unique terms, which may be preset financing terms or financing terms selected or configured by the guarantor (subject to authorized financing terms configured by the provider or asset holder).

The financing engine 1024 may enable provider-level, guarantor-level, and/or visit-level decisioning and/or underwriting such that any visit or set of visits for any patient and/or for any guarantor can be channeled customized financing terms. The decisioning may include decisioning rules that define criteria to group guarantors. The criteria, as mentioned, may be at a provider-level, a guarantor-level, and/or a visit-level (e.g., provider, guarantor income estimate, balance amount, insurance carrier, type of treatment, etc.).

The financing engine 1024 may enable a provider or asset holder to configure various pre-set financing options, each having terms for a group, segmentation, or other classification of guarantors, as determined by the decisioning rules. As stated, the decisioning can be at a provider level, a guarantor level, and/or a visit level. The financing engine 1024 may apply the decisioning rules to group a guarantor, and then may present one or more pre-set financing options corresponding to the group of the guarantor. Described differently, the financing engine 1024 may determine which pre-set financing option(s) to present to a guarantor based upon criteria of the guarantor at one or more of a provider level, a guarantor level, and/or a visit level.

The financing engine 1024 may allow a guarantor to create self-configured financing plans, for example, by choosing a monthly payment amount and subsequently accepting the associated terms the provider has authorized for the resulting amortization schedule (e.g., minimum payment amount, maximum amortization period, interest rates, etc.). Self-configured financing plans may be configured by the guarantor choosing any one or more of an interest rate, a payment amount, a period for repayment, and/or other terms that can be compared to provider-authorized terms and/or associated with provider-authorized terms that can be accepted by the guarantor. Again, the financing engine 1024 may enable a provider or asset holder to configure various guarantor-configurable financing options, each providing authorized terms for a group, segmentation, or other classification of guarantors, as determined by the decisioning rules. As stated, the decisioning can be at a provider level, a guarantor level, and/or a visit level. The financing engine 1024 may apply the decisioning rules to group a guarantor, and then may present one or more guarantor configurable financing options corresponding to the group of the guarantor. Described differently, the financing engine 1024 may determine which set of authorized financing terms apply for a guarantor configurable financing option presented to a guarantor. The determination of which set of authorized financing terms apply may be based upon criteria of the guarantor at one or more of a provider level, a guarantor level, and/or a visit level.

The financing engine 1024 may allow a guarantor to have multiple financing plans active simultaneously and can enable one monthly payment for all open financing plans. In other words, a new financing plan for a current open charges balance is stacked on previously established financing plans for prior open charges balances.

The balance brokering engine 1026 may enable brokering of charges and/or balances. A balance for a batch of open charges, or an open charges balance can be automatically evaluated based on one or more pre-defined evaluation criteria to determine whether the open charges balance should be transferred to a new system of record associated with a new entity. The balance brokering engine 1026 may evaluate the batch of open charges and/or open charges balance based on the pre-defined evaluation criteria. If the one or more pre-defined evaluation criteria are met, the balance brokering engine may automatically effectuate electronic transactions to transfer the open charges balance to an entity associated with the new system of record. More particularly, the balance brokering engine 1026 may automatically effectuate electronic transactions to transfer title of an accounts receivable asset that constitutes some or all rights to collect payment for the open charges balance.

The balance brokering engine 1026 may also integrate provider configuration settings with each guarantor's desired financing choice to determine which system of record should hold the new asset (e.g., an accounts receivable asset or financed balance asset). Once that determination is made, the balance brokering engine 1026 may calculate an appropriate pricing construct established between the provider and a potential new asset holder (e.g., a third-party entity or creditor, such as an owner or operator of the payment management system, a bank, or another special purpose lending or financial institution). The balance brokering engine 1026 may facilitate a financial transaction from the new entity (new asset holder) to the provider to clear the guarantor balance from the provider's system of record (e.g., billing system). The balance brokering engine 1026 may post the transferred asset (e.g., purchased asset) to an appropriate billing system of the new asset holder and subsequently integrate with the payment clearance and routing engine 1020 and statement engine 1016 to accurately clear payments and present accurate account balances for both the provider and the new asset holder.

The principle and interest calculation engine 1028 may calculate a schedule of interest accruals and principle payments due over an amortization schedule for a given financing construct. The principle and interest calculation engine 1028 may dynamically recalculate interest and principle allocations as payments and other debit and credit adjustments flow through the systems of record (e.g., provider billing systems, asset holder billing systems) over time.

The management engine 1030 may interface with the client input subsystem 162 and/or the guarantor input subsystem 164 of FIG. 1 to enable a client provider to generally manage users. The management engine 1030 may enable the client provider to register or approve guarantors or otherwise facilitate completion of the registration process. This may entail reviewing requests for accounts and offering or declining access, and resetting passwords or security credentials. The management engine 1030 may also enable a client provider to manage and respond to (or otherwise address) user requests and guarantor disputes. The client provider may also be able to emulate actions a user can take, such as reviewing transactions and activity for a given account, linking accounts or severing accounts, initiating new financing plans, reconfiguring existing financing plans, or resetting a payment date. The management engine 1030 may enable a client provider to: set a maximum duration for financing plans, set a minimum payment amount, set interest rates for given duration periods, set preset financing plan parameters (e.g., interest rate, if any, and plan duration), set a prompt-pay discount (if any), set an uninsured patient discount, allow or disallow account linking, manage work queues (including a disputes work queue, a delinquent accounts queue, and the like), publish promotional messages on a splash page, offer rewards/incentives for payment, configure provider contact information, work and manage non-sufficient funds transactions, perform payment reconciliation, monitor transaction reporting, and manage exceptions.

Figure 11:
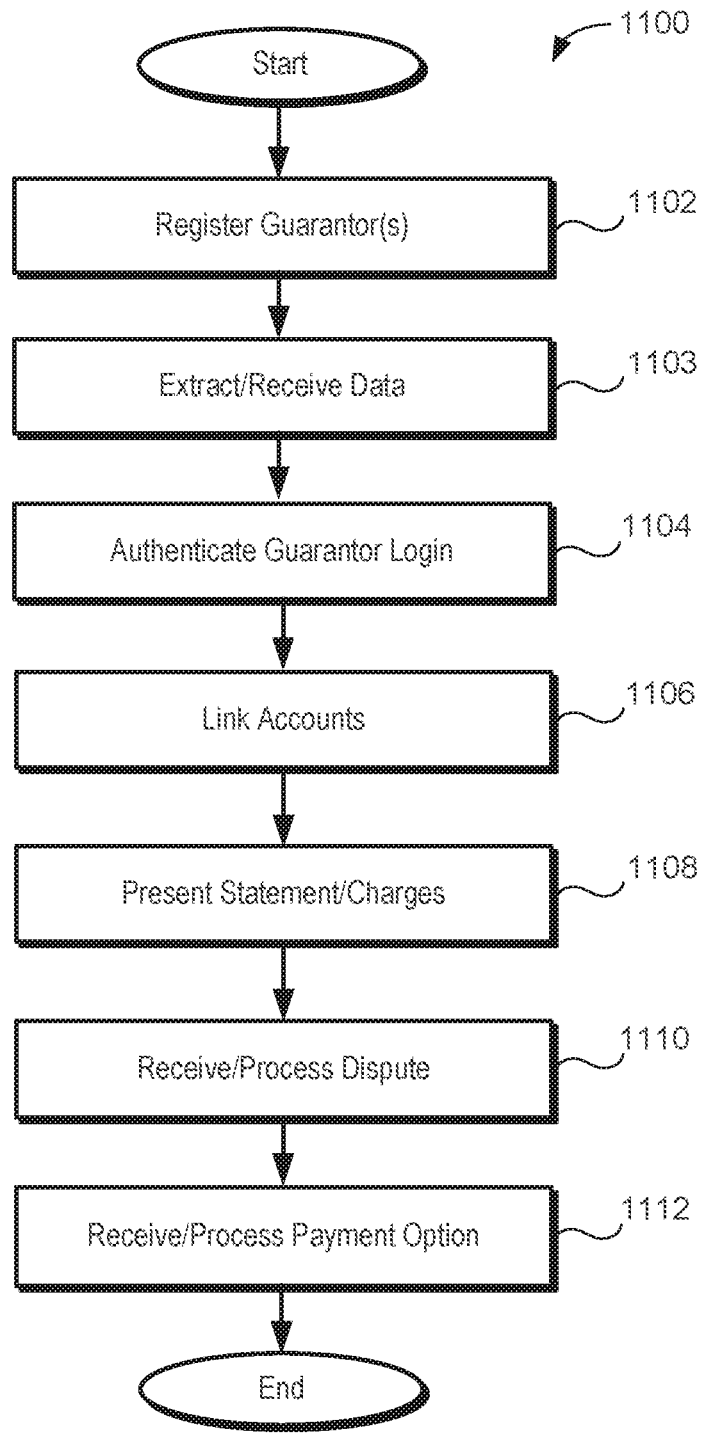
FIG. 11 is a flow diagram of another method of processing payments, according to one embodiment.

FIG. 11 is a flow diagram of another method 1100 of managing payments, according to one embodiment. Guarantors can register 1102 for private access, such as to features and functionalities provided by a private payment portal subsystem. Data is extracted 1103 or otherwise received or accessed, for example, from a billing data source (e.g., one or more billing systems), from a credit data source, and/or from a demographics data source. The data that is extracted 1103, or a portion thereof, may enable linking accounts, presentment of statements and charges, charge dispute processing, and payment processing.

When a registered guarantor logs in, the login of the guarantor may be authenticated 1104 to help ensure that PHI is being provided to an appropriate viewer (e.g., a guarantor or a manager guarantor).

Accounts of registered guarantors can be linked 1106 so that a single guarantor (a manager guarantor) can manage linked accounts, such as the account of a spouse, a parent, or the like. A statement or similar listing of charges on a guarantor's account and all other guarantor and patient accounts the guarantor manages can be presented 1108 to enable the guarantor to understand a balance (e.g., any balance) on the account and to enable the guarantor to arrange payment. A guarantor can arrange payment using either a singular payment to meet payment requirements on all subsidiary accounts (current visits and visits on financing plans) or direct specific payments to individual visits on a one-off basis through either one aggregated payment with allocation detail selected by the guarantor or multiple individual payments at the guarantor's discretion. A guarantor can also dispute a charge presented for payment. The dispute may be processed 1110, such as by temporarily removing the disputed charge from the account balance until resolution of the dispute. The dispute may be automatically entered in a dispute work queue for processing, for example, by the client provider. Payment options can be presented and a selection of an option can be received and processed 1112. The payment options may include, but are not limited to, payment in full, guarantor-configured financing terms, or pre-set financing terms.

Figure 12:
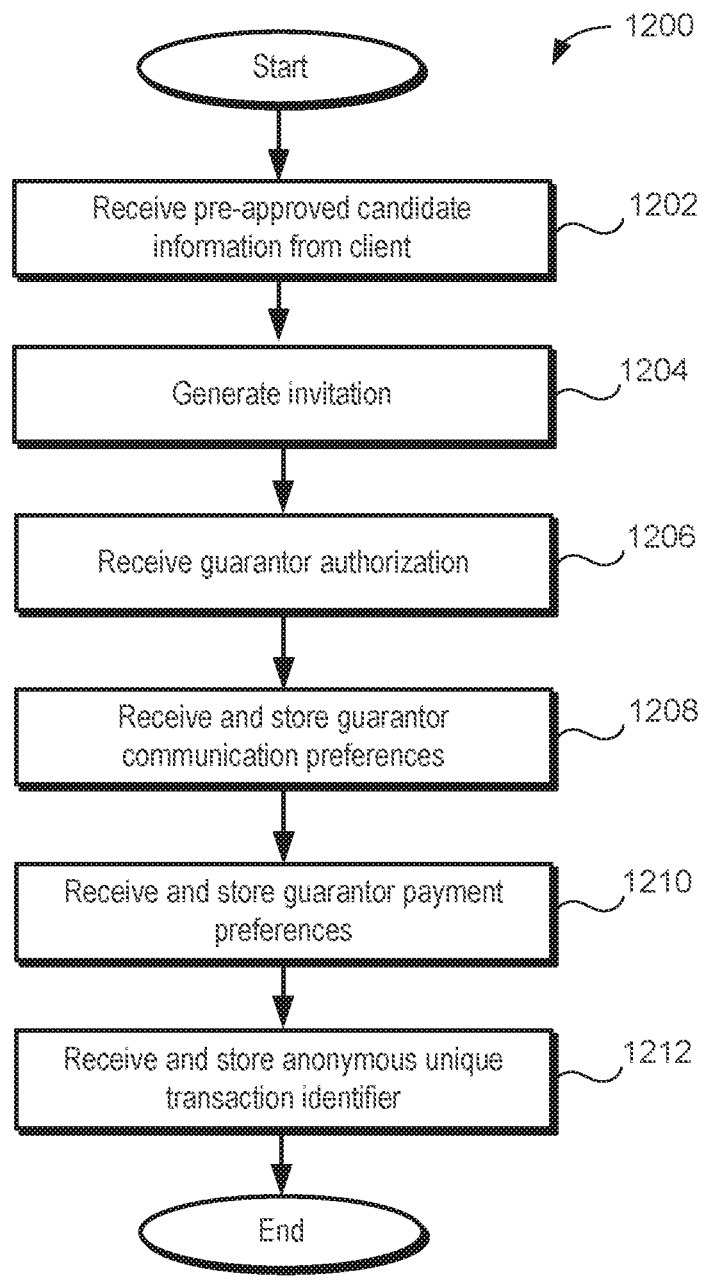
FIG. 12 is a flow diagram of a method of registering a guarantor, according to one embodiment.

FIG. 12 is a flow diagram of a method 1200 of registering a guarantor, according to one embodiment. Pre-approved candidate guarantors may be selected by the client provider, and information for those pre-approved candidate guarantors may be received 1202 from the client provider. The client provider may have obtained the information for potential candidate guarantors during visits (e.g., by the guarantor or a patient-guarantee of the guarantor), and a screening process may determine which potential candidate guarantors are pre-approved. Business intelligence information (e.g., generated by a business intelligence subsystem) and scoring information (e.g., generated by a scoring subsystem) may aid a client provider in such a screening process to select pre-approved candidate guarantors. An invitation to register for payment management is generated 1204 and transmitted or otherwise communicated to the candidate guarantor. The candidate guarantor may provide authorization for the payment management, and the authorization may be received 1206. For example, the generated invitation may be an email including a link (e.g., an Internet URL). The link may provide the candidate access to interface with the private payment portal subsystem and functionality provided therefrom for accepting the invitation to become a registered guarantor. As another example, the link may provide functionality for the candidate to directly accept the invitation to become a registered guarantor. As another example, the generated invitation may include instructions for accepting the invitation, such as sending an email to a particular email account, going to a particular webpage, calling a phone number, providing a passcode, or the like. Authentication (e.g., identity verification) may also be performed at registration such as by cross-checking received guarantor information with third-party data sources to perform identity verification (e.g., looking for one or more matches to a name, address, SSN, email, etc.) or alternatively offering multifactor authentication.

Upon registering, a registered guarantor can provide communication preferences, which may be received and stored 1208. The communication preferences may include, but are not limited to, preferences specifying manner, format, timing, and the like, for providing information to the guarantor concerning the guarantor's account (including accounts linked to the guarantor's account for which the guarantor has assumed management). A registered guarantor may also provide payment preferences, which may be received and stored 1210. The payment preferences may include, but are not limited to, preferences specifying manner (e.g., payment vehicle), format, timing, and the like, for making payments on the guarantor's account. The payment preferences may enable contacting or otherwise interfacing with a payment gateway (e.g., third party) or a financial institution of a payment vehicle, which may generate an anonymous unique transaction identifier that can be used to facilitate payment transactions. The anonymous unique transaction identifier is received 1212 and stored for use during payment processing. The anonymous unique transaction identifier may link the guarantor's account to a previously specified financial services account for subsequent payment authorizations. The anonymous unique transaction identifier may facilitate recurring transactions (using the specified financial services account) without storing payment card industry (PCI) information, such as account numbers and credit card numbers. The anonymous unique transaction identifier may be, for example, a token that is generated by a third-party payment gateway and can be used to facilitate a payment through that payment gateway.

Figure 13:
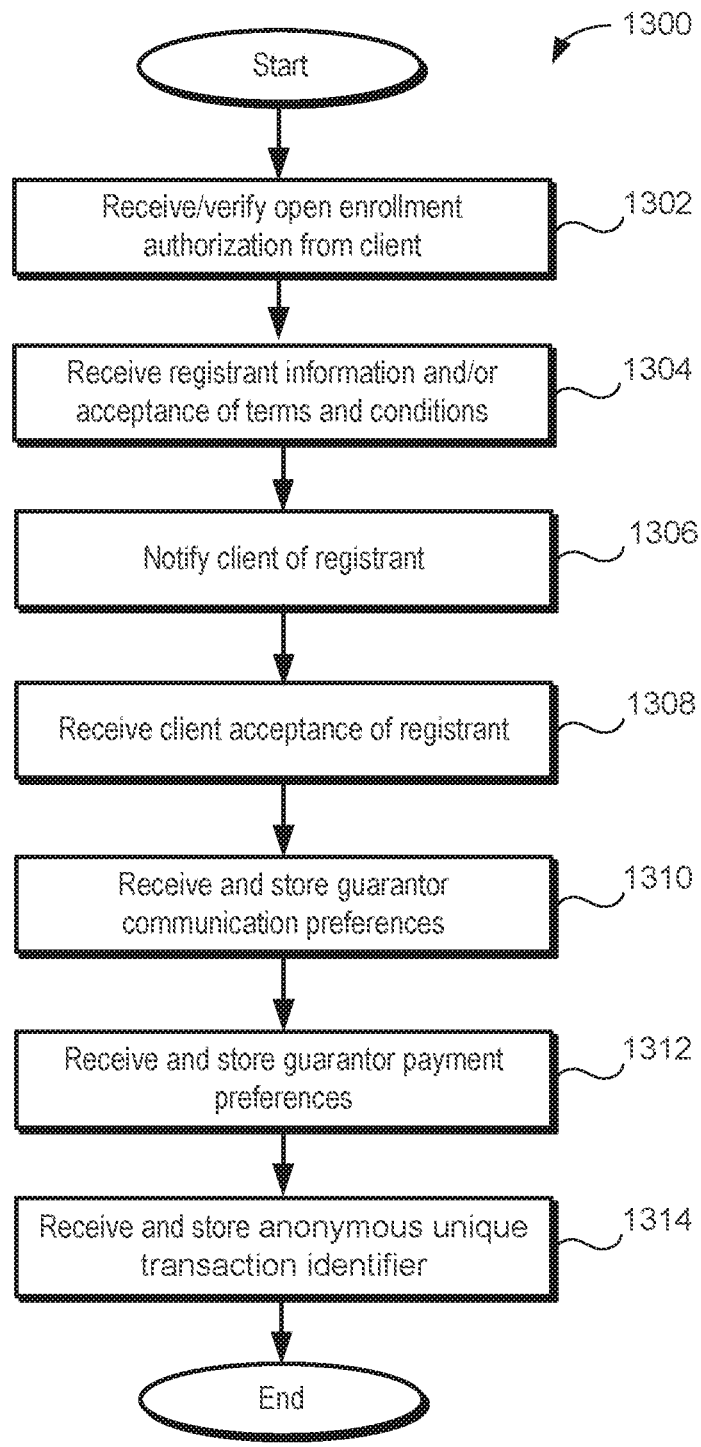
FIG. 13 is a flow diagram of a method of registering a guarantor, according to another embodiment.

FIG. 13 is a flow diagram of a method 1300 of registering a guarantor, according to another embodiment. The client provider may allow open enrollment, and authorization for open enrollment may be received 1302 from the client provider. Registrant information (e.g., name, address, phone number, SSN) and/or acceptance of terms and conditions may be received 1304. The acceptance of terms and conditions may include a form of credit agreement. The client provider may be notified 1306 of the registration of the registrant to allow the client provider an opportunity to review a registrant and accept or reject the registration. Business intelligence information (e.g., generated by a business intelligence subsystem), scoring information (e.g., generated by a scoring subsystem), and identification verification processes (e.g., using data matching algorithms, third-party data, and/or third-party technology) may aid a client provider in determining whether to accept or reject the registration. In addition, authentication of the registrant (e.g., identity verification) may occur, such as by cross-checking received guarantor information with third-party data sources to perform identity verification (e.g., looking for one or more matches to a name, address, SSN, email, etc.) or alternatively offering multifactor authentication. If provider acceptance of the registrant is received 1308, the registered guarantor may be enabled to provide communication and/or payment preferences. The communication preferences may be received and stored 1310. The communication preferences may include, but are not limited to, preferences specifying manner, format, timing, and the like, for providing information to the guarantor concerning the guarantor's account (including accounts linked to the guarantor's account for which the guarantor has assumed management). The payment preferences may also be received and stored 1312. The payment preferences may include, but are not limited to, preferences specifying manner, format, timing, and the like, for making payments on the guarantor's account. The payment preferences may enable contacting or otherwise interfacing with a payment gateway (e.g., third party) or a financial institution of a preferred payment vehicle, which may generate an anonymous unique transaction identifier that can be used to facilitate payment transactions. The anonymous unique transaction identifier may be received 1314 and stored for use during payment processing. The anonymous unique transaction identifier may link the guarantor's account to a previously specified financial services account for subsequent payment authorizations. The anonymous unique transaction identifier may facilitate recurring transactions (using the specified financial services account) without storing PCI information, such as account numbers and credit card numbers. The anonymous unique transaction identifier may be, for example, a token that is generated by a third-party payment gateway and can be used to facilitate a payment through that payment gateway.

Figure 14:
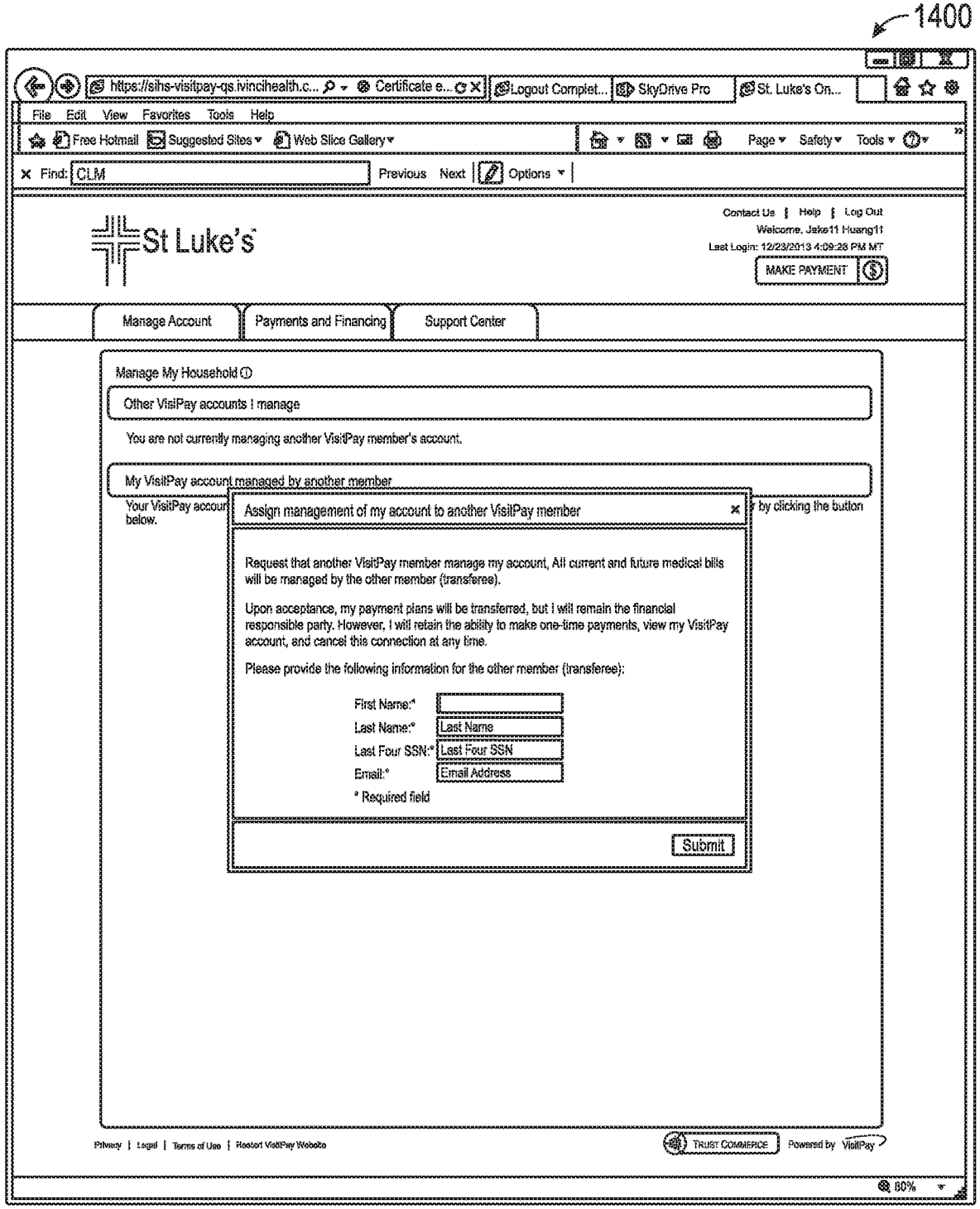
FIG. 14 illustrates a graphical user interface to a private payment portal subsystem, according to one embodiment.

FIG. 14 illustrates a graphical user interface 1400 to a private payment portal subsystem, according to one embodiment. The graphical user interface 1400 provides input fields and functionality for a first guarantor to request that a second guarantor manage the account of the first guarantor. For example, an individual may want to request his/her spouse to manage the individual's account. In the illustrated graphical user interface 1400 of FIG. 14, the first guarantor can provide information for the second guarantor to whom the first guarantor wishes to assign management of the first guarantor's account. The user interface 1400 requests personally identifiable information (e.g., first name, last name, all or a portion of an ID number such as a SSN, and email address) of the manager guarantor to aid in ensuring that guarantors send manage requests only to other personally known guarantors.

As can be appreciated, in other embodiments, a graphical user interface may provide input fields and functionality for a first guarantor to request managerial rights over an account of a second guarantor. For example, an individual may want to request to manage his/her spouse's account. The first guarantor can provide information for the second guarantor whose account the first guarantor wishes to manage. Again, the user interface may collect personally identifiable information of the guarantor to be managed (e.g., name, user ID, and/or last four digits of SSN) to aid in ensuring that guarantors send manage requests only to other personally known guarantors. An electronic notification of both the linking request and the linking acceptance may be sent to both guarantors to ensure they both are aware of and accept the obligations imposed and the permissions granted in the linked (i.e., managed) account arrangement. The electronic notifications may aid in complying with internal client provider policies and/or external regulations (e.g., HIPAA).

Figure 15:
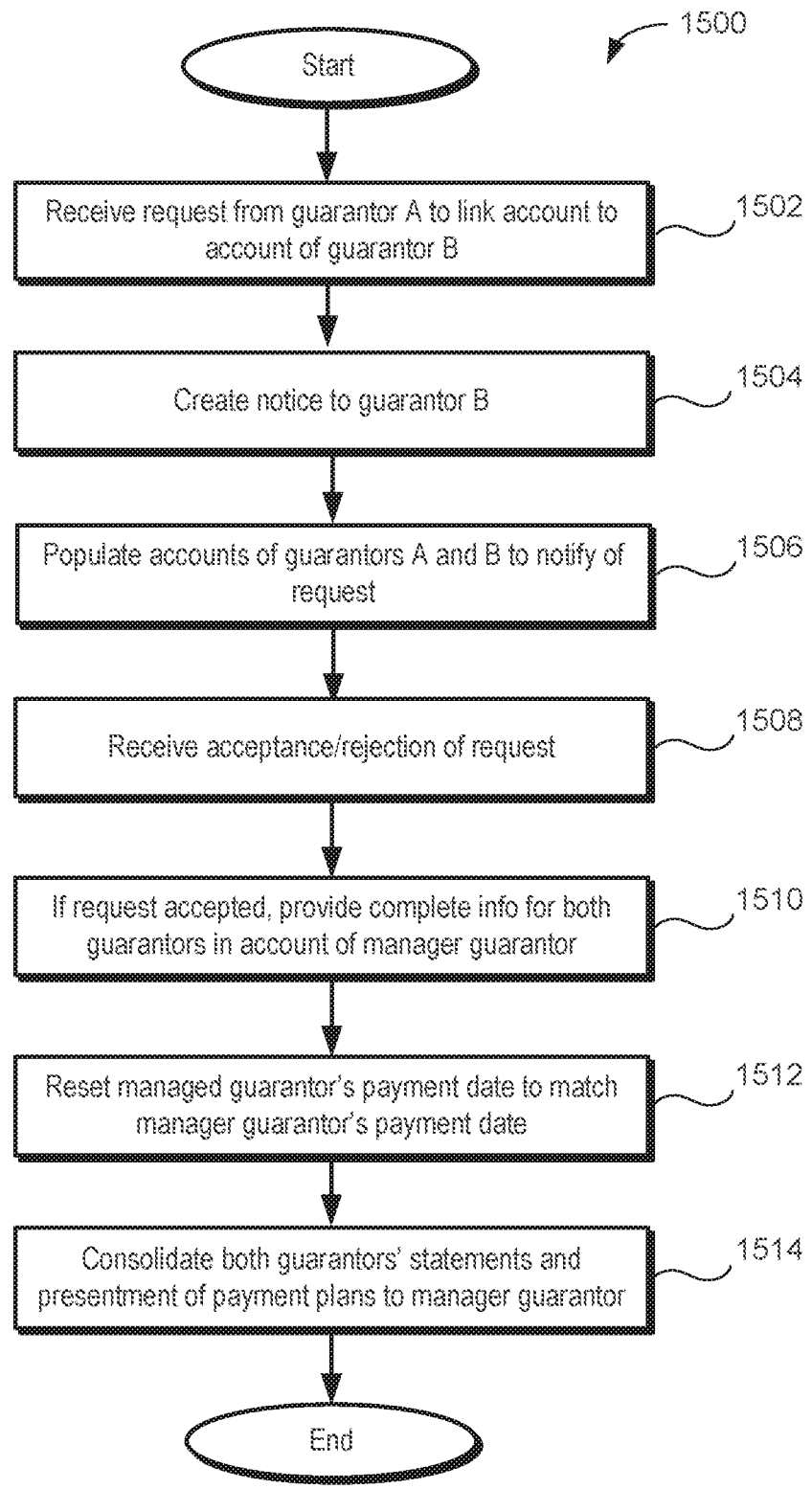
FIG. 15 is a flow diagram of a method of linking guarantor accounts, according to one embodiment.

FIG. 15 is a flow diagram of a method 1500 of linking guarantor accounts, according to one embodiment. A request from a guarantor A (e.g., a first guarantor) is received 1502 to link guarantor A's account to the account of guarantor B (e.g., a second guarantor). The request may be a request to be managed (e.g., for guarantor B to manage guarantor A's account) or a request to manage (e.g., for guarantor A to manage guarantor B's account). A request to be managed may include authorization to release PHI and/or personal account information of the requesting guarantor. The authorization may comply with internal client provider policies and/or external regulations (e.g., HIPAA). A notice of the request is created 1504 and communicated to guarantor B. The accounts of guarantor A and/or guarantor B may be populated 1506 to also give notice of the outstanding manage request. An acceptance of the request may be provided and received 1508. The acceptance of a request to manage (e.g., a request by guarantor A to manage guarantor B's account) may include authorization to release PHI and/or personal account information to the manager guarantor.

If the manage request is accepted, account information, including, for example, specific clinical visit information, for both the managed guarantor and the manager guarantor is provided 1510 in the account of the manager guarantor. In the case of a request to be managed, the account information for guarantor A is provided 1510 in the account for guarantor B. In the case of a request to manage, the account information for guarantor B is provided 1510 in the account for guarantor A. Linking accounts may include resetting 1512 a managed guarantor's payment data to match the manager guarantor's payment date. With the accounts successfully linked, the visit data, charge data, and balance data for the managed guarantor are combined into the account of the manager guarantor and otherwise consolidated 1514 for purposes of presentment of statements and/or financing plans. For example, the manager guarantor can view visit information of the managed guarantor's account. An electronic statement and/or account balance of the manager guarantor would reflect charges for visits of the managed guarantor. For example, even if the manager guarantor does not have current visits for the statement period, if the managed guarantor has a current visit during the statement period then an electronic statement would be generated for the manager guarantor reflecting the visit charges of only the managed guarantor.

Figure 16:
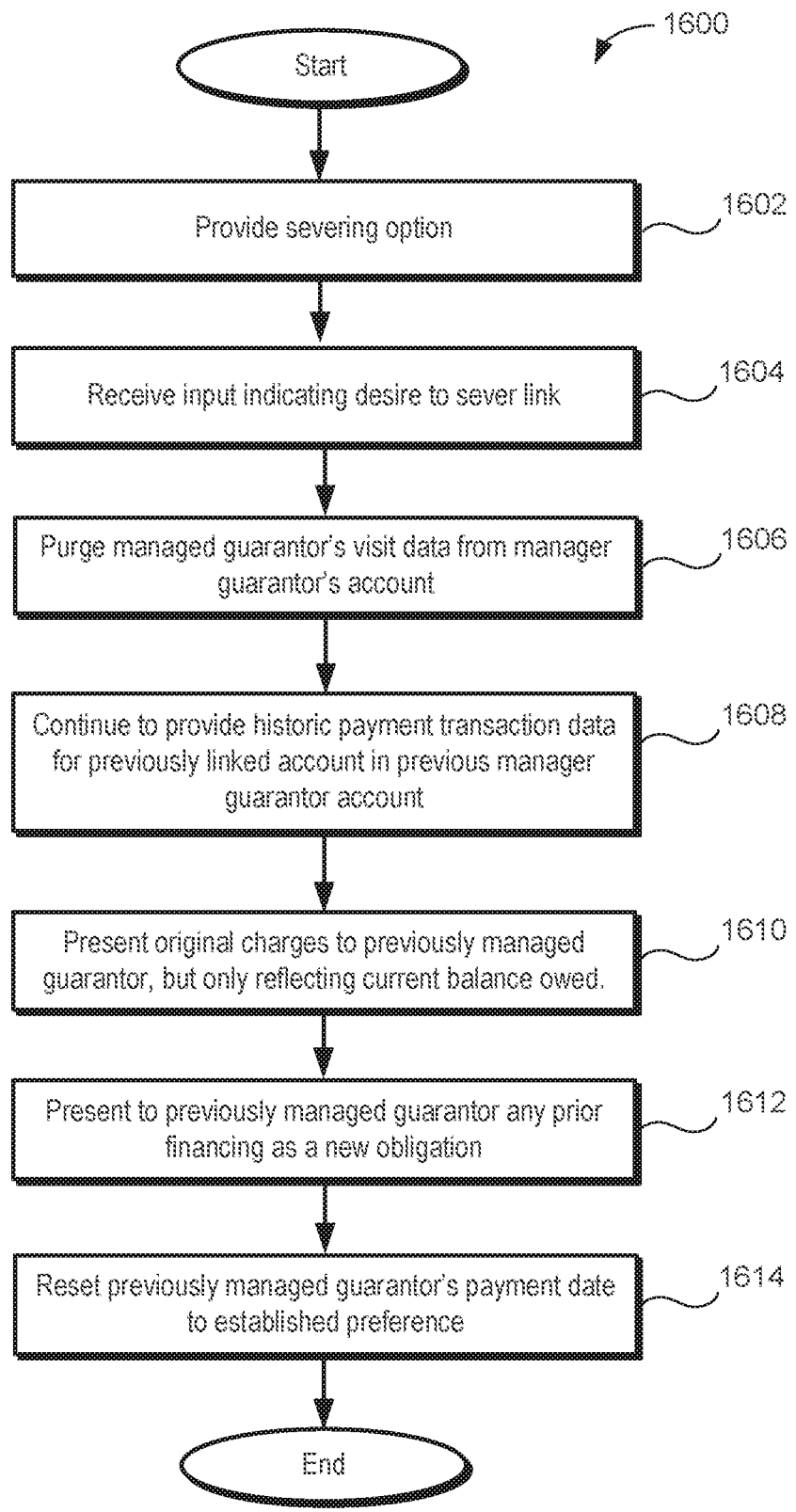
FIG. 16 is a flow diagram of a method of unlinking guarantor accounts, according to one embodiment.

FIG. 16 is a flow diagram of a method 1600 of severing previously linked guarantor accounts, according to one embodiment. A severing option is provided 1602. The severing option may be an electronic link that can be clicked on to indicate a desire to sever linked accounts. The severing option may be presented to the manager guarantor and/or the managed guarantor. Input indicating a desire to sever the link is received 1604. To sever linked accounts, in response to a received 1604 indication, the managed guarantor's non-financial visit data and/or account data is purged 1606 from the manager guarantor's account. The previous manager guarantor is prohibited from seeing any of the PHI or any other information about the previously managed guarantor's accounts, which protects a managed guarantor should they decide to sever. As an example, all information about the managed user's accounts except specific information directly tied to the payment (e.g., date, amount, and account number) may be purged 1606. However, historic payment transaction data for previously linked account(s) continues to be provided 1608 in the previous manager guarantor's account. Accordingly, the previous manager guarantor can access and view the historic transaction data to understand and account for historical payments made to manage the previously managed account. When accessing account information, the previous manager guarantor is presented 1610 with the original charges of the previously managed guarantor (and which were paid for by the previous manager guarantor), but the current balance of the previous manager guarantor reflects only the current balance owed from that guarantor's own visits. Any outstanding balances that remain on financing plans for visit charges not originally attributable to the previous manager guarantor are unwound and presented 1612 to the previously managed guarantor as "new charges" on the previously managed guarantor's next periodic statement. These "new charges" may be presented with payment options to be either paid in full, paid according to the preset financing plan established by the client provider, or converted to a new financing plan configured by that guarantor in accordance with the client provider's policies.

At the severing of an account, the previously managed guarantor may have an outstanding balance owed (not paid in full by previous manager guarantor). As noted above, a managed guarantor may continue to be financially responsible for any unpaid visit charges, despite delegating management of account to another guarantor (manager guarantor). Accordingly, when accounts are severed, an originally responsible guarantor continues to be financially responsible for any guaranteed visit charges. Accordingly, a previously managed guarantor may be presented 1612 the outstanding balance effectively as a new obligation and may be presented payment options (including financing) to pay the new obligation (or outstanding balance). If the previously managed guarantor had (before linking of the accounts) configured a payment date preference that was different from the previous manager's configured payment date, the previously managed guarantor's payment date may be reset 1614 to the previously managed guarantor's established preference.

Figure 17:
FIG. 17 is a graphical user interface to a private payment portal subsystem, according to another embodiment.

FIG. 17 is a graphical user interface 1700 to a private payment portal subsystem, according to another embodiment. The graphical user interface (GUI) 1700 presents an electronic statement 1702 of a manager guarantor. The GUI 1700 may present a permanent record of obligations as they appeared on a statement date. The electronic statement that is presented to the guarantor may include a guarantor's obligations owed to potentially two (or more) different entities. Specifically, a guarantor may have a portion of an open charges balance transferred to a new asset holder. As such, an obligation (e.g., account receivable) could be owed to the provider and an obligation (or a prior obligation from a previously established financing plan) may be owed to a different asset holder.

Figure 18:
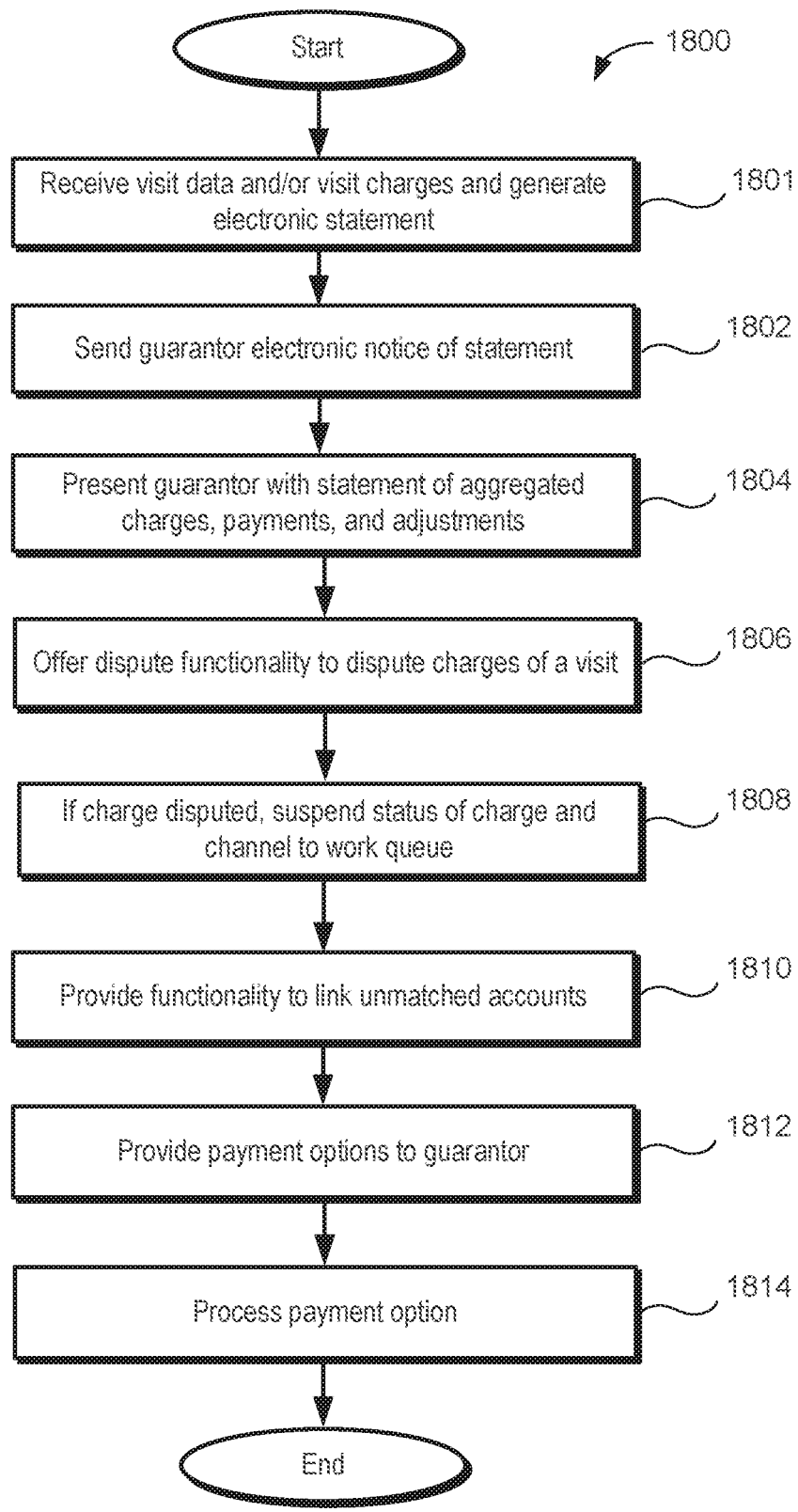
FIG. 18 is a flow diagram of a method for presenting a statement of charges, according to one embodiment.

FIG. 18 is a flow diagram of a method 1800 for presenting a statement or charges, according to one embodiment. Visit data and/or visit charges are extracted or otherwise received 1801 and an electronic statement is compiled or otherwise generated for a guarantor. An electronic notice of an electronic statement is sent 1802 to the guarantor and/or manager guarantor of the account. The electronic notice may be communicated via a communication preference configured by the guarantor or the manager guarantor. For example, the electronic notice may be an SMS text message. As another example, the electronic notice may be an email message. Upon logging in, the guarantor or manager guarantor may be presented 1804 with an interactive overview (e.g., see FIG. 9) and an electronic statement of aggregated charges, payments, and adjustments using extracted data. If the statement is for a manager guarantor, the statement can include visit charges for managed guarantors whose accounts are linked to the manager guarantor.

The electronic statement may serve primarily as an electronic record of required financing disclosures (e.g., interest assessments, payments received, etc.) to meet regulatory requirements. The electronic statement may be provided, for example, in a PDF format. The interactive overview may be an interactive "statement" of charges that dynamically changes with user interaction. When a guarantor first logs in after receiving an electronic notice that a statement is ready, the interactive overview data may match or closely match the electronic statement and reflect, for example, a presumption that the preset or standard payment configuration for new charges will likely be utilized by the guarantor. If the guarantor elects instead to reconfigure the financing plan or make a prompt payment on new charges, the interactive overview data can change (e.g., the current amount due and/or amount to be auto debited will rise or fall accordingly) as soon as that election is saved. If the interactive overview changes according to an action of a guarantor, the interactive overview may be out of sync with the statement. But the next monthly statement may capture the actions taken during this period and reflect balances, charges, interest assessments, discounts, fees, payments, and adjustment, accordingly.

Dispute functionality may also be provided 1806 to enable a guarantor to dispute particular visit charges appearing on the electronic statement. The dispute functionality may suspend 1808 the status of a disputed charge or otherwise temporarily remove the disputed charge from the account balance and/or the current statement until resolution of the dispute. In other words, the amount for a disputed charge may be subtracted from a current amount owed. Accordingly, the balance and/or current amount owed that are reflected on the electronic statement can be impacted by actions of the guarantor. A dispute about a visit charge may be automatically channeled to a work queue, such as a disputes work queue, for processing by the client provider. A dispute record may be generated and introduced to the disputes work queue. The disputes work queue may facilitate tracking and/or processing of disputes and ensuring that disputes are timely resolved by the client provider.

Although a specific visit can be disputed, other visits that comprise a given statement period's charges are not impacted and continue to appear on the electronic statement, the interactive overview, and/or the current balance. In other words, disputing a visit does not prevent a client provider from collecting on non-disputed visits that comprise the current visit charges (e.g., batch or bundle of business). A guarantor could create a financing plan on a batch of current visits, subsequently have additional charges be applied to a specific visit after it was originally billed, and the set of charges for that specific visit could be challenged. The disputed visit could be taken offline effectively without disrupting or impacting the rest of the visit charges within the financing plan.

Account matching functionality may also be provided 1810 to link an unmatched account with the client provider, as mentioned above with reference to the guarantor matching engine 1012 of FIG. 10. A guarantor may be aware of a visit that occurred during the statement period (such as by receiving a paper billing statement from a billing system of the client provider), and the visit and/or corresponding visit charges may not appear in the electronic statement. The visit and/or corresponding visit charges may belong to the current guarantor (or a currently managed guarantor), but may reside in a different billing system of the client provider from other visits and corresponding visit charges that are properly reflected on the electronic statement. The account of the guarantor within the different billing system may be unmatched to the account of the guarantor associated with the electronic statement. The account may be previously unmatched due to a variety of issues (e.g., data input error, incomplete data, typographical error). Irrespective of the billing system from which the unmatched account originated, the account matching functionality that is provided 1810 enables the guarantor to locate the missing visit data and match the associated billing system account with the guarantor's account corresponding to the electronic statement. Even for charges that a guarantor may not be aware of, matching logic may identify accounts in the billing system(s) that should be associated with a guarantor account record in the payment management system. The matching logic may determine the guarantor account those previously unmatched billing system accounts should be associated with and can associate those unmatched billing system accounts to the appropriate guarantor account record in the payment management system. Once the unmatched account is matched to the guarantor's account, the interactive electronic statement may be updated to reflect additional visit data. Once an unmatched billing system account is associated with a guarantor account in the payment management system (either through matching logic or if user manually links an otherwise orphan account), that association persists even though the billing system itself may not recognize the relationship. In other words, the billing system may not be updated based on the matching process. The billing system tracking remains independent of the payment management system tracking.

Payment options are also provided 1812 to the guarantor to make a payment on the balance shown on the electronic statement. As noted previously, the payment options may include:

Pay in full for new visits to potentially earn a prompt-pay discount, based on choices and/or configured preferences of the client provider and possibly subject to what is allowed by the guarantor's insurance plan.

Customize a new financing plan to pay a new balance comprising charges for visits from a current statement period, subject to policies and preferences of the client provider.

Accept (e.g., by taking no action or affirmatively accepting) preset financing terms for a multi-month financing plan at a pre-established interest rate (e.g., a low or 0.0% interest rate) as configured by the client provider.

Providing 1812 payment options may include receiving input for making a payment in full. Providing 1812 payment options may include receiving input specifying customized terms for a new financing plan and comparing the customized terms to preferences, constraints, stipulations, policies, and the like of the client provider and/or external regulations. Selecting a payment option may alter the amount due for new charges during that statement period. For example, in the case where the electronic statement is generated assuming the preset financing option would be selected, customizing a financing plan or paying new charges in full while receiving a prompt-pay discount may alter the amount due. The interactive overview of the account (e.g., see FIG. 9) may change on prospective items as a result of guarantor interaction and payment selections. The next periodic billing statement will reflect these new actions. In other words, the amount a guarantor is expected to pay on a received statement may change based on a payment option selection that departs from an assumed payment option (e.g., preset financing terms or payment in full) used to generate the electronic statement.

A payment on the account, for the electronic statement, may be processed 1814. At any point, the guarantor (or manager guarantor) for whom the electronic statement was generated may make a payment against a balance owed. The payment may match a current amount due on the statement. Alternatively, the payment may be different from a current amount due. When the payment is different from the current amount due, rules may specify an order of applying payment to the current amount due. The current amount due may comprise payments for previously accepted/configured financing plans as well as the current visit charges. The payment may be applied to the oldest financing plans first. Or another ordering may be specified, according to preferences and/or settings defined by the system, the client provider, and/or an asset holder. A posting file may be generated to inform the respective billing system(s) of which accounts or charges the payment should be applied.

Figure 19:
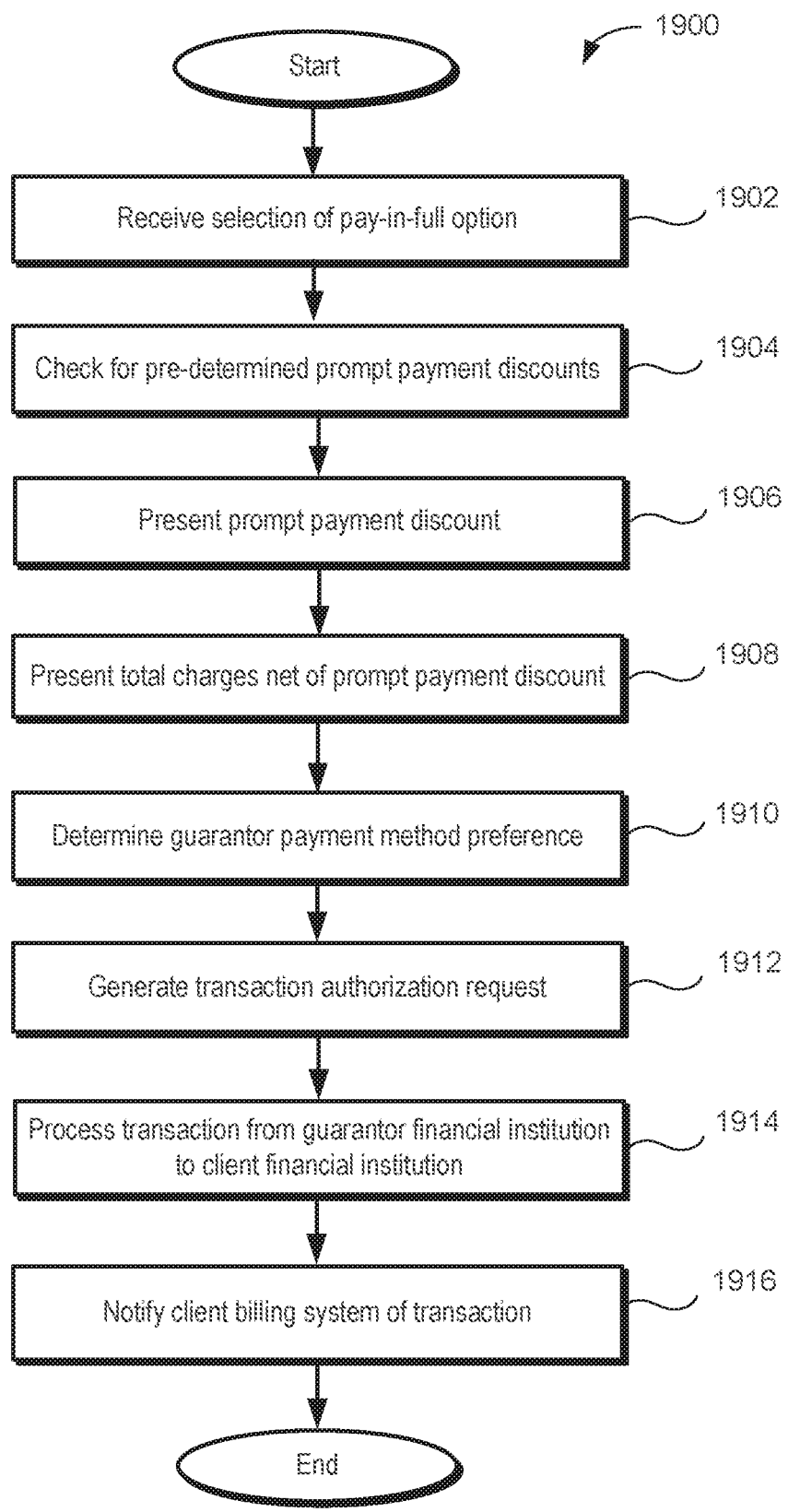
FIG. 19 is a flow diagram of a method of processing payment for healthcare services, according to one embodiment.

FIG. 19 is a flow diagram of a method 1900 of receiving payment for healthcare services, according to one embodiment. Input indicating selection of a payment-in-full option may be received 1902. There may be a check 1904 for any predetermined prompt payment discounts or other discounts offered by the client provider. The discounts offered may depend on guarantor characteristics at one or more of a provider level, a guarantor level, and a visit level. Decisioning rules may determine a grouping of a guarantor based on the guarantor characteristics and may define any discounts offered for that grouping. The client provider may configure such discounts, and they may be stored in a client-configured database (e.g., within the datastore 121 of FIG. 1). If a prompt payment discount (or other discount) is available, the guarantor may be presented 1906 with the discount amount and/or terms. The guarantor may also be presented 1908 the total for the new visit charges net of the discount.

Guarantor preferences may be checked to determine 1910 payment preferences for the guarantor. The payment preferences of the guarantor may include a payment method preference specifying a preferred mode of payment or payment vehicle (e.g., the guarantor's credit card, debit card, bank account, or Health Savings Account). A financial transaction authorization request is generated 1912. The transaction is processed 1914 between the guarantor financial institution and the client provider financial institution. The processing 1914 may be facilitated and/or performed by a payment gateway. Authorization for the transaction may be granted and thus received in response to the transaction authorization request. Alternatively, a confirmation of a completed or otherwise effectuated transaction may be received, for example, directly from the guarantor and/or the client provider financial institution(s). Once the transaction has been completed or otherwise effectuated, the billing system may be notified 1916 of the transaction. The notification may occur by generation of a transaction posting file that may be transmitted to the billing system. The transaction posting file may inform the respective billing system(s) as to which specific accounts or charges the payment should be applied.

Figure 20:
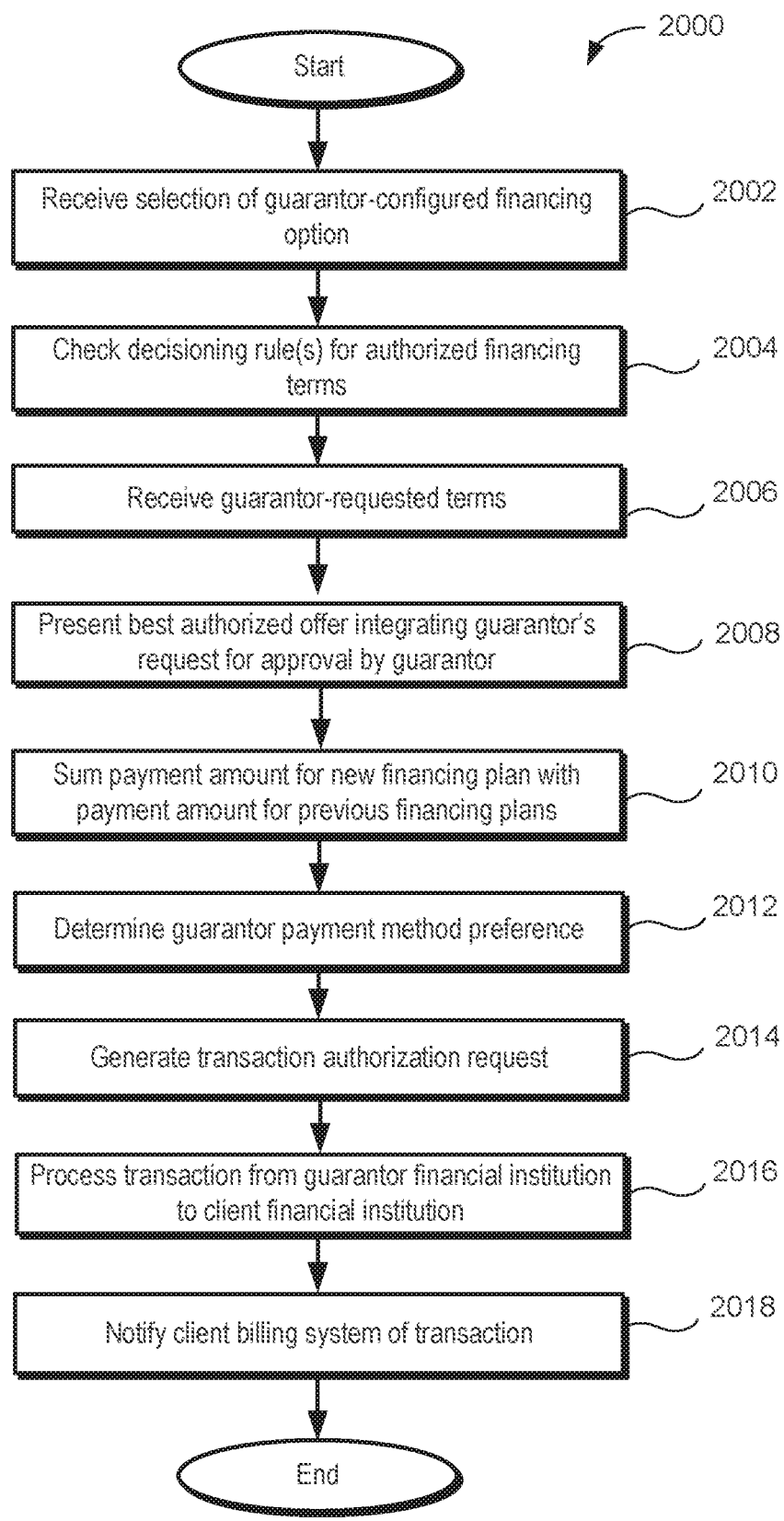
FIG. 20 is a flow diagram of a method of processing payment for healthcare services, according to another embodiment.

FIG. 20 is a flow diagram of a method 2000 of receiving payment for healthcare services, according to another embodiment. Input indicating selection of guarantor-configured financing may be received 2002. There may be a check 2004 for rules, stipulations, or constraints specifying parameters for financing plans that are authorized by the client provider. As an example, decisioning rules may group a guarantor according to guarantor characteristics at one or more of a provider level, a guarantor level, and a visit level. The decisioning rules may also specify authorized financing terms for guarantor-configured financing options presented to a guarantor matching the characteristics for that grouping. The client provider may configure the decisioning rules and/or the authorized financing terms, and they may be stored in a client-configured database (e.g., within the datastore 121 of FIG. 1). The guarantor requested-financing terms may also be received 2006 from a guarantor. The guarantor-requested financing terms may be compared to authorized financing terms, and a best financing offer integrating the guarantor's request within the authorized financing terms is determined and presented 2008 for approval by the guarantor. If the guarantor approves, the amount for the first payment for the new financing plan is summed 2010 with the payment amount for previous outstanding financing plans for presentation to the guarantor.

Guarantor preferences may be checked to determine 2012 payment preferences for the guarantor. The payment preferences of the guarantor may include a payment method preference specifying a preferred mode of payment or payment vehicle (e.g., the guarantor's credit card, debit card, bank account, or Health Savings Account). A financial transaction authorization request is generated 2014. The transaction is processed 2016 between the guarantor financial institution and the client provider financial institution. The processing 2016 may be facilitated and/or performed by a payment gateway. Authorization for the transaction may be granted and thus received in response to the transaction authorization request. Alternatively, confirmation of the transaction may be received. Once the transaction has been completed or otherwise effectuated, the billing system may be notified 2018 of the transaction. The notification may occur by generation of a transaction posting file that may be transmitted to the billing system. The transaction posting file may inform the respective billing system(s) as to which specific accounts or charges the payment should be applied.

Figure 21:
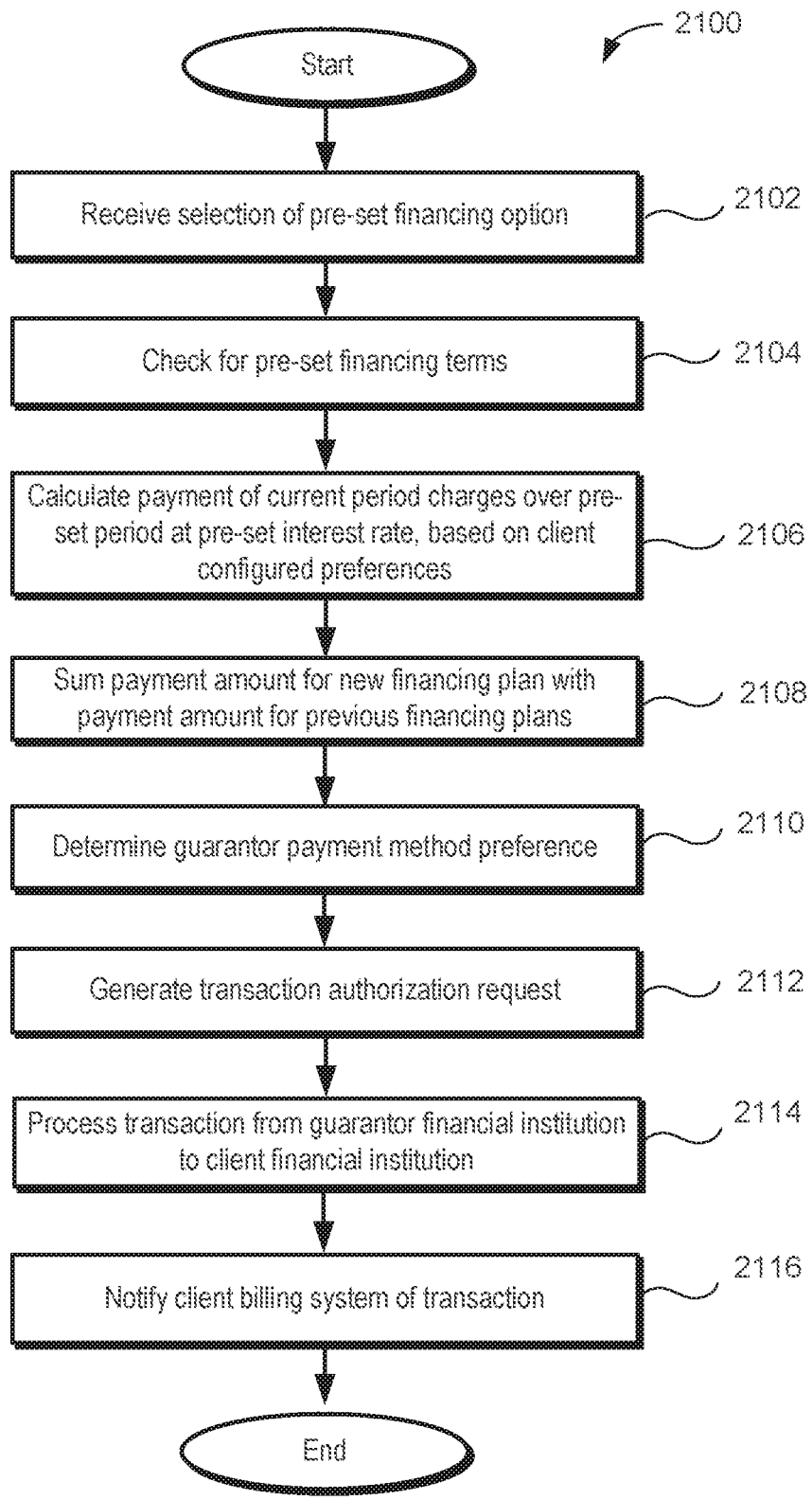
FIG. 21 is a flow diagram of a method of processing payment for healthcare services, according to another embodiment.

FIG. 21 is a flow diagram of a method 2100 of receiving payment for healthcare services, according to yet another embodiment. Input indicating selection or acceptance of pre-set financing option may be received 2102. In some embodiments, acceptance may be received by passage of time and/or lack of selection of another payment option. In other words, if the guarantor does not select a payment option by a given date (e.g., a due date of the statement), the pre-set financing option may be automatically presumed to be accepted.

There may be a check 2104 for rules, stipulations, or constraints, specifying pre-set financing terms configured by the client provider and/or the present or eventual asset holder. The rules may define groupings or categories of guarantors based on criteria at any one or more of a provider level, a guarantor level, and/or a visit level, to specify different pre-set financing terms for each grouping or category. For example, decisioning rules may be defined at a provider level to specify a first set of pre-set financing terms for guarantors having charges incurred from (or amounts or balances owed to a first provider and to specify to a second set of pre-set financing terms for charges incurred from (or amounts or balances owed to) a second provider. As another example, decisioning rules may be defined at a guarantor level to specify a first set of pre-set financing terms for guarantors having a first set of attributes (e.g., a PTP score, a credit score, an estimated household income level, an estimated household size, and an ability to pay (ATP) score) and to specify a second set of pre-set financing terms for guarantors having a second set of attributes. As still another example, decisioning rules may be defined at a visit level to specify a first set of pre-set financing terms for a guarantor according to characteristics of visit charges (or corresponding visits) included in a current batch of open charges and/or open charges balance of the guarantor. The decisioning rules may specify a second set of pre-set financing terms for a guarantor for a guarantor having visit charges with different characteristics. The rules may be defined by a provider or other asset holder (e.g., holder of title of an accounts receivable asset that constitutes rights to collect payment for a balance, such as an open charges balance) to specify different financing plan parameters for different situations. The client provider or other asset holder may configure such rules and corresponding financing plan parameters and they may be stored in a client-configured database (e.g., within the datastore 121 of FIG. 1).

The payment of the current period charges over the pre-set multiple number of periods at a pre-set interest rate may be calculated 2106, based on the pre-set financing terms. For example, the pre-set number of periods and/or preset interest rate may be based on client-configured preferences, for example, stored in a client-configured database (e.g., in the datastore 121 of FIG. 1). In one embodiment, the terms of the financing plan of the pre-set financing option may be configured to comply with a definition under law of a payment plan that is not subject to more stringent regulatory requirements (e.g., presently four months). In other embodiments, the terms of the pre-set financing option may be determined according to decisioning rules. In other words, the terms of the pre-set financing option may vary depending on guarantor characteristics. The pre-set financing option may vary based on guarantor characteristics at one or more of a provider level, a guarantor level, and/or a visit level.

There may be a check 2106 for rules, stipulations, or constraints, specifying parameters for financing plans that are authorized by the client provider. The rules may define groupings or categories of guarantors based on criteria at any one or more of a provider level, a guarantor level, and/or a visit level, to specify different financing plan parameters for each grouping or category. For example, decisioning rules may be defined at a provider level to specify a first set of financing plan parameters guarantors having charges incurred from (or amounts or balances owed to) a first provider and to specify to a second set of financing plan parameters for charges incurred from (or amounts or balances owed to) a second provider. As another example, decisioning rules may be defined at a guarantor level to specify a first set of financing plan parameters for guarantors having a first set of attributes (e.g., a PTP score, a credit score, an estimated household income level, an estimated household size, and an ability to pay score) and to specify a second set of financing plan parameters for guarantors having a second set of attributes. As still another example, decisioning rules may be defined at a visit level to specify a first set of financing plan parameters for a guarantor according to characteristics of visit charges (or corresponding visits) included in a current batch of open charges and/or open charges balance of the guarantor. The rules may be defined by a provider or other present or eventual asset holder (e.g., holder of title of an accounts receivable asset that constitutes rights to collect payment for a balance, such as an open charges balance) to specify different financing plan parameters for different situations. The client provider or other asset holder may configure such rules and corresponding financing plan parameters, and they may be stored in a client-configured database (e.g., within the datastore 121 of FIG. 1). The calculated payment may be compared to authorized financing terms and altered as necessary. The amount for the first payment for the new financing plan is summed 2108 with the payment amount for previous outstanding financing plans for presentation to the guarantor.

Guarantor preferences may be checked to determine 2110 payment preferences for the guarantor. The payment preferences of the guarantor may include a payment method preference specifying a preferred mode of payment or payment vehicle (e.g., the guarantor's credit card, debit card, bank account, or Health Savings Account). A financial transaction authorization request is generated 2112. The transaction is processed 2114 between the guarantor financial institution and the client provider financial institution. The processing 2114 may be facilitated and/or performed by a payment gateway. Authorization for the transaction may be granted and thus received in response to the transaction authorization request. Alternatively, confirmation of the transaction may be received. Once the transaction has been completed or otherwise effectuated, the billing system may be notified 2116 of the transaction. The notification may occur by generation of a transaction posting file that may be transmitted to the billing system. The transaction posting file may inform the respective billing system(s) as to which specific accounts or charges the payment should be applied.

Figure 22:
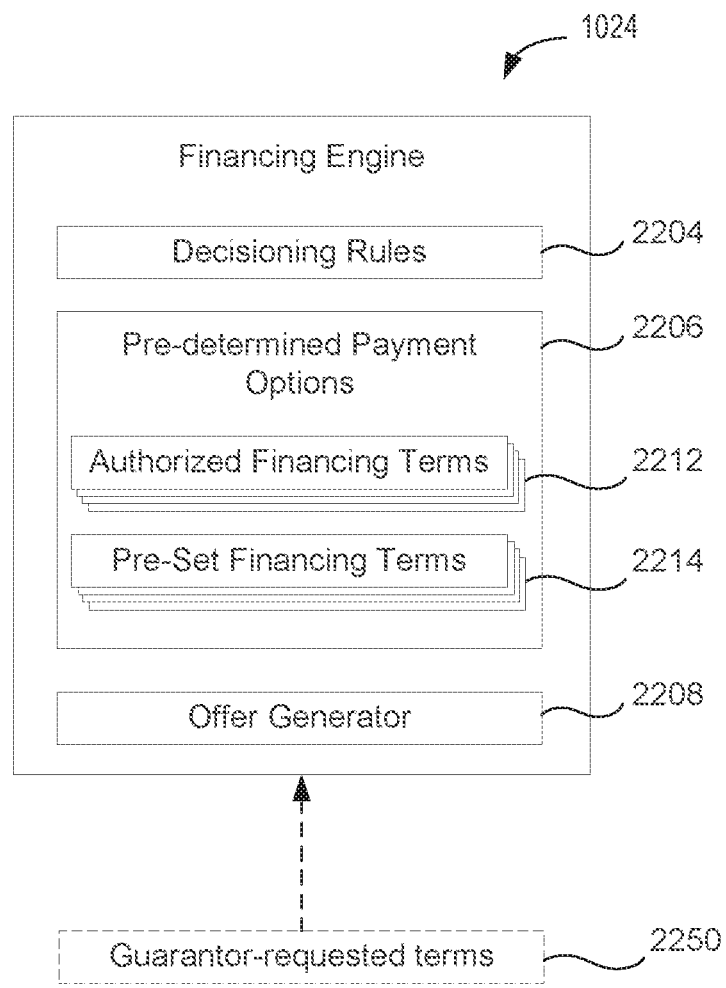
FIG. 22 is a diagram of a financing engine of a payment management system, according to one embodiment.

FIG. 22 is a diagram of a financing engine 1024 of a payment management system, according to one embodiment. The financing engine 1024 may include decisioning rules 2204, pre-determined payment options 2206, and an offer generator 2208. The pre-determined payment options 2206 may include authorized financing terms 2212 for guarantor-configurable financing options and pre-set financing terms for pre-set financing options. The financing engine 1024 may present to a guarantor of one or more visit charges one or more pre-determined payment options 2206 for paying an open charges balance, receive a guarantor selection of one of the pre-determined payment options, and determine a payment amount based on the selected one of the pre-determined payment options. More particularly, the financing engine 1024 may provide a set of one or more pre-determined payment options 2206, including authorized financing terms 2212 and/or pre-set financing terms 2214, determined as described below. By providing the pre-determined payment options, the financing engine 1024 enables payment flexibility for guarantors.

The decisioning rules 2204 may be configured by an asset holder of an open charges balance that the guarantor is expected to pay. The asset holder may be a provider of the services, an operator of the payment management system, or a third party entity to which the open charges balance was transferred or will be transferred (e.g., by the balance brokering engine in FIG. 10), upon finalizing terms of a financing construct with the guarantor. Each decisioning rule may specify criteria that group a guarantor (e.g., into a classification or segment). The criteria may specify characteristics of the guarantor at one or more of a provider level, a guarantor level, and a visit level. Each decisioning rule may also specify one or more pre-determined payment options are presented to a guarantor. For example, the decisioning rule may specify authorized financing terms 2212, which the asset holder intends to apply to guarantors that satisfy the criteria of the decisioning rule.

The provider-level criteria consider guarantor characteristics relating to a provider of services or otherwise associated with the visit charges of the open charges balance. In other words, the provider-level criteria consider provider characteristics, such that the authorized financing terms of the guarantor-configured financing option depend on a visit provider for the one or more visit charges. As an example, a provider-level criteria may specify that the decisioning rule payment options apply to the guarantor if the visit charges include charges from a particular provider. In this manner, guarantors owing payments to a first provider (e.g., St. Luke's) may be grouped into a category and receive a set of one or more corresponding pre-determined payment options while guarantors owing payments to a second provider (e.g., Intermountain Healthcare), may be grouped into a different category and receive a different set of one or more corresponding pre-determined payment options.

The guarantor-level criteria consider guarantor characteristics specific to the given guarantor. Examples of types of guarantor-level criteria include, but are not limited to: a PTP score, a credit score, an income estimate, a size of household estimate. an ability to pay score, a total amount presently owing to one or more providers, a location (e.g., residence) of the guarantor, physical characteristics of the guarantor (e.g., height, weight, blood pressure), and a type of insurance held by a guarantor. Accordingly, a first guarantor having a first PTP score may be presented different pre-determined payment options than a second guarantor having a second PTP score that is different from the first PTP score.

The visit-level criteria consider guarantor characteristics relating to visits and/or visit charges of the open charges balance. Examples of types of visit-level criteria include, but are not limited to: a visit charge amount, an open charges balance, an age of the open charges, a location of the visit, and a visit benefit (e.g., a treatment provided) to a beneficiary of the visit.

As noted, the pre-determined payment options may include one or more of authorized financing terms 2212 for guarantor-configurable financing options and pre-set financing terms 2214 for pre-set financing options. The authorized financing terms 2212 and pre-set financing terms 2214 may provide for a variety of financing types, including open-ended installment loan financing, revolving open-ended credit financing, and close-ended financing. For example, installment loan financing terms may include an amortization of the open charges balance into multiple regular periodic payments. As another example, revolving open-ended credit financing terms may simply specify a minimum payment amount due.

The authorized financing terms 2212 may provide allowable ranges into which guarantor-configured financing terms may fall. Guarantor-requested financing terms 2250 received from a guarantor may be compared to the authorized financing terms 2212 by the offer generator to generate a financing offer for an open charges balance. The guarantor-requested financing terms may include one or more of: a financing type (e.g., installment loan type, revolving credit type), a desired number of periods for payment over which recurring payments will be made to complete payment of the open charges balance, a desired interest rate, an interest rate type, including a fixed interest rate or a variable interest rate, a period payment amount; and a minimum payment amount. The authorized financing terms 2212 may indicate acceptable minimums, ranges, or otherwise authorized terms per the provider and/or asset holder. The authorized financings terms may include one or more of a financing type (e.g., installment loan type, revolving credit type), a minimum payment amount, a maximum amortization period, a minimum interest rate, an interest rate type (e.g., a fixed interest rate or a variable interest rate), interest rate tranches, an interest free period, a credit limit for open charges, interest bearing or non-interest bearing, a prompt payment discount, a charity (or hardship) discount, a pre-payment discount, and a self-pay discount.

The offer generator 2208 may compare guarantor characteristics to criteria of the decisioning rules 2204 to determine an appropriate set of one or more pre-determined payment options, including corresponding authorized financing terms and/or pre-set financing terms 2214. The offer generator 2208 may receive guarantor requested terms 2250, in the case of guarantor-configurable payment options and compare those terms to the authorized financing terms 2212. Based on the decisioning rules and any comparison to authorized financing terms 2214, the offer generator 2208 generates an appropriate financing offer for the guarantor to finance the open charges balance.

Figure 23:
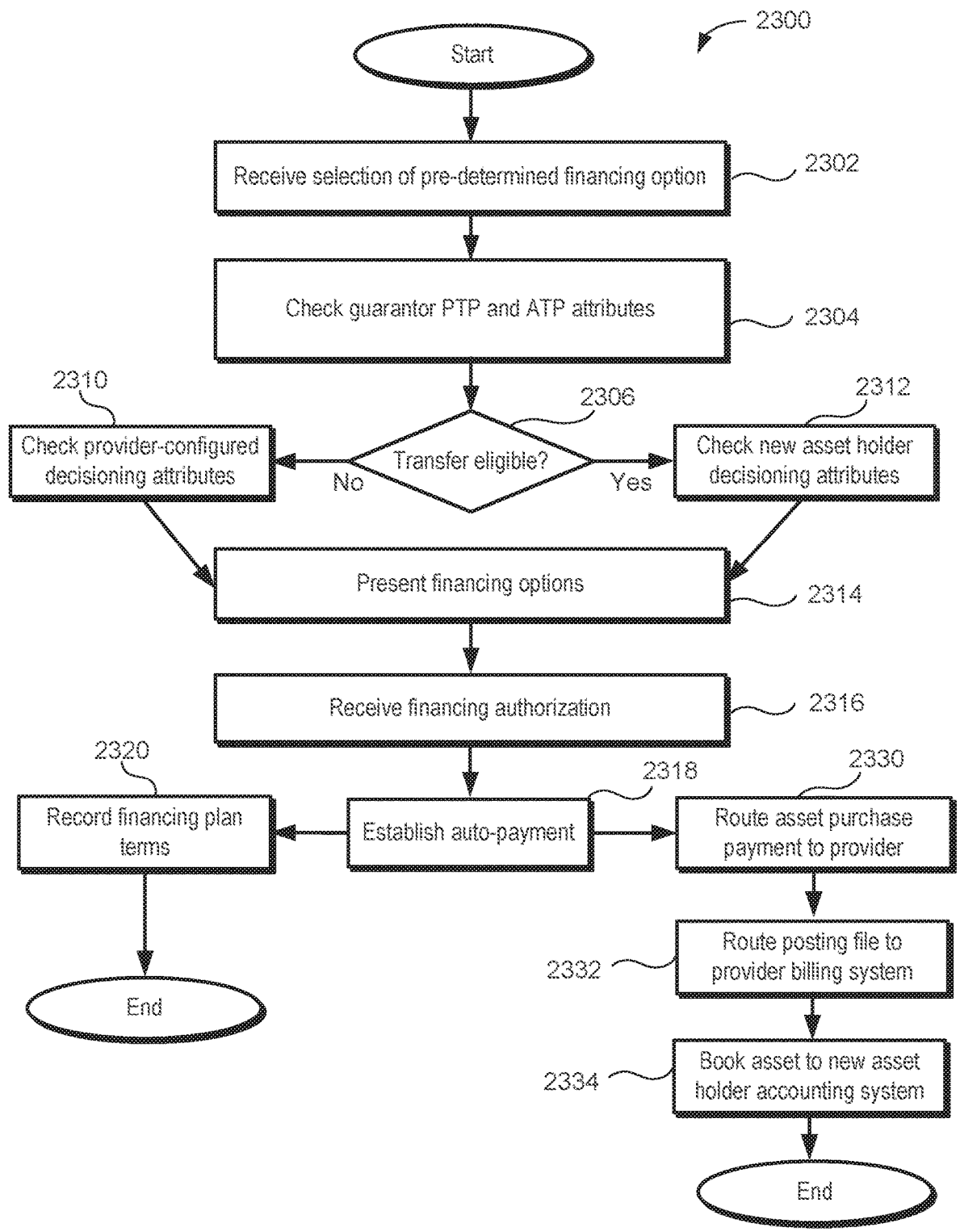
FIG. 23 is a flow diagram of a method of brokering a balance, according to one embodiment.

FIG. 23 is a flow diagram of a method 2300 of brokering a balance, according to one embodiment. A guarantor selection requesting a pre-determined financing option may be received 2302 indicating the guarantor desires to finance an open charges balance. The open charges balance may be determine by compiling one or more visit charges for a guarantor during a time period into a current batch of open charges and aggregating all the open charges to a balance. The guarantor's propensity-to-pay (PTP) and ability-to-pay (ATP) attributes may be checked 2304 or otherwise examined to determine a likelihood of the open charges balance being paid by the guarantor. A determination 2306 may be made to assess if the asset resulting from a financing plan is eligible to be transferred. The determination 2306 may be based on criteria established by the provider and/or criteria established by a potential new asset holder (transferee). If the determination 2306 is "No," the open charges balance is not transfer eligible, the open charges balance will remain held by the provider and provider-configured decisioning attributes (e.g., decisioning rules) may be checked or otherwise considered to determine financing options for presentation 2314 to the guarantor. If the determination 2306 is "Yes," the open charges balance is eligible for transfer, the open charges balance can be transferred to a new asset holder, such as an operator of the payment management system or a third-party entity (such as a financial or lending institution). Decisioning attributes (e.g., decisioning rules) of the potential new asset holder may be checked 3212 or otherwise considered to determine financing options for presentation 2314 to the guarantor. Based on appropriate decisioning attributes, appropriate financing options are presented 2314 to the guarantor for consideration. The financing options 2314 may be presented to a client computing system, for example, over a network such as the Internet. The guarantor can select a financing option and provide authorization or approval of the terms. The financing authorization is received 2316 from the guarantor. An auto-payment is established 2318 according to the terms of the financing option.

If the open charges balance is remaining with the provider, the auto-payment is established 2318 to transfer funds from the guarantor bank account to the provider bank account. The financing plan terms are recorded 2320 by the payment management system.

If the open charges balance is to be transferred, the auto-payment is established 2318 to transfer funds from the guarantor bank account to the new asset holder bank account. In the case of a transferred asset, an asset purchase payment is routed 2330 from the new asset holder to the provider (e.g., electronic transactions are effectuated). Also, a posting file is routed 2332 to the provider billing system to communicate satisfaction of the balance with respect to the provider system (and thus assumption of the balance by the new asset holder). The transferred asset is booked 2334 or otherwise recorded to the accounting system of the new asset holder (e.g., a system of record, a G/L, and/or the like).

Figure 24:
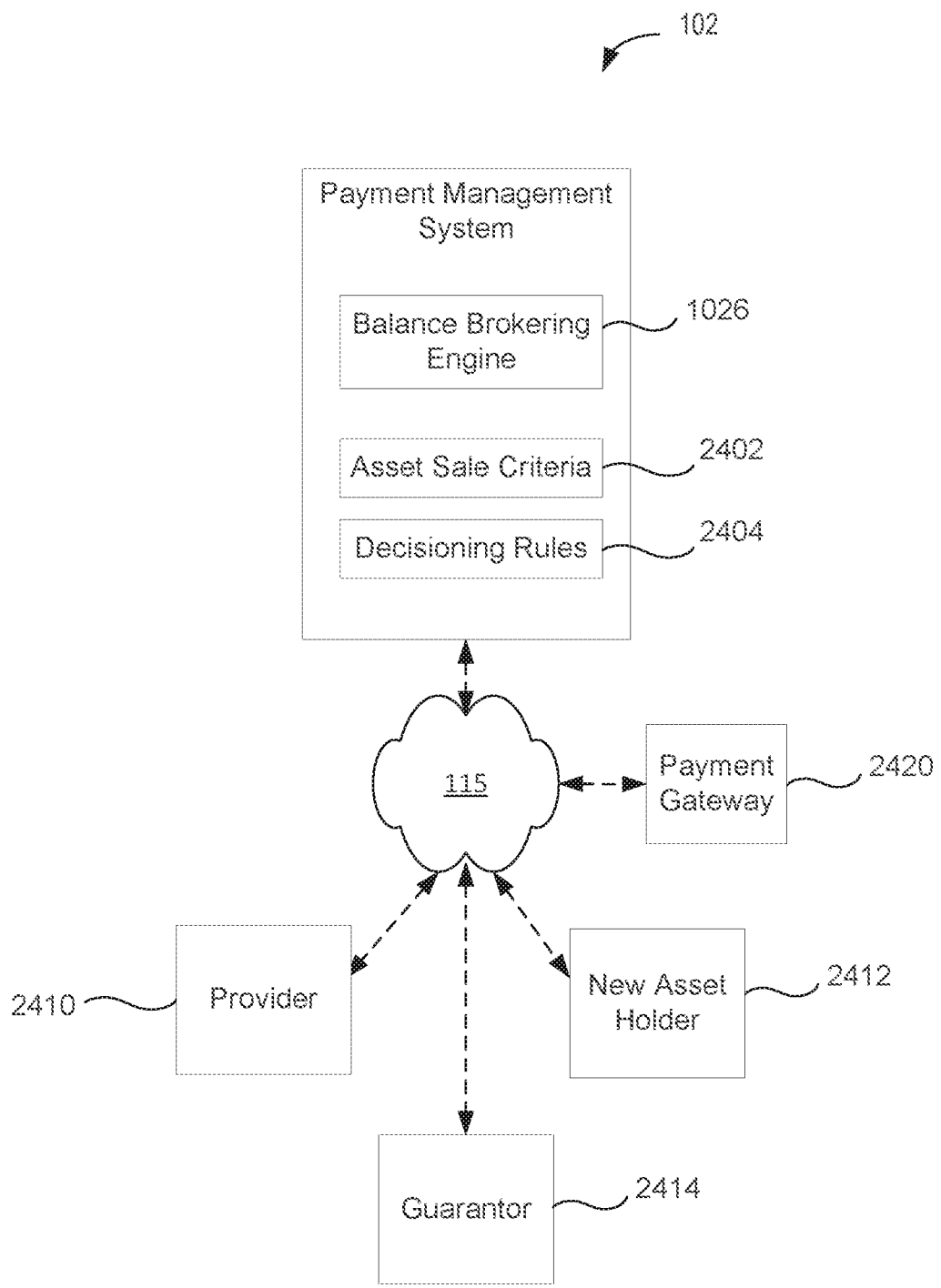
FIG. 24 is a diagram of a payment management system brokering a balance, according to one embodiment.

FIG. 24 is a diagram of a payment management system 102 brokering a balance, according to one embodiment. The payment management system 102 may include a balance brokering engine 1026 that may implement the method of FIG. 23 to transfer an open charges balance from a provider 2410 to a new asset holder 2412. The payment management system 102 may enable configuration of asset sale criteria 2402 to determine whether an open charges balance is eligible for transfer. The balance brokering engine considers decisioning rules 2404 to present financing options to the guarantor 2414 of the open charges balance. The decisioning rules may be configured by the provider 2410 or the new asset holder 2412 as appropriate. If the open charges balance is transferable, and if the guarantor 2414 accepts a financing option, the balance brokering engine can effectuate transfer of the asset to the new asset holder 2412. The payment management system 102 may communicate with the provider 2410, the new asset holder 2412, and the guarantor 2414 over a network 115, such as the Internet. The payment management system 102 may effectuate electronic transactions over the network 115. A payment gateway 2420 may facilitate electronic transactions to transfer the asset to the new asset holder.

After an asset (e.g., open charges balance) is transferred to the new asset holder 2412, charges for a subsequent period are aggregated to a new open charges balance and can be used as a basis for a new asset decisioning/brokering by the balance brokering engine 1026. As an example, January's visits of $200 may be eligible for a purchase by the new asset holder 2412 and may be transferred to a new system of record of the new asset holder 2412, according to pre-arranged asset purchase terms (e.g. 5% discount and non-recourse). February's visits of $1000 are also eligible for asset transfer, but the larger balance may warrant a steeper discount or move the asset to a full recourse model (e.g. 10% discount and full recourse back to the provider in the event of a guarantor default) held by yet another asset holder. In March, the guarantor 2414 may tally $100K in charges due to birth of premature baby. This balance may not qualify for asset transfer. Instead, the terms of the provider 2410 are offered and the payment management system 102 may simply remain a servicer of the account of the guarantor 2414. The guarantor's statement in April may show any new charges for that month, plus an amount due to the new asset holder 2412 for the January loan and an amount due to the second new asset holder for the February loan, and the amount due to the provider 2410 for the March loan plus the amount due for April charges. All of the amounts due for the several financings may be summed to one debit against the guarantor's bank account and the payment management system 102 may split the payment between the various entities (provider 2410 and new asset holder 2412) and allocate appropriate amounts to interest and principle.

EXAMPLE EMBODIMENTS

Some examples of embodiments of adaptive natural language interfaces and other adaptive output systems are provided below.

Example 1

A system for managing payments for services, comprising: one or more processors; a memory in electrical communication with the one or more processors to store first visit data tracked by a first billing system, the first visit data specifying one or more visit charges incurred during a time period, each of the one or more visit charges incurred for a visit; a visits engine to compile the one or more visit charges into a current batch of open charges and generate an open charges balance by aggregating all open charges of the current batch of open charges; a balance brokering engine to evaluate the open charges balance based on asset sales criteria for determining whether the open charges balance should be transferred from the first billing system to a new system of record and effectuate electronic transactions to transfer title of an accounts receivable asset that constitutes rights to collect payment for the open charges balance, including payment for the current batch of open charges, to the new system of record, if the asset sales criteria are met; and wherein the system tracks the open charges balance, including payments to pay the one or more visit charges and other transactions relating to the open charges balance, wherein the system tracks the open charges balance separate from the first billing system and tracks transactions tracked in the first billing system that pertain to the one or more visit charges.

Example 2

The system of Example 1, further comprising an extraction engine to extract the first visit data from the first billing system and to generate a single longitudinal portrayal including the first visit data and the second visit data.

Example 3

The system of Example 1, further comprising a payment clearance and routing engine to interface with a payment gateway to effectuate electronic transactions to transfer the title of the accounts receivable asset.

Example 4

The system of Example 1, wherein the balance brokering engine is configured to effectuate the transactions to transfer title of the accounts receivable asset to the new system of record by: debiting the open charges balance from a financial institution account associated with the new system of record; crediting the open charges balance to a financial institution account associated with the first billing system.

Example 5

The system of Example 1, wherein the asset sales criteria are defined by a provider associated with the first billing system.

Example 6

The system of Example 1, wherein the asset sales criteria are defined by a potential new asset holder associated with the new system of record to which the open charges balance is transferred if the asset sales criteria are met.

Example 7

The system of Example 1, wherein the system is the new system of record.

Example 8

The system of Example 1, wherein the new system of record is a third-party system, remote from the payment management system and coupled to the system management system over a communication network.

Example 9

A computer-implemented method for managing payments for a benefit, such as a product or service, the method comprising: receiving, at a payment management system comprising one or more computing devices, visit data being tracked by a first billing system and specifying one or more visit charges, each of the one or more visit charges including one or more charges incurred for a visit during a time period; compiling the one or more visit charges for the time period into a current batch of open charges; generating an open charges balance by aggregating all open charges of the current batch of open charges; evaluating the open charges balance, by the payment management system, based on one or more pre-defined asset sales criteria to determine whether the open charges balance should be transferred to a new system of record; if the one or more asset sales criteria are met, automatically effectuating by the payment management system electronic transactions to transfer title of an accounts receivable asset that constitutes all rights to collect payment for the open charges balance, including payment for the current batch of open charges, to an entity associated with the new system of record; and tracking, at the payment management system, transactions relating to the open charges balance, including payments to pay the current batch of open charges, the tracking being separate from the first billing system.

Example 10

The method of Example 9, wherein effectuating transactions to transfer title of the accounts receivable asset to the new system of record comprises communicating a transaction request to a payment gateway to request the payment gateway: debiting the open charges balance from a financial institution account associated with the new system of record; crediting the open charges balance to a financial institution account associated with the first billing system.

Example 11

The method of Example 9, further comprising: compiling into the current batch of open charges one or more additional transactions that relate to the one or more visit charges, the one or more additional transactions including additional transactions that adjust at least one of the one or more visit charges in the current batch of open charges adjust a gross batch balance that is a sum of the one or more visit charges, wherein generating the open charges balance comprises aggregating all open charges of the current batch of open charges, including the one or more additional transactions.

Example 12

The method of Example 11, wherein the additional transactions include one or more of: an interest charge based on an amount owing for one or more past open charges balances; a system of record fee; a payment from an insurance provider to be deducted in aggregating all the open charges of the current batch of open charges; a provider adjustment to a visit charge; and a removal of a disputed visit charge.

Example 13

The method of Example 11, wherein effectuating transactions to transfer title of the accounts receivable asset to the new system of record comprises communicating a transaction request to a payment gateway to request the payment gateway: debiting each of the current open charges from a financial institution account associated with the new system of record; crediting each of the one or more open charges to a financial institution account associated with the first billing system with.

Example 14

The method of Example 9, wherein the one or more asset sales criteria include system criteria that are pre-defined by a payment management system administrator.

Example 15

The method of Example 14, wherein the system criteria include a propensity to pay score.

Example 16

The method of Example 9, wherein the one or more asset sales criteria include provider criteria that are pre-defined by a provider of a visit of the one or more visit charges.

Example 17

The method of Example 16, further comprising receiving, at the payment management system the one or more provider criteria.

Example 18

The method of Example 9, wherein the asset sales criteria are defined by a potential new asset holder associated with the new system of record to which the open charges balance is transferred if the asset sales criteria are met.

Example 19

The method of Example 9, further comprising: receiving, at the payment management system, data specifying a payment vehicle for paying a payment amount; communicating a transaction request to a payment gateway to request the payment gateway debit payment funds in the payment amount from a payor financial institution associated with the payment vehicle and credit at least a portion of the payment funds to a payee financial institution associated with the new system of record, in payment toward the batch balance; and communicating an electronic posting file to notify the new system of record of transfer of at least at portion of the payment funds in payment toward the open charges balance.

Example 20

The method of Example 19, further comprising: receiving at the one or more computing devices payment option input specifying provider pre-determined payment options; receiving at the one or more computing devices a selection of one of the provider pre-determined payment options; and determining the payment amount based on the selected one of the provider pre-determined payment options.

Example 21

The method of Example 9, further comprising: receiving, at the payment management system, second visit data being tracked in a second billing system and specifying one or more second visit charges, each of the one or more second visit charges including one or more charges incurred for a visit during the time period; and compiling the one or more second visit charges for the time period into the current batch of open charges, wherein generating the open charges balance comprises aggregating all open charges of the current batch of open charges, including the one or more second visit charges, thereby aggregating visit charges for the time period that are tracked in multiple billing systems.

Example 22

The method of Example 21, wherein the second visit data is received from the second billing system, wherein the second billing system is remote from the one or more computing devices.

Example 23

The method of Example 21, wherein the one or more visit charges includes a visit charge for a first visit of a beneficiary, wherein the one or more second visit charges includes a visit charge for a second visit of a second beneficiary.

Example 24

The method of Example 9, wherein the time period comprises an initial time period and the current batch of open charges comprises a first batch of open charges, the method further comprising: receiving, at the payment management system, second visit data being tracked in the first billing system and specifying one or more second visit charges, each of the one or more second visit charges including one or more charges incurred for a visit during a second time period distinct from to the initial time period; compiling the one or more second visit charges for the second time period into a second batch of open charges; generating a second open charges balance by aggregating all open charges of the second batch of open charges; wherein the second open charges balance is maintained separate from the first open charges balance; evaluating the second open charges balance, by the payment management system, based on the asset sales to determine whether the second open balance should be transferred to a new system of record; if the asset sales criteria are not met, maintaining title of an accounts receivable asset that constitutes all rights to collect payment for the second open charges balance, including payment for the second batch of open charges, at the first billing system, wherein the first billing system remains as a system of record; and tracking, at the payment management system, transactions relating to the second open charges balance, including payments to pay the second batch of open charges, the tracking being separate from the first billing system, the tracking including transactions tracked in the first billing system that pertain to the one or more second visit charges.

Example 25

The method of Example 24, wherein a visit charge of the first visit data specifies a charge for a first visit of a beneficiary, wherein a visit charge of the second visit data specifies a charge for a second visit of a second beneficiary.

Example 26

The method of Example 24, wherein the first visit is a first healthcare visit, the second visit is a second healthcare visit, and the beneficiary is a patient.

Example 27

The method of Example 24, wherein the first visit is a first healthcare visit of a first beneficiary and the second visit is a second healthcare visit of a second beneficiary.

Example 28

The method of Example 9, wherein the new system of record is the payment management system.

Example 29

The method of Example 9, wherein the new system of record is a third-party system, remote from the payment management system and coupled to the payment management system over a communication network.

Example 30

A system for managing payments, comprising: one or more processors; a memory in electrical communication with the one or more processors to store first visit data tracked by a first billing system, the first visit data specifying one or more visit charges incurred during a time period, each of the one or more visit charges incurred for a visit; a visits engine to compile the one or more visit charges into a current batch of open charges and generate an open charges balance by aggregating all open charges of the current batch of open charges; a financing engine to: present, to a guarantor of the one or more visit charges, pre-determined payment options for paying the open charges balance, each of the pre-determined payment options including terms at least partially defined by one of a present asset holder and a potential asset holder of the open charges balance; receive, at the payment management system, a guarantor selection of one of the pre-determined payment options for paying the open charges balance; and determine a payment amount based on the selected one of the pre-determined payment options.

Example 31

The system of Example 30, wherein the present asset holder is a provider of one or more visits of the of the current batch of visit charges.

Example 32

The system of Example 30, further comprising: a payment portal to receive payment data specifying a payment vehicle for paying a payment amount; and a payment and clearance routing engine to: transmit a transaction request to a payment gateway to request the payment gateway to obtain funds in the payment amount from a payor financial institution associated with the payment vehicle, to transfer a first portion of the payment funds to a payee financial institution associated with the first patient billing system, and to transfer a second portion of the payment funds to a payee financial institution associated with the second patient billing system; and communicate one or more electronic posting files to notify the first patient billing system of transfer of the first portion of the payment funds toward payment of the charge for the first visit and to notify the second patient billing system of transfer of the second portion of the payment funds toward payment of the charge for the second visit.

Example 33

The system of Example 30, wherein the system tracks the open charges balance, including payments to pay the one or more visit charges and other transactions relating to the open charges balance, wherein the system tracks the open charges balance separate from the first billing system and tracks transactions tracked in the first billing system that pertain to the one or more visit charges.

Example 34

The system of Example 30, wherein the pre-determined payment options include a complete resolution option to make a single payment in satisfaction of the open charges balance, wherein if the guarantor selection of one of the provider pre-determined payment options selects the complete resolution option, then the financing engine determines the payment amount by: checking for a pre-determined payment discount specified as a term of the complete resolution option; and determining the payment amount as the open charges balance net of the prompt payment discount.

Example 35

The system of Example 30, wherein the pre-determined payment options include a guarantor-configured financing option allowing the guarantor to request one or more financing terms, the guarantor-configured financing option including authorized financing terms at least partially defined by the one of the present asset holder and the potential asset holder of the open charges balance, wherein if the guarantor selection of one of the provider pre-determined payment options selects the guarantor-configured financing option, then the financing engine determines the payment amount by: receiving a guarantor request for one or more financing terms for financing the open charges balance; comparing a guarantor requested financing term to the authorized financing terms; generating an financing offer, based on the guarantor requested terms and the authorized financing terms; and determining the payment amount based on terms of the authorized offer of financing.

Example 36

The system of Example 35, wherein the financing engine determines the guarantor-configured financing option that is presented to the guarantor based on decisioning rules configured by the one of the present asset holder and the potential asset holder of the open charges balance, each decisioning rule specifying authorized financing terms for a group of one or more guarantors that satisfy criteria of the decisioning rule.

Example 37

The system of Example 30, wherein the provider pre-determined payment options include a pre-set financing option including pre-set financing terms at least partially defined by the one of the present asset holder and the potential asset holder of the open charges, wherein, if the selection of one of the provider pre-determined payment options selects the pre-set financing option, then the financing engine determines the payment amount by one of: determining a minimum payment amount in compliance with the terms of the pre-set financing option, if the pre-set financing option comprises open-ended credit financing; and amortizing the open charges balance into regular periodic payments, based on the pre-set financing terms, and determining the payment amount as a first regular periodic payment of the regular periodic payments, if the pre-set financing option comprises installment loan financing.

Example 38

The system of Example 37, wherein the pre-set financing terms of the pre-set financing option that is presented to the guarantor are determined based on decisioning rules configured by the one of the present asset holder and the potential asset holder of the open charges balance, each decisioning rule specifying the terms of the pre-set financing option for a group of one or more guarantors that satisfy criteria of the decisioning rule.

Example 39

The system of any of Examples 30-38, wherein the financing engine is configured to determine the payment amount by summing a current payment amount with payments due for financing one or more prior open charges balances, the current payment amount being the payment amount determined based on the selected one of the pre-determined payment options for the open charges balance of the current batch of open charges, the payments due for financing one or more prior open charges balances each determined based on a previously selected pre-determined payment option for a corresponding prior open charges balance.

Example 40

A computer-implemented method for managing payments, the method comprising: receiving, at a payment management system comprising one or more computing devices, first visit data that is tracked by a first billing system and specifying one or more visit charges incurred during a time period, each of the one or more visit charges including one or more charges incurred for a visit; compiling the one or more visit charges for the time period into a current batch of open charges; generating an open charges balance by aggregating all open charges of the current batch of open charges; presenting, to a guarantor of the one or more visit charges, pre-determined payment options for paying the open charges balance, each of the pre-determined payment options including terms at least partially defined by one of a present asset holder and an eventual asset holder of the open charges balance; receiving, at the payment management system, a guarantor selection of one of the pre-determined payment options for paying the open charges balance; and determining a payment amount based on the selected one of the pre-determined payment options.

Example 41

The method of Example 40, wherein at least one of the one or more visit charges comprises an estimate of costs for the visit in advance of occurrence of the visit.

Example 42

The method of Example 40, further comprising: receiving, at the payment management system, data specifying a payment vehicle for paying the payment amount; communicating a transaction request to a payment gateway to request the payment gateway to debit payment funds from a payor financial institution associated with the payment vehicle and to credit at least a portion of the payment funds to a payee financial institution associated with the first billing system in payment toward the open charges balance; and communicating an electronic posting file to notify the first billing system of transfer of at least a portion of the payment funds in payment toward specific visit charges of the current batch of open charges.

Example 43

The method of Example 40, wherein the transaction request is also to request the payment gateway to credit at least a portion of the payment funds to the payee financial institution associated with the first billing system in payment toward one or more prior open charges balances.

Example 44

The method of Example 40, wherein the transaction request is also to request the payment gateway to credit at least a portion of the payment funds to the payee financial institution associated with the first billing system in payment toward only a past open charges balance.

Example 45

The method of Example 40, wherein the pre-determined payment options are at least partially configured by one or more of a present asset holder and an eventual asset holder of the open charges balance.

Example 46

The method of Example 45, wherein the present asset holder is a provider of one or more visits of the current batch of visit charges.

Example 47

The method of Example 40, wherein the pre-determined payment options include a complete resolution option to make a single payment in satisfaction of the open charges balance, wherein if the selection of one of the provider pre-determined payment options selects the complete resolution option, then determining the payment amount comprises: checking for a pre-determined payment discount specified as a term of the complete resolution option, wherein presenting the predetermined payment options includes presenting such pre-determined prompt payment discount; and determining the payment amount as the open charges balance net of the prompt payment discount.

Example 48

The method of Example 47, wherein the payment discount varies according to a segmentation or grouping at one or more of a provider level, a guarantor level, and a visit level.

Example 49

The method of Example 47, wherein the payment discount comprises a prompt payment discount.

Example 50

The method of Example 40, wherein the pre-determined payment options include a guarantor-configured financing option allowing the guarantor to request one or more financing terms, the guarantor-configured financing option including authorized financing terms at least partially defined by one of a present asset holder and an eventual asset holder of the open charges balance, wherein if the guarantor selection of one of the pre-determined payment options selects the guarantor-configured financing option, then determining the payment amount comprises: receiving a guarantor request providing one or more guarantor requested financing terms for financing the open charges balance; comparing the one or more guarantor requested financing terms to the authorized financing terms; generating an authorized offer of financing, based on the guarantor requested terms and the authorized financing terms; and determining the payment amount based on terms of the authorized offer of financing.

Example 51

The method of Example 50, wherein the authorized offer provides installment loan financing terms, including an amortization of the open charges balance into multiple regular periodic payments, and wherein the payment amount is determined to be a first regular periodic payment provided by the amortization of the open charges balance.

Example 52

The method of Example 50, wherein the authorized offer provides open-ended credit financing terms specifying a minimum payment amount due, based on a percentage of the open charges balance, and wherein the payment amount is determined to be the minimum payment amount.

Example 53

The method of Example 50, wherein the guarantor-requested financing terms include one or more of: a financing type, including an installment loan type or a revolving credit type; a desired number of periods for payment over which recurring payments will be made to complete payment of the open charges balance; a desired interest rate; an interest rate type, including a fixed interest rate or a variable interest rate; a period payment amount; and a minimum payment amount.

Example 54

The method of Example 50, wherein the authorized financings terms comprise one or more of: a financing type, including an installment loan type or a revolving credit type; a minimum payment amount; a maximum amortization period; a minimum interest rate; an interest rate type, including a fixed interest rate or a variable interest rate; interest rate tranches; an interest free period; a credit limit for open charges; interest bearing or non-interest bearing; a prompt payment discount; a charity (or hardship) discount; a pre-payment discount; and a self-pay discount.

Example 55

The method of Example 50, wherein the guarantor-configured financing option, including the authorized financing terms, that is presented to the guarantor is determined based on decisioning rules configured by the one of the present asset holder and the eventual asset holder of the open charges balance, each decisioning rule specifying authorized financing terms for a group of one or more guarantors that satisfy criteria of the decisioning rule.

Example 56

The method of Example 55, wherein the criteria of each decisioning rule group the guarantor at one or more of a provider level, a guarantor level, and a visit level.

Example 57

The method of Example 55, wherein provider-level criteria of a decisioning rule group the guarantor according to one or more provider characteristics, such that the authorized financing terms of the guarantor-configured financing option depend on a visit provider for the one or more visit charges.

Example 58

The method of Example 55, wherein provider-level criteria of a decisioning rule group the guarantor according to one or more provider characteristics, such that a first set of authorized financing terms is presented to a guarantor for visit charges incurred from visits to a first provider and a second set of authorized financing terms is presented for visit charges incurred from visits to a second provider.

Example 59

The method of Example 55, wherein guarantor-level criteria of a decisioning rule group the guarantor according to one or more characteristics of the guarantor, including but not limited to: a propensity to pay score; a credit score; an income estimate; a size of household estimate; an ability to pay score; a total amount presently owing to one or more providers; a location (e.g., residence) of the guarantor; a physical characteristics of the guarantor (e.g., height, weight, blood pressure); and a type of insurance held by a guarantor.

Example 60

The method of Example 55, wherein visit-level criteria of a decisioning rule group the guarantor according to one or more characteristics of the one or more visits, including but not limited to: a visit charge amount; an open charges balance; an age of the open charges; a location of the visit; and a visit benefit to a beneficiary of the visit.

Example 61

The method of Example 40, wherein the pre-determined payment options include a pre-set financing option including pre-set financing terms at least partially defined by one of a present asset holder and an eventual asset holder of the open charges, wherein, if the guarantor selection of one of the pre-determined payment options selects the pre-set financing option, then determining the payment amount comprises one of: determining a minimum payment amount in compliance with the terms of the pre-set financing option, if the pre-set financing option comprises open-ended credit financing; and amortizing the open charges balance into regular periodic payments, based on the pre-set financing terms, and determining the payment amount as a first regular periodic payment of the regular periodic payments, if the pre-set financing option comprises installment loan financing.

Example 62

The method of Example 61, wherein the pre-set financing terms of the pre-set financing option include one or more of: a financing type, including an installment loan type or a revolving credit type; a number of periods for payment over which recurring payments will be made to complete payment of the open charges balance; an interest rate; an interest rate type, including a fixed interest rate or a variable interest rate; a period payment amount; a minimum payment amount; interest rate tranches; an interest free period; a credit limit for open charges; interest bearing or non-interest bearing; a prompt payment discount; a charity (or hardship) discount; a pre-payment discount; and a self-pay discount.

Example 63

The method of Example 61, wherein the pre-set financing terms of the pre-set financing option that is presented to the guarantor are determined based on decisioning rules configured by the one of the present asset holder and eventual asset holder of the open charges balance, each decisioning rule specifying the terms of the pre-set financing option for a group of one or more guarantors that satisfy criteria of the decisioning rule.

Example 64

The method of Example 63, wherein the criteria of each decisioning rule group the guarantor at one or more of a provider level, a guarantor level, and a visit level.

Example 65

The method of Example 63, wherein provider-level criteria of a decisioning rule group the guarantor according to one or more provider characteristics, such that the terms of the pre-set financing option depend on a visit provider for the one or more visit charges.

Example 66

The method of Example 63, wherein provider-level criteria of a decisioning rule group the guarantor according to one or more provider characteristics, such that the pre-set financing option includes a first set of terms for visit charges incurred from visits to a first provider and includes an alternate second set of terms is presented for visit charges incurred from visits to a second provider.

Example 67

The method of Example 63, wherein the guarantor-level criteria of a decisioning rule group the guarantor according to one or more characteristics of the guarantor, including but not limited to: a propensity to pay score; a credit score; an income estimate; a size of household estimate; an ability to pay score; a total amount presently owing to one or more providers; a location (e.g., residence) of the guarantor; a physical characteristics of the guarantor (e.g., height, weight, blood pressure); and a type of insurance held by a guarantor.

Example 68

The method of Example 63, wherein visit-level criteria of a decisioning rule group the guarantor according to one or more characteristics of the one or more visits, including but not limited to: a visit charge amount; an open charges balance; an age of the open charges; a location of the visit; and a visit benefit to a beneficiary of the visit.

Example 69

The method of any of Example 40-68, wherein determining the payment amount further comprises summing a current payment amount with payments due for financing one or more prior open charges balances, the current payment amount being the payment amount determined based on the selected one of the pre-determined payment options for the open charges balance of the current batch of open charges, the payments due for financing one or more prior open charges balances each determined based on a previously selected pre-determined payment option for a corresponding prior open charges balance of a prior batch of open charges.

Example 70

The method of Example 69, wherein each of the payments due for financing one or more prior open charges balances is determined according to a next regular periodic payment for an amortization of a prior open charges balance for a previous time period:

Example 71

The method of Example 40, further comprising: receiving, at the payment management system from a computing device of the one of the present asset holder and the eventual asset holder of the open charges balance, payment option input to at least partially define the terms of the pre-determined payment options.

Example 72

A computer-implemented method for managing payments, the method comprising: receiving, at a payment management system comprising one or more computing devices, charge data specifying one or more charges; compiling the one or more charges into a current batch of open charges; generating an open charges balance by aggregating all open charges of the current batch of open charges; presenting to a guarantor of the one or more charges pre-determined payment options for paying the open charges balance, each of the pre-determined payment options including terms at least partially defined by one of a present asset holder and a potential asset holder of the open charges balance; receiving, at the payment management system, a guarantor selection of one of the pre-determined payment options for paying the open charges balance; and determining a payment amount based on the selected one of the provider pre-determined payment options.

Example 73

The method of Example 72, wherein at least one of the one or more charges comprises an estimate of a charge for a benefit to occur.

Example 74

The method of Example 73, wherein the benefit is to occur during a future time period.

Example 75

The method of Example 72, wherein the pre-determined payment options include a guarantor-configured financing option allowing the guarantor to request one or more financing terms, the guarantor-configured financing option including authorized financing terms at least partially defined by one of a present asset holder and a potential asset holder of the open charges balance, wherein if the selection of one of the pre-determined payment options selects the guarantor-configured financing option, then determining the payment amount comprises: receiving a guarantor request for one or more financing terms for financing the open charges balance; comparing a guarantor requested financing term to the authorized financing terms; generating an authorized offer of financing, based on the guarantor requested terms and the authorized financing terms; and determining the payment amount based on terms of the authorized offer of financing.

Example 76

The method of Example 75, wherein the guarantor-configured financing option that is presented to the guarantor is determined based on decisioning rules configured by the one of the present asset holder and the potential asset holder of the open charges balance, each decisioning rule specifying authorized financing terms for a group of one or more guarantors that satisfy criteria of the decisioning rule.

Example 77

The method of Example 72, wherein the pre-determined payment options include a pre-set financing option including pre-set financing terms at least partially defined by one of a present asset holder and an eventual asset holder of the open charges, wherein, if the guarantor selection of one of the pre-determined payment options selects the pre-set financing option, then determining the payment amount comprises one of: determining a minimum payment amount in compliance with the terms of the pre-set financing option, if the pre-set financing option comprises open-ended credit financing; and amortizing the open charges balance into regular periodic payments, based on the pre-set financing terms, and determining the payment amount as a first regular periodic payment of the regular periodic payments, if the pre-set financing option comprises installment loan financing.

Example 78

The method of Example 77, wherein the pre-set financing terms of the pre-set financing option that is presented to the guarantor are determined based on decisioning rules configured by the one of the present asset holder and the potential asset holder of the open charges balance, each decisioning rule specifying the terms of the pre-set financing option for a group of one or more guarantors that satisfy criteria of the decisioning rule.

Example 79

A system for managing payments for healthcare services, comprising: one or more processors; a memory in electrical communication with the one or more processors, the memory to store historical healthcare data including healthcare transaction data tracked by a first billing system, the historical healthcare data pertaining to one or more guarantors; a scoring engine configured to extract propensity-to-pay ("PTP") characteristics from the historical healthcare data, including PTP characteristics of the one or more guarantors, and calculate a PTP metric for a guarantor based on PTP characteristics of the guarantor extracted from the historical healthcare data, wherein the PTP metric indicates a likelihood that the guarantor will pay for visit charges for healthcare visits.

Example 80

The system of Example 79, wherein the PTP metric comprises a PTP score.

Example 81

The system of Example 80, wherein the scoring engine comprises a plurality of calculation engines, each configured to calculate a respective type of PTP score for a guarantor.

Example 82

The system of Example 81, wherein the plurality of calculation engines differ with respect to one or more of a weighting and a combination of algorithms used to calculate a PTP score.

Example 83

The system of Example 79, wherein the PTP metric is a group identifier that groups a guarantor into a group having an associated propensity-to-pay a visit charge for a healthcare visit.

Example 84

The system of Example 79, further comprising: a staging module to determine a current stage of an account record of the guarantor, based on the historical healthcare data, wherein the scoring engine calculates the PTP metric for the guarantor based on the stage of the account record of the guarantor.

Example 85

The system of Example 86, wherein the staging module comprises a trigger engine configured to implement one or more triggered actions in response to one or more of: assigning a stage to an account record; updating data pertaining to an account record; and a request for updated stage assignment information.

Example 86

The system of Example 79, the memory to further store first visit data that is tracked by a first billing system and specifying one or more visit charges incurred during a time period, each of the one or more visit charges incurred for a visit, the system further comprising: a visits engine to aggregate, collect, or compile the one or more visit charges into a current batch of open charges and generate an open charges balance by aggregating all open charges of the current batch of open charges, wherein the scoring engine calculates the PTP metric for the guarantor with respect to the open charges balance, such that the PTP metric indicates a likelihood that the guarantor will pay for the open charges balance.

Example 87

The system of Example 86, further comprising: a financing engine to: present, to a guarantor of the one or more visit charges, pre-determined payment options for paying the open charges balance, each of the pre-determined payment options including terms at least partially defined by an asset holder of the open charges balance; receive, at the payment management system, a guarantor selection of one of the pre-determined payment options for paying the open charges balance; and determine a payment amount based on the guarantor selected one of the pre-determined payment options.

Example 88

The system of Example 87, wherein each of the pre-determined payment options include one or more terms defined by one of a present asset holder and an eventual asset holder of the open charges balance, wherein the one or more terms depend on the PTP score of the guarantor.

Example 89

The system of Example 79, wherein the historical healthcare data includes healthcare transaction data tracked by a second billing system.

Example 90

The system of Example 79, the memory further to store credit reporting data from one or more third party credit reporting sources, wherein the scoring engine calculates the PTP metric for the guarantor based on both the PTP characteristics and the credit reporting data.

Example 91

The system Example 90, wherein the scoring engine is configured to extract an ability-to-pay (ATP) metric from the credit reporting data, and wherein the scoring engine calculates the PTP metric based on the PTP characteristics and the ATP metric.

Example 92

The system of Example 91, further comprising: a charity evaluation module configured to calculate a charity score for a guarantor based on the PTP metric and the ATP metric.

Example 93

A computer-implemented method for managing payments for healthcare services, the method comprising: aggregating, compiling or collecting, at a payment management system comprising one or more computing devices, historical healthcare data including healthcare transaction data tracked by a first billing system, the historical healthcare data pertaining to healthcare visits of patients, whose visit charges are guaranteed by one or more guarantors; extracting propensity-to-pay ("PTP") characteristics from the historical healthcare data, including PTP characteristics of the one or more guarantors; calculating a PTP metric for a first guarantor of the one or more guarantors based on PTP characteristics of the first guarantor extracted from the historical healthcare data, the PTP metric indicating a likelihood that the first guarantor will pay for visit charges for healthcare visits.

Example 94

The method of Example 93, wherein the healthcare transaction data includes billing transaction records, payment transaction records, and/or financing plan records associated with an account record of one or more of the first guarantor and a first patient associated with the first guarantor, the account record maintained by the payment management system.

Example 95

The method of Example 93, wherein the healthcare transaction data includes billing transaction records, payment transaction records, and/or financing plan records associated with visit charges of a patient associated with the first guarantor.

Example 96

The method of Example 95, wherein the patient is the first guarantor.

Example 97

The method of Example 93, wherein the healthcare transaction data includes healthcare transaction action data for a second guarantor whose account record is linked to the account record of the first guarantor.

Example 98

The method of Example 97, further comprising calculating a PTP metric for the second guarantor based on PTP characteristics of the second guarantor extracted from the historical healthcare data, the PTP metric indicating a likelihood that the second guarantor will pay for visit charges.

Example 99

The method of Example 93, wherein the PTP metric is calculated based on PTP characteristics of the first guarantor that are inferred from PTP characteristics of one or more different guarantors of the one or more guarantors that are calculated as being similar to the first guarantor.

Example 100

The method of Example 93, wherein the historical healthcare data includes healthcare condition data, including information pertaining to a healthcare condition of a patient associated with the guarantor.

Example 101

The method of Example 100, wherein the healthcare condition data includes one or more of diagnoses, disease conditions, chronic health condition(s), degenerative conditions.

Example 102

The method of Example 101, wherein the healthcare condition data is derived at least partially from billing transaction information included in the healthcare transaction data tracked by the first billing system, the billing transaction information including one or more of treatment codes and diagnostic codes.

Example 103

The method of Example 101, wherein the healthcare condition data is derived at least partially from healthcare records of the patient maintained by a healthcare service provider associated with the first billing system and providing healthcare services to the patient.

Example 104

The method of Example 93, wherein the historical healthcare data includes healthcare transaction data tracked by a second billing system.

Example 105

The method of Example 93, wherein the historical healthcare data includes healthcare transaction data tracked by a plurality of billing systems in addition to the first billing system.

Example 106

The method of c Example 93, further comprising: receiving credit reporting data from one or more third-party credit reporting sources; calculating the PTP metric for the guarantor based on both the PTP characteristics and the credit reporting data.

Example 107

The method of Example 106, wherein the credit reporting data is reported to the one or more third-party credit reporting sources by third-party credit grantors, the credit reporting data including one or more of: types of credit extended to the guarantor; a length of time the guarantor's credit accounts have been open; timeliness of guarantor payments to lenders; amount of credit extended to the guarantor; whether new sources of credit are being actively sought by the guarantor; one or more credit scores of the guarantor, each credit score summarizing credit risk of the guarantor; a net worth estimate; an income estimate; and a size of household estimate.

Example 108

The method of Example 107, wherein the one or more credit scores include one or more of a general credit score.

Example 109

The method of claim Example 108, wherein the general credit score is a FICO score.

Example 110

The method of Example 108, wherein the one or more credit scores include one or more industry-specific credit scores, including but not limited to credit scores of: the telecommunications industry; the healthcare industry; and the retail industry.

Example 111

The method of Example 93, wherein the PTP characteristics include one or more of: an average time to payment for healthcare transactions; late payments; payment amounts; insurance coverage; copayments; flexible spending account activity (e.g., estimated remaining balance); healthcare spending account activity; financing plan history (e.g., whether the patient and/or guarantor(s) have used a financing plan to pay for services and/or whether the payments were made in a timely manner); a total amount presently owed to a provider; prior bad debt charge-offs; prior hardship program assistance (charity); time periods between transactions; and dispute history.

Example 112

The method of Example 93, further comprising: receiving, at a payment management system, first visit data that is tracked by a first billing system and that specifies one or more visit charges each incurred for a visit to a healthcare provider, wherein the PTP score for the guarantor is calculated for a visit charge of the one or more visit charges that is guaranteed by the guarantor.

Example 113

The method of Example 93, further comprising: receiving, at a payment management system, an estimate of one or more visit charges for a visit to a healthcare provider, wherein the PTP score for the guarantor is calculated for the estimate of one or more visit charges.

Example 114

The method of Example 93, further comprising: receiving, at a payment management system, first visit data that is tracked by a first billing system and that specifies one or more visit charges incurred during a time period for a visit to a healthcare provider, each of the one or more visit charges guaranteed by the guarantor; compiling the one or more visit charges for the time period into a current batch of open charges; and generating an open charges balance by aggregating all open charges of the current batch of open charges, wherein the PTP metric for the guarantor is calculated for the open charges balance.

Example 115

The method of Example 114, wherein the PTP metric comprises a PTP score.

Example 116

The method of Example 115, wherein the PTP score for the guarantor is calculated for the open charges balance based on integrating PTP scores for each of the one or more visit charges of the batch of open charges.

Example 117

The method of Example 115, further comprising: generating a guarantor group identifier based on the PTP score; and providing the guarantor group identifier to the first billing system.

Example 118

The method of Example 93, wherein the PTP metric comprises a guarantor group identifier.

Example 119

The method of Example 93, further comprising: receiving demographic data pertaining to the guarantor from one or more third-party demographics data sources and consumer data sources; calculating the PTP metric for the guarantor based on both the PTP characteristics and the demographics data.

Example 120

The method of Example 93, further comprising determining a current stage of the guarantor's account, wherein the PTP metric for the guarantor is calculated further based on the current stage of the guarantor's account.

Example 121

The method of Example 120, wherein determining a current stage of the guarantor's account comprises: detecting a staging event regarding the guarantor's account; and designating a stage of the guarantor's account in response to detecting the staging event.

Example 122

The method of Example 93, further comprising: providing the PTP metric to the first billing system; updating the PTP metric based on a subsequent healthcare data pertaining to one or more subsequent healthcare visits; and providing an updated PTP metric to the first billing system.

Example 123

A computer-implemented method for managing payments to a provider, the method comprising: aggregating, at a payment management system comprising one or more computing devices, historical transaction data tracked in a first billing system of a provider, the historical transaction data pertaining to encounters of beneficiaries with the provider, each of the beneficiaries guaranteed by a guarantor of one or more guarantors; extracting payment characteristics from the historical transaction data, including payment characteristics of the one or more guarantors; calculating a payment score for a first guarantor of the one or more guarantors based on payment characteristics of the first guarantor extracted from the historical transaction data, the payment score summarizing a predication that the first guarantor is going to pay for charges for encounters.

Example 124

The method of Example 123, wherein the payment score comprises a propensity-to-pay (PTP) score providing indication of a likelihood that the first guarantor will pay for charges for encounters.

Example 125

The method of Example 123, wherein the payment score comprises an ability-to-pay (ATP) score providing indication of a capacity of the first guarantor to pay for charges for encounters.

Example 126

The method of Example 123, wherein the encounters comprise visits to a healthcare provider for healthcare services.

Example 127

The method of Example 123, wherein the encounters comprise encounters to purchase products from a provider.

Example 128

The method of Example 123, wherein the historical transaction data includes billing transaction records, payment transaction records, and/or financing plan records associated with charges of an encounter of a beneficiary who is associated with the first guarantor.

Example 129

The method of Example 128, wherein the beneficiary is the first guarantor.

Example 130

A system for managing payments for services, comprising: one or more processors; a memory in electrical communication with the one or more processors to store first visit data specifying a first visit charge pertaining to a first visit for which a first guarantor is responsible and to store second visit data specifying a second visit charge pertaining to a second visit for which a second guarantor is responsible, wherein the first visit data is tracked in a first billing system; a linking engine to receive a request to link an account of the first guarantor to the account of the second guarantor, provide an electronic notice of the request, receive indication of acceptance of the request, and to link the account of the first guarantor to the account of the second guarantor; a visits engine to aggregate the first visit data pertaining to the first visit charge with the second visit data pertaining to an account of the second guarantor; a statement engine to provide to the second guarantor an electronic statement including information from the first visit data pertaining to the first visit charge of the first guarantor aggregated with information from the second visit data pertaining to the second visit charge of the second guarantor.

Example 131

The system of Example 130, wherein the second visit data is tracked in the first billing system.

Example 132

The system of Example 130, wherein the second visit data is received from and tracked in a second billing system on one or more computers remote from the payment management system and coupled to the payment management system over a network.

Example 133

The system of Example 130, further comprising a payment clearance and routing engine to receive payment data specifying a payment vehicle for paying a payment amount, communicate one or more transaction requests to process an electronic financial transaction to obtain payment funds in the payment amount from a payor financial institution associated with the payment vehicle and to transfer a first portion of the payment funds to a payee financial institution associated with associated with a provider of the first visit, and communicate one or more electronic posting files to notify the account of the first guarantor of transfer of the first portion of the payment funds toward payment of the charge for the first visit.

Example 134

The system of Example 130, wherein the linking engine automatically requests from each of the first guarantor and the second guarantor a digitally signed release in compliance with externally imposed rules to protect information, wherein the linking engine receives the digitally signed release of each of the first guarantor and the second guarantor prior to the statement engine providing to the second guarantor information from the first visit data pertaining to the first visit charge.

Example 135

The system of Example 134, wherein the externally imposed rules to protect information comprise the Health Insurance Portability and Accountability Act.

Example 136

The system of Example 130, wherein the linking engine is further configured to receiving a request from one of the first guarantor and the second guarantor to unlink the account of the first guarantor from the account of the second guarantor, such that the second guarantor ceases to manage the account of the first guarantor on the payment management system, and unlink the account of the first guarantor from the account of the second guarantor, including removing from information pertaining to an account of the second guarantor information from the first visit data pertaining to the first visit charge, wherein the statement engine, upon the unlinking, provides to the second guarantor information pertaining to an account of the second guarantor on the payment management system, without information from the first visit data pertaining to the first visit charge.

Example 137

The system of Example 136, wherein unlinking the account of the first guarantor from the account of the second guarantor comprises maintaining in the account of the second guarantor information pertaining to payments initiated by the second guarantor toward visit charges of the first guarantor.

Example 138

A computer-implemented method for managing payments for services, the method comprising: receiving, at a payment management system comprising one or more computing devices, first visit data including a first visit charge pertaining to a first visit for which a first guarantor is responsible, the first visit charge including one or more charges incurred during the first visit; tracking the first visit charge in an account of the first guarantor on the payment management system; receiving at the payment management system a request of the first guarantor for a second guarantor to manage the account of the first guarantor on the payment management system; generating an electronic notice to the second guarantor of the request of the first guarantor; receiving at the payment management system an electronic indication of the second guarantor's acceptance of the request of the first guarantor; making the second guarantor a manager of the account of the first guarantor, based on the received indication of the second guarantor's acceptance, by linking the account of the first guarantor to the account of the second guarantor; and providing to the second guarantor information from the first visit data pertaining to the first visit charge, including an amount of the first visit charge, aggregated with information pertaining to an account of the second guarantor on the payment management system.

Example 139

The method of Example 138, wherein the first visit data is tracked in a first billing system associated with a provider of the first visit.

Example 140

The method of Example 139, wherein the first billing system is separate from the payment management system and the account of the first guarantor is tracked separately from tracking of the first visit data in the first billing system.

Example 141

The method of Example 139, wherein the first billing system is on the one or more computing devices of the payment management system.

Example 142

The method of Example 138, further comprising: populating the account of the first guarantor and the account of the second guarantor with information pertaining to the request of the first guarantor.

Example 143

The method of Example 142, further comprising: providing to a computing device of the first guarantor information pertaining to the account of the first guarantor, including information pertaining to the request of the first guarantor.

Example 144

The method of Example 142, further comprising: providing to a computing device of the second guarantor information pertaining to the account of the second guarantor, including information pertaining to the request of the first guarantor.

Example 145

The method of Example 138, further comprising: receiving, at the payment management system, second visit data including a second visit charge pertaining to a second visit for which the second guarantor is responsible; and tracking the second visit charge in the account of the second guarantor on the payment management system, wherein the information provided to the second guarantor also includes information from the first visit data pertaining to the second visit charge, including an amount of the second visit charge.

Example 146

The method of Example 145, wherein the first visit data and the second visit data are tracked in a first billing system associated with a provider of the first visit and a provider of the second visit.

Example 147

The method of Example 145, wherein the second visit data is tracked in a second billing system separate from the payment management system and the account of the second guarantor is tracked separately from tracking of the account of the second guarantor on the payment management system.

Example 148

The method of Example 147, wherein the second billing system is remote from the one or more computing devices of the payment management system and coupled to the payment management system over a network.

Example 149

The method of Example 145, further comprising: receiving, from a computing device of the second guarantor, input from the second guarantor pertaining to payment of the first visit charge and payment of the second visit charge.

Example 150

The method of Example 138, further comprising: receiving, from a computing device of the second guarantor, input from the second guarantor pertaining to payment of the first visit charge.

Example 151

The method of Example 138, wherein the first visit data includes a second visit charge pertaining to a second visit for which the first guarantor is responsible, the method further comprising: providing to the second guarantor information pertaining to the second visit charge, including an amount of the second visit charge with the information from the first visit data and the information pertaining to an account of the second guarantor; and receiving from a computing device of the second guarantor input from the second guarantor pertaining to payment for the second visit charge.

Example 152

The method of Example 138, wherein the request of the first guarantor for the second guarantor to manage the account of the first guarantor includes authorization for the second guarantor to receive and view the account information of the first guarantor.

Example 153

The method of Example 138, further comprising: receiving at the payment management system a request from one of the first guarantor and the second guarantor to unlink the account of the first guarantor from the account of the second guarantor, such that the second guarantor ceases to manage the account of the first guarantor on the payment management system; unlinking the account of the first guarantor from the account of the second guarantor, including removing from information pertaining to an account of the second guarantor information from the first visit data pertaining to the first visit charge; and providing to the second guarantor information pertaining to an account of the second guarantor on the payment management system, without information from the first visit data pertaining to the first visit charge.

Example 154

The method of Example 153, wherein unlinking the account of the first guarantor from the account of the second guarantor comprises maintaining in the account of the second guarantor information pertaining to payments initiated by the second guarantor toward visit charges of the first guarantor.

Example 155

The method of Example 138, further comprising: receiving at the payment management system payment data specifying a payment vehicle for paying a payment amount; communicating one or more transaction requests to process an electronic financial transaction to obtain payment funds in the payment amount from a payor financial institution associated with the payment vehicle and to transfer a first portion of the payment funds to a payee financial institution associated with associated with a provider of the first visit; and communicating one or more electronic posting files to notify the account of the first guarantor of transfer of the first portion of the payment funds toward payment of the charge for the first visit and to notify.

Example 156

The method of Example 155, wherein the transaction request is further to process an electronic transaction to transfer a second portion of the payment funds to a payee financial institution associated with a second billing system, and wherein the one or more electronic posting files are further to notify the second billing system of transfer of the second portion of the payment funds toward payment of the charge for the second visit.

Example 156

The method of Example 138, wherein making the second guarantor a manager of the account of the first guarantor comprises: automatically requesting from each of the first guarantor and the second guarantor a digitally signed release in compliance with externally imposed rules to protect information; and receiving the digitally signed release of each of the first guarantor and the second guarantor, prior to providing to the second guarantor information from the first visit data pertaining to the first visit charge.

Example 157

The method of Example 156, wherein the externally imposed rules to protect information comprise the Health Insurance Portability and Accountability Act.

Example 158

A computer-implemented method for managing payments for services, the method comprising: receiving, at a payment management system comprising one or more computing devices, first visit data including a first visit charge pertaining to a first visit for which a first guarantor is responsible, the first visit charge including one or more charges incurred during the first visit; tracking the first visit charge in an account of the first guarantor on the payment management system; receiving at the payment management system a request of a second guarantor to manage an account of the first guarantor on the payment management system; generating an electronic notice to the first guarantor of the request of the second guarantor; receiving at the payment management system an electronic indication of the first guarantor's acceptance of the request of the second guarantor; making the second guarantor a manager of the account of the first guarantor, based on the received indication of the first guarantor's acceptance, by linking the account of the first guarantor to the account of the second guarantor; and providing to the second guarantor information from the first visit data pertaining to the first visit charge, including an amount of the first visit charge, aggregated with information pertaining to an account of the second guarantor on the payment management system.

Example 159

The method of Example 158, the further comprising: receiving, at the payment management system, second visit data including a second visit charge pertaining to a second visit for which the second guarantor is responsible; and tracking the second visit charge in the account of the second guarantor on the payment management system, wherein the information provided to the second guarantor also includes information from the first visit data pertaining to the second visit charge, including an amount of the second visit charge.

Example 160

The method of Example 159, wherein the first visit data and the second visit data are tracked in a first billing system associated with a provider of the first visit and a provider of the second visit.

Example 161

The method of Example 159, wherein the second visit data is tracked in a second billing system separate from the payment management system and the account of the second guarantor is tracked separately from tracking of the account of the second guarantor on the payment management system.

Example 162

A system for managing payments for services, comprising: one or more processors; a memory in electrical communication with the one or more processors to store first visit data received from a first billing system and second visit data that is tracked by a second billing system that is independent from the first billing system, the first visit data specifying a charge for a first visit, and the second visit data specifying a charge for a second visit; a visits engine to aggregate the first visit data pertaining to the first visit charge with the second visit data pertaining to the second visit charge; a statement engine to provide a statement including information from the first visit data pertaining to the first visit charge aggregated with information from the second visit data pertaining to the second visit charge.

Example 163

The system of Example 162, further comprising: a payment portal to receive payment data specifying a payment vehicle for paying a payment amount; and a payment and clearance routing engine to: transmit a transaction request to a payment gateway to request the payment gateway to obtain funds in the payment amount from a payor financial institution associated with the payment vehicle, to transfer a first portion of the payment funds to a payee financial institution associated with the first patient billing system, and to transfer a second portion of the payment funds to a payee financial institution associated with the second patient billing system; and communicate one or more electronic posting files to notify the first patient billing system of transfer of the first portion of the payment funds toward payment of the charge for the first visit and to notify the second patient billing system of transfer of the second portion of the payment funds toward payment of the charge for the second visit.

Example 164

The system of Example 162, further comprising an extraction engine to extract the first visit data from the first billing system and to generate a single longitudinal portrayal including the first visit data and the second visit data.

Example 165

The system of Example 162, wherein the visits engine is further to compile the first visit charge and the second visit charge into a current batch of open charges and generate an open charges balance by aggregating all open charges of the current batch of open charges, the system further comprising: a balance brokering engine to evaluate the open charges balance based on asset sales criteria for determining whether the open charges balance should be transferred from the first billing system to a new system of record and effectuate electronic transactions to transfer title of an accounts receivable asset that constitutes rights to collect payment for the open charges balance, including payment for the current batch of open charges, to the new system of record, if the asset sales criteria are met; and wherein the system tracks the open charges balance, including payments to pay the one or more visit charges and other transactions relating to the open charges balance, wherein the system tracks the open charges balance separate from the first billing system and tracks transactions tracked in the first billing system that pertain to the one or more visit charges.

Example 166

The system of Example 165, further comprising: a scoring engine configured to extract propensity-to-pay ("PTP") characteristics from the first visit data and the second visit data, including PTP characteristics of the one or more guarantors, and calculate a PTP metric for a guarantor based on PTP characteristics of the guarantor extracted from the historical healthcare data, wherein the PTP metric indicates a likelihood that the guarantor will pay for visit charges for healthcare visits, wherein the PTP metric is one of the asset sales criteria upon which the balance brokering engine evaluates the open charges balance.

Example 167

The system of Example 162, further comprising: a financing engine to: present, to a guarantor of both the charge for the first visit and the charge for the second visit, pre-determined payment options for paying an open charges balance including the charge for the first visit and the charge for the second visit, each of the pre-determined payment options including terms at least partially defined by one of a present asset holder and a potential asset holder of the open charges balance; receive, at the payment management system, a guarantor selection of one of the pre-determined payment options for paying the open charges balance; and determine a payment amount based on the selected one of the pre-determined payment options.

Example 168

A computer-implemented method for managing payments for services, the method comprising: receiving at one or more computing devices first visit data from a first billing system, the first visit data including a charge for a first visit; receiving at the one or more computing devices second visit data being tracked in a second billing system that is independent from the first billing system, the second visit data specifying a charge for a second visit; receiving at the one or more computing devices payment data specifying a payment vehicle for paying a payment amount; communicating a transaction request to a payment gateway to request the payment gateway process an electronic financial transaction to obtain payment funds in the payment amount from a payor financial institution associated with the payment vehicle, to transfer a first portion of the payment funds to a payee financial institution associated with the first patient billing system, and to transfer a second portion of the payment funds to a payee financial institution associated with the second patient billing system; and communicating one or more electronic posting files to notify the first billing system of transfer of the first portion of the payment funds toward payment of the charge for the first visit and to notify the second billing system of transfer of the second portion of the payment funds toward payment of the charge for the second visit.

Example 169

The method of Example 168, further comprising generating on the one or more computing devices an open charges balance by summing the charge for the first visit and the charge for the second visit to aggregate charges during a given time period and that are tracked in multiple billing systems.

Example 170

The method of Example 168, wherein the payment gateway is a remote third party gateway coupled to the one or more computers by a network, wherein communicating a transaction request to the payment gateway comprises transmitting the transaction request over the network.

Example 171

The method of Example 168, wherein the payment amount differs from the charge for the first visit and differs from the amount of the charge for the second healthcare visit.

Example 172

The method of Example 168, further comprising: receiving at the one or more computing devices payment option input specifying present or eventual asset holder pre-determined payment options; and receiving at the one or more computing devices a selection of one of the provider pre-determined payment options; and determining the payment amount based on the selected one of the provider pre-determined payment options.

Example 173

The method of claim Example 172, wherein the payment options input includes a pay-in-full discount.

Example 174

The method of Example 172, wherein the payment options input includes provider-determined preset financing terms.

Example 175

The method of Example 172, wherein the payment options input includes provider-determined parameters for guarantor-customized financing terms.

Example 176

The method of Example 168, further comprising generating a single longitudinal portrayal of visit data including the first visit data and the second visit data.

Example 177

The method of Example 176, further comprising providing the longitudinal portrayal to a client computing device over a network.

Example 178

The method of Example 168, wherein the first visit data specifies a charge for a first visit of a beneficiary and the second visit data specifies a charge for a second visit of the beneficiary.

Example 179

The method of Example 168, wherein the first visit data specifies a charge for a first visit of a beneficiary and the second visit data specifies a charge for a second visit of a second beneficiary.

Example 180

The method of Example 168, wherein the first visit is a first healthcare visit, the second visit is a second healthcare visit, and a beneficiary of the first healthcare visit and the second healthcare visit is a patient.

Example 181

The method of Example 168, wherein the first visit is a first healthcare visit of a first patient and the second visit is a second healthcare visit of a second patient.

Example 182

The method of Example 168, wherein the payment data specifies a payment vehicle of a guarantor of a beneficiary of the first visit and a beneficiary of the second visit.

Example 183

The method of Example 182, wherein the guarantor is the beneficiary of at least one of the first visit and the second visit.

Example 184

The method of Example 168, wherein the second visit data is received from the second billing system, wherein the second billing system is remote from the one or more computing devices.

Example 185

The method of Example 168, wherein the first visit data includes a charge for each of a first plurality of visits during a time period, and wherein the one or more electronic posting files to notify the first patient billing system of transfer of the first portion of the payment funds and allocates the first portion of the payment funds toward payment of the charge of one or more of the first plurality of visits.

Example 186

The method of Example 185, further comprising receiving at the one or more computing devices one or more payor preferences for specifying how a payment is to be allocated to among the first plurality of visit charges; generating the one or more electronic posting files based on the payor preferences.

Example 187

The method of Example 168, wherein the charge for the first visit is tracked in an account within the first billing system and the charge for the second visit is tracked in an account in the second billing system, wherein a first electronic posting file of the one or more electronic posting files specifies the account within the first billing system and a second electronic posting file of the one or more electronic posting files specifies the account within the second billing system.

Example 188

The method of Example 168, wherein the first billing system is associated with a first balance sheet entity and the second billing system is associated with a second balance sheet entity that is independent from the first balance sheet entity.

Example 189

The method of Example 168, wherein the charge for the first visit comprises an aggregation of a plurality of line item charges for the first visit, such that all the line item charges for the first visit were incurred for the first visit.

The above description provides numerous specific details for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps, or by a combination of hardware, software, and/or firmware.

Embodiments may also be provided as a computer program product including a computer-readable storage medium having stored instructions thereon that may be used to program a computer (or other electronic device) to perform processes described herein. The computer-readable storage medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions.

As used herein, a software module or component may include any type of computer instruction or computer-executable code located within a memory device and/or computer-readable storage medium. A software module may, for instance, comprise one or more physical or logical blocks of computer instructions, which may be organized as a routine, a program, an object, a component, a data structure, etc., that perform one or more tasks or implement particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be obvious to those having skill in the art that many changes may be made to the details of the above-described embodiments without departing from the underlying principles of the invention. The scope of the present invention should, therefore, be determined only by the following claims.

We claim:

1. A computer-implemented method for outputting information from linked accounts, performed by a computing system, the method comprising:
   obtaining first visit data from a first patient billing system and second visit data from a second patient billing system, the first visit data including healthcare billing information indicating a first visit charge for a first visit of a patient, and the second visit data including healthcare billing information indicating a second visit charge for a second visit of the patient, wherein the first visit data is provided from a first user account of the first patient billing system and the second visit data is provided from a second user account of the second patient billing system;
   receiving an account linking request, requested in a graphical user interface, to enable a guarantor to view and manage healthcare billing information from the respective user accounts in the first and second patient billing systems;
   defining security and viewing parameters for access of the guarantor to the healthcare billing information from the respective user accounts within outputs of the graphical user interface, by linking an account of the guarantor to the respective user accounts without updating the respective user accounts in the first and second patient billing systems, wherein the security and viewing parameters establish permissions for the guarantor to view and manage data that is obtained from the respective user accounts within the graphical user interface;
   generating a longitudinal representation of billing transactions aggregated among the respective user accounts in the first and second patient billing systems for output in the graphical user interface, wherein the longitudinal representation includes a representation of an amount of the first visit charge and an amount of the second visit charge, and wherein the longitudinal representation aggregates the first visit data with the second visit data; and
   providing the generated longitudinal representation for output to the guarantor in the graphical user interface, wherein the security and viewing parameters control access of the guarantor to the longitudinal representation and the healthcare billing information from the respective user accounts.

2. The method of claim 1, wherein the first user account of the first patient billing system is associated with a first guarantor account used in the first patient billing system, and wherein the second user account of the second patient billing system is associated with a second guarantor account used in the second patient billing system, and wherein the account linking request associates the guarantor with the first guarantor account and the second guarantor account respectively used in the first and second patient billing systems.

3. The method of claim 1, wherein the first visit data and the second visit data are tracked in billing systems associated with a provider of the first visit and a provider of the second visit respectively, and wherein the providers are distinct medical entities.

4. The method of claim 1, wherein the first patient billing system remains a system of record for the first visit charge, and wherein the second patient billing system remains a system of record for the second visit charge.

5. The method of claim 4, wherein the computing system is established as a system of record for a portion of a payment received for the first visit charge and the second visit charge.

6. The method of claim 1, further comprising:
   obtaining third visit data, the third visit data including healthcare billing information indicating a third visit charge, wherein the third visit data is provided from the first patient billing system, the second patient billing system, or a third patient billing system;
   wherein the longitudinal representation further includes a representation of an amount of the third visit charge that is aggregated with the first visit data and the second visit data; and
   wherein the third visit charge is provided from a third visit of the patient or another patient.

7. The method of claim 1, further comprising:
   receiving, based on input from the guarantor obtained in the graphical user interface, payment information for an electronic payment to apply to the first visit charge and to the second visit charge.

8. The method of claim 7, wherein the payment information for the electronic payment is established from user-configurable financing of an aggregated balance due among the first user account and the second user account, and wherein terms of the user-configurable financing are received based on input from the guarantor obtained in the graphical user interface.

9. A computing system, comprising at least one processor and memory coupled to the processor, wherein the memory stores instructions that, when executed by the processor, cause the computer system to perform operations comprising:
   obtaining first visit data from a first patient billing system and second visit data from a second patient billing system, the first visit data including healthcare billing information indicating a first visit charge for a first visit of a patient, and the second visit data including healthcare billing information indicating a second visit charge for a second visit of the patient, wherein the first visit data is provided from a first user account of the first patient billing system and the second visit data is provided from a second user account of the second patient billing system;
   receiving an account linking request, requested in a graphical user interface, to enable a guarantor to view and manage healthcare billing information from the respective user accounts in the first and second patient billing systems;
   defining security and viewing parameters for access of the guarantor to the healthcare billing information from the respective user accounts within outputs of the graphical user interface, by linking an account of the guarantor to the respective user accounts without updating the respective user accounts in the first and second patient billing systems, wherein the security and viewing parameters establish permissions for the guarantor to view and manage data that is obtained from the respective user accounts within the graphical user interface;

generating a longitudinal representation of billing transactions aggregated among the respective user accounts in the first and second patient billing systems for output in the graphical user interface, wherein the longitudinal representation includes a representation of an amount of the first visit charge and an amount of the second visit charge, and wherein the longitudinal representation aggregates the first visit data with the second visit data; and providing the generated longitudinal representation for output to the guarantor in the graphical user interface, wherein the security and viewing parameters control access of the guarantor to the longitudinal representation and the healthcare billing information from the respective user accounts.

10. The computing system of claim 9, wherein the first user account of the first patient billing system is associated with a first guarantor account used in the first patient billing system, and wherein the second user account of the second patient billing system is associated with a second guarantor account used in the second patient billing system, and wherein the account linking request associates an account of the guarantor used in the computer system with the first guarantor account and the second guarantor account respectively used in the first and second patient billing systems.

11. The computing system of claim 9, wherein the first visit data and the second visit data are tracked in billing systems associated with a provider of the first visit and a provider of the second visit respectively, and wherein the providers are distinct medical entities.

12. The computing system of claim 9, wherein the first patient billing system remains a system of record for the first visit charge, and wherein the second patient billing system remains a system of record for the second visit charge.

13. The computing system of claim 12, wherein the computing system is established as a system of record for a portion of a payment received for the first visit charge and the second visit charge.

14. The computing system of claim 9, further comprising:
obtaining third visit data, the third visit data including healthcare billing information indicating a third visit charge, wherein the third visit data is provided from the first patient billing system, the second patient billing system, or a third patient billing system;
wherein the longitudinal representation further includes a representation of an amount of the third visit charge that is aggregated with the first visit data and the second visit data; and
wherein the third visit charge is provided from a third visit of the patient or another patient.

15. The computing system of claim 9, further comprising:
receiving, based on input from the guarantor obtained in the graphical user interface, payment information for an electronic payment to apply to the first visit charge and to the second visit charge.

16. The computing system of claim 15, wherein the payment information for the electronic payment is established from user-configurable financing of an aggregated balance due among the first user account and the second user account, and wherein terms of the user-configurable financing are received based on input from the guarantor obtained in the graphical user interface.

17. A system for outputting information from linked accounts, comprising:
one or more processors;
one or more memory devices operably coupled to the one or more processors, the memory devices configured to:
store first visit data obtained from a first patient billing system and second visit data obtained from a second patient billing system, the first visit data including healthcare billing information indicating a first visit charge for a first visit of a patient, and the second visit data including healthcare billing information indicating a second visit charge for a second visit of the patient;
wherein the first visit data is provided from a first user account of the first patient billing system and the second visit data is provided from a second user account of the second patient billing system;
one or more storage media to host processor-executable instructions, comprising:
instructions to implement a linking engine with the one or more processors, which configure the one or more processors to:
receive an account linking request, requested in a graphical user interface, to enable a guarantor to view and manage healthcare billing information from the respective user accounts in the first and second patient billing systems;
define security and viewing parameters for access of the guarantor to the healthcare billing information from the respective user accounts within outputs of the graphical user interface; and
link an account of the guarantor to the respective user accounts without updating the respective user accounts in the first and second patient billing systems;
wherein the security and viewing parameters establish permissions for the guarantor to view and manage data that is obtained from the respective user accounts within the graphical user interface;
instructions to implement a visits engine with the one or more processors, which configure the one or more processors to:
aggregate the first visit data pertaining to the first visit charge with the second visit data pertaining to the second visit charge; and
instructions to implement a statement engine with the one or more processors, which configure the one or more processors to:
generate a longitudinal representation of billing transactions aggregated among the respective user accounts in the first and second patient billing systems for output in the graphical user interface, wherein the longitudinal representation includes a representation of an amount of the first visit charge and an amount of the second visit charge, based on the aggregated visit data; and
provide the generated longitudinal representation for output to the guarantor in the graphical user interface, wherein the security and viewing parameters control access of the guarantor to the longitudinal representation and the healthcare billing information from the respective user accounts.

18. The system of claim 17, wherein the first user account of the first patient billing system is associated with a first guarantor account used in the first patient billing system, and wherein the second user account of the second patient billing system is associated with a second guarantor account used in the second patient billing system, and wherein the account linking request associates an account of the guarantor used in the system with the first guarantor account and the second guarantor account respectively used in the first and second patient billing systems.

19. The system of claim 17, wherein the first visit data and the second visit data are tracked in billing systems associated with a provider of the first visit and a provider of the second visit respectively, and wherein the providers are distinct medical entities.

20. The system of claim 17, wherein the first patient billing system remains a system of record for the first visit charge, and wherein the second patient billing system remains a system of record for the second visit charge.

21. The system of claim 17, wherein the memory is configured to store third visit data, the third visit data including healthcare billing information indicating a third visit charge, wherein the third visit data is provided from the first patient billing system, the second patient billing system, or a third patient billing system, wherein the longitudinal representation further includes a representation of an amount of the third visit charge that is aggregated with the first visit data and the second visit data, and wherein the third visit charge is provided from a third visit of the patient or another patient.

22. The system of claim 17, the one or more storage media to further host instructions to implement a payment clearance and routing engine with the one or more processors, which configure the one or more processors to:

receive, based on input from the guarantor obtained in the graphical user interface, payment information for an electronic payment to apply to the first visit charge and to the second visit charge.

23. The system of claim 22, wherein the payment information for the electronic payment is established from user-configurable financing of an aggregated balance due among the first user account and the second user account, and wherein terms of the user-configurable financing are received based on input from the guarantor obtained in the graphical user interface.

24. The system of claim 17, wherein the linking engine further configures the one or more processors to request a digitally signed release from the guarantor in compliance with externally imposed rules to protect the healthcare billing information, wherein the linking engine receives the digitally signed release of the guarantor prior to the statement engine providing access to the longitudinal representation and the healthcare billing information from the respective user accounts.

\* \* \* \* \*